US009417257B2

(12) United States Patent
Butters et al.

(10) Patent No.: US 9,417,257 B2
(45) Date of Patent: Aug. 16, 2016

(54) SYSTEM AND METHOD FOR COLLECTING, STORING, PROCESSING, TRANSMITTING AND PRESENTING VERY LOW AMPLITUDE SIGNALS

(75) Inventors: John T. Butters, Del Mar, CA (US); Bennett M. Butters, Lacey, WA (US); Patrick Naughton, Seattle, WA (US); Miller Puckette, Encinitas, CA (US)

(73) Assignee: Nativis, Inc., Seattle, WA (US)

(*) Notice: Subject to any disclaimer, the term of this patent is extended or adjusted under 35 U.S.C. 154(b) by 779 days.

(21) Appl. No.: 13/555,025

(22) Filed: Jul. 20, 2012

(65) Prior Publication Data
US 2013/0041201 A1 Feb. 14, 2013

Related U.S. Application Data

(63) Continuation of application No. 12/209,088, filed on Sep. 11, 2008, now abandoned, which is a continuation of application No. 11/632,340, filed as application No. PCT/US2005/026629 on Jul. 27, 2005.

(60) Provisional application No. 60/674,083, filed on Apr. 21, 2005, provisional application No. 60/602,962, filed on Aug. 19, 2004, provisional application No. 60/593,006, filed on Jul. 30, 2004, provisional application No. 60/591,549, filed on Jul. 27, 2004.

(51) Int. Cl.
| | | |
|---|---|---|
| *G01N 33/50* | (2006.01) | |
| *G01N 37/00* | (2006.01) | |
| *G01F 1/66* | (2006.01) | |
| *G06G 7/58* | (2006.01) | |
| *G01F 1/56* | (2006.01) | |

(52) U.S. Cl.
CPC .............. *G01N 37/005* (2013.01); *G01F 1/66* (2013.01); *G01F 1/56* (2013.01)

(58) Field of Classification Search
CPC ..................................... G01F 1/56; G01F 1/66
See application file for complete search history.

(56) References Cited

U.S. PATENT DOCUMENTS

| | | | |
|---|---|---|---|
| 4,031,462 A | 6/1977 | Bouvier et al. | |
| 4,095,168 A | 6/1978 | Hlavka | |
| 4,365,303 A | 12/1982 | Hannah et al. | |
| 4,369,226 A | 1/1983 | Rembaum et al. | |
| 4,682,027 A | 7/1987 | Wells | |
| 4,692,685 A | 9/1987 | Blaze | |
| 4,751,515 A | 6/1988 | Corum | |
| 4,822,169 A | 4/1989 | Distl et al. | |
| 5,113,136 A | 5/1992 | Hayashi et al. | |
| 5,254,950 A | 10/1993 | Fan et al. | |
| 5,305,751 A | 4/1994 | Chopp et al. | |
| 5,339,811 A | 8/1994 | Ohta et al. | |
| 5,343,147 A | 8/1994 | Sager et al. | |
| 5,446,681 A | 8/1995 | Gethner et al. | |
| 5,458,142 A | 10/1995 | Farmer et al. | |
| 5,465,049 A | 11/1995 | Matsuura et al. | |
| 5,506,500 A | 4/1996 | Krause et al. | |
| 5,508,203 A | 4/1996 | Fuller et al. | |
| 5,541,413 A | 7/1996 | Pearson et al. | |
| 5,574,369 A | 11/1996 | Hibbs | |
| 5,583,432 A | 12/1996 | Barnes | |
| 5,656,937 A | 8/1997 | Cantor | |
| 5,696,691 A | 12/1997 | Schlosser et al. | |
| 5,734,353 A | 3/1998 | Van Voorhies | |
| 5,752,514 A | 5/1998 | Okamura et al. | |
| 5,789,961 A | 8/1998 | Bulsara et al. | |
| 5,944,782 A | 8/1999 | Noble et al. | |
| 5,952,978 A | 9/1999 | VanVoorhies | |
| 5,955,400 A | 9/1999 | Yokosawa et al. | |
| 5,959,548 A | 9/1999 | Smith | |
| 6,020,782 A | 2/2000 | Albert et al. | |
| 6,028,558 A | 2/2000 | Van Voorhies | |
| 6,084,242 A | 7/2000 | Brown et al. | |
| 6,084,399 A | 7/2000 | Nagaishi et al. | |
| 6,133,734 A | 10/2000 | McKeon | |
| 6,136,541 A | 10/2000 | Gulati | |

(Continued)

FOREIGN PATENT DOCUMENTS

| | | |
|---|---|---|
| AU | 2003231978 | 6/2005 |
| AU | 2003230950 | 2/2007 |

(Continued)

OTHER PUBLICATIONS

"Direct Nanoscale Conversion of Bio-Molecular Signals Into Electronic Information." DARPA Defense Sciences Office, 2 pages, <http://www.darpa.mil/dso/thrust/biosci/moldice.htm> (2003).
"Engineered Bio-Molecular Nano-Devices/Systems (MOLDICE)." DARPA Defense Sciences Office, 1 page, <http://www.darpa.mil/dso/thrust/biosci/moldice.htm> (2004).
"The First International Workshop on TFF; What is Biophysics Behind?" Abstract Booklet, 18 pages, <http://www.biophysics.nl/idras.htm> (Jun. 15, 1996).
International Search Report for PCT application PCT/US03/011834, search report dated Oct. 9, 2003, 4 pages (2003).
International Search Report for PCT application PCT/US03/009544, search report dated Sep. 9, 2003, 3 pages (2003).
International Search Report for PCT application PCT/US04/033383, search report dated May 27, 2005, 4 pages (2005).
International Search Report and Written Opinion for PCT application PCT/US05/26629, search report dated Aug. 7, 2008, 9 pages (2008).
Aissa et al. "Transatlantic Transfer of Digitized Antigen Signal by Telephone Link." *Digi Bio-FASEB 97*, Abstract only, <http://digibio.com/cgibin/node.QI?Ig=us&nd=n4.sub.--3> 1 p. (1997).
Aissa, et al. "Molecular signaling at high dilution or by means of electronic circuitry." *Journal of Immunology*, p. 146A, Abstract only (1994).

(Continued)

*Primary Examiner* — Eric S DeJong
(74) *Attorney, Agent, or Firm* — Perkins Coie LLP

(57) ABSTRACT

A method and apparatus for producing an effect of a chemical or biochemical agent on a system responsive to such agent, are disclosed. In practicing the method, a plurality of low-frequency time-domain signals of the agent are generated, each at a different at a different noise level within a selected noise level range. The signals are analyzed by producing spectral plots of the time-domain signals, and identifying an optimized agent-specific time-domain signal based on information in the spectral plots. A chemical or biological system responsive to the agent is exposed to the optimized time-domain signal by placing the system within the magnetic field of an electromagnetic transducer, and applying the signal to the transducer at a signal amplitude and for a period sufficient to produce in the system an agent-specific effect on the system.

16 Claims, 48 Drawing Sheets

(56) References Cited

U.S. PATENT DOCUMENTS

| | | | |
|---|---|---|---|
| 6,142,681 A | 11/2000 | Gulati | |
| 6,150,812 A | 11/2000 | Pinsky et al. | |
| 6,159,444 A | 12/2000 | Schlenga et al. | |
| 6,196,057 B1 | 3/2001 | Discenzo | |
| 6,201,821 B1 | 3/2001 | Zhu et al. | |
| 6,204,821 B1 | 3/2001 | Van Voorhies | |
| 6,285,249 B1 | 9/2001 | Bulsara et al. | |
| 6,294,911 B1 | 9/2001 | Shimazawa et al. | |
| 6,320,369 B1 | 11/2001 | Hidaka et al. | |
| 6,323,632 B1 | 11/2001 | Husher et al. | |
| 6,411,108 B1 | 6/2002 | Douglas et al. | |
| 6,516,281 B1 | 2/2003 | Wellstood et al. | |
| 6,541,978 B1 | 4/2003 | Benveniste et al. | |
| 6,586,931 B2 | 7/2003 | Taicher | |
| 6,665,553 B2 | 12/2003 | Kandori et al. | |
| 6,724,188 B2 | 4/2004 | Butters et al. | |
| 6,760,674 B2 | 7/2004 | Bombard | |
| 6,815,949 B2 | 11/2004 | Kandori et al. | |
| 6,885,192 B2 | 4/2005 | Clarke et al. | |
| 6,952,652 B2 | 10/2005 | Butters | |
| 6,995,558 B2 | 2/2006 | Butters et al. | |
| 7,081,747 B2 | 7/2006 | Butters et al. | |
| 7,130,692 B2 | 10/2006 | Brighton et al. | |
| 7,412,340 B2 | 8/2008 | Butters | |
| 7,575,934 B2 | 8/2009 | Atwood | |
| 2002/0158631 A1 | 10/2002 | Kandori et al. | |
| 2003/0016010 A1 | 1/2003 | Kandori et al. | |
| 2004/0027125 A1 | 2/2004 | Clarke et al. | |
| 2004/0174154 A1 | 9/2004 | Butters | |
| 2004/0183530 A1 | 9/2004 | Butters et al. | |
| 2004/0222789 A1 | 11/2004 | Pinsky et al. | |
| 2005/0030016 A1 | 2/2005 | Butters et al. | |
| 2005/0176391 A1 | 8/2005 | Butters | |
| 2006/0030896 A1 | 2/2006 | Simon et al. | |
| 2006/0158183 A1 | 7/2006 | Butters et al. | |
| 2007/0205767 A1 | 9/2007 | Xu et al. | |
| 2007/0210790 A1 | 9/2007 | Butters et al. | |
| 2007/0231872 A1 | 10/2007 | Butters et al. | |
| 2008/0011977 A1 | 1/2008 | Atwood | |
| 2008/0106261 A1 | 5/2008 | Romalis et al. | |
| 2009/0156659 A1 | 6/2009 | Butters et al. | |
| 2011/0279115 A1 | 11/2011 | Tuchman | |
| 2012/0089201 A1 | 4/2012 | Pilla | |
| 2012/0113423 A1 | 5/2012 | Groswasser | |
| 2013/0165734 A1 | 6/2013 | Butters | |

FOREIGN PATENT DOCUMENTS

| | | |
|---|---|---|
| AU | 2004280998 | 7/2008 |
| AU | 2005269345 | 12/2010 |
| AU | 2011201847 | 9/2013 |
| BR | PI0307210 | 12/2004 |
| BR | PI0415235 | 12/2006 |
| BR | PI0512678 | 4/2008 |
| BR | PI0513910 | 5/2008 |
| CA | 2460794 | 2/2005 |
| CA | 2538988 | 2/2011 |
| CA | 2684009 | 2/2011 |
| CA | 2473142 | 4/2011 |
| CA | 2573350 | 5/2014 |
| CN | ZL200480029490.2 | 5/2010 |
| CN | ZL200580025199.2 | 5/2012 |
| DE | 1815674 | 7/1969 |
| EP | 0060392 | 9/1982 |
| EP | 1792179 | 6/2007 |
| FR | 2783605 | 3/2000 |
| HK | 1104855 A | 1/2008 |
| IN | 229893 | 2/2009 |
| IN | 237823 | 1/2010 |
| IN | 252124 | 4/2012 |
| JP | 2008508523 | 3/2008 |
| JP | 4425639 | 12/2009 |
| JP | 4425922 | 3/2010 |
| JP | 5624708 | 10/2014 |
| WO | 8606493 | 11/1986 |
| WO | WO-8702981 | 5/1987 |
| WO | WO-9113611 | 9/1991 |
| WO | WO-9114181 | 9/1991 |
| WO | WO-9417406 | 8/1994 |
| WO | WO-9954731 | 10/1999 |
| WO | WO-0001412 | 1/2000 |
| WO | WO-0017637 | 3/2000 |
| WO | WO-0017638 | 3/2000 |
| WO | WO-03083429 | 10/2003 |
| WO | WO-03083439 | 10/2003 |
| WO | WO-03102566 | 12/2003 |
| WO | WO-2005036131 | 4/2005 |
| WO | 2005118858 | 12/2005 |
| WO | 2006015038 | 2/2006 |
| WO | WO-2006015038 | 2/2006 |
| WO | 2006060653 | 6/2006 |
| WO | 2006073491 | 7/2006 |
| WO | WO-2006073491 | 7/2006 |
| WO | 2008008257 | 1/2008 |
| WO | 2008023840 | 2/2008 |
| WO | WO-2008063654 | 5/2008 |
| WO | 2010117349 | 10/2010 |
| WO | 2011075692 | 6/2011 |
| WO | 2014011940 | 1/2014 |
| WO | 2014145284 | 9/2014 |

OTHER PUBLICATIONS

Aissa, et al. "Electronic transmission of the cholinergic signal." *FASEB Journal*, p. A683, Poster 3964, Abstract only (1995).

Aissa, et al. "Transfer of molecular signals via electronic circuitry." *FASEB Journal*, p. A602, Poster #3489, Abstract only (1993).

Atkins, P.W. "Rotational and Vibrational Spectra." *Physical Chemistry*, 1990, pp. 458-497, Oxford University Press, Oxford, UK (1990).

Benveniste et al. "A Simple and Fast Method for in Vivo Demonstration of Electromagnetic Molecular Signaling (EMS) via High Dilution or Computer Recording." *FASEB Journal*, vol. 13, p. A163, Abstract only (1999).

Benveniste et al. "Digital Biology: Specificity of the Digitized Molecular Signal." *FASEB Journal*, vol. 12, p. A412, Abstract only (1998).

Benveniste et al. "Specific Remote Detection of Bacteria Using an Electromagnetic/Digital Procedure." *FASEB Journal*, vol. 13, p. A852, Abstract only, <http://digibio.com/cgi-bin/node.pl?lg=us&nd=n4.sub.--12> (1999).

Benveniste et al. "The Molecular Signal is not Functional in the Absence of 'Informed' Water." *FASEB Journal*, vol. 13, p. A163, Abstract only, <http://digibio.com/cgi-bin/node.pl?lg=us&nd=n4.sub.--11> (1999).

Benveniste, et al. "Digital Recording/Transmission of the Cholinergic Signal." *DigiBio—FASEB 96*, Abstract only, <http://digibio.com/cgibin/node.pl?lg=us&nd=n4.sub.--4> (1996).

Benveniste, J. "From 'Water Memory' effects to 'Digital Biology.'" *Understanding Digital Biology*, 4 pages, <http://www.digibio.com/cgi-bin/node.pl?nd=n3>, Jun. 14, 1998.

Benveniste, J. "Molecular Signaling, What Is So Unacceptable for Ultra-Orthodox Scientists?" 2 pages, <http://www.digibio.com/cgi-bin/node.pl?nd=n5> (2003).

Benveniste, J. et al. "Transfer of the molecular signal by electronic amplification." *FASEB Journal*, p. A398, Poster #2304, Abstract only (1994).

Binhi, V. "An Analytical Survey of Theoretical Studies in the Area of Magnetoreception." 11 pages, <http://www.biomag.info/survey.htm> (1999).

Brault, J., et al. "The Analysis and Restoration of Astronomical Data via the Fast Fourier Transform." *Astronomy and Astrophysics*, 11(2):169-189 (1971).

Brigham, E. "The Fast Fourier Transform and Applications." Prentice Hall, pp. 131-145 (1988).

Bruno, A.C. and Espy, M.A. "Design of a SQUID Array as a discrete spatial filter", *Superconductor Science and Technology*, 17:908-915 (2004).

(56) References Cited

OTHER PUBLICATIONS

Chapeau-Blondeau, F. "Input-output gains for signal in noise in stochastic resonance." Elsevier Science B.V, *Physics Letters A*, 232:41-48 (1997).
Chapeau-Blondeau, F. "Periodic and Aperiodic Stochastic Resonance with Output Signalto-Noise Ratio Exceeding That At the Input", *International Journal of Bifurcation and Chaos*, 9(1):267-272 (1999).
Chemla et al. "Ultrasensitive magnetic biosensor for homogeneous immunoassay." *PNAS*, 97(26): 14268-14272 (2000).
Cooley, J. et al. "An Algorithm for the Machine Calculation of Complex Fourier Series." *Mathematics of Computation*, American Mathematical Society, Providence, Rhode Island, 19(90):297-301 (1965).
DigiBio S.A. "Experimental models, From 'Water Memory' effects to 'Digital Biology.'" <http://digibio.com/cgi-bin/node.pl?nd=n7> (2003).
Duhamel, P., et al. "Split radix FFT algorithm." *Electronics Letters, The Institution of Electrical Engineers*, 20(1):14-16 (1984).
Glanz, J. "Sharpening the Senses with Neural 'Noise.'" *Science*, 277(5333), 2 pages (1997), <http://complex.gmu.edu/neural/papers/others/science97.sub.--noise.htm- 1>.
Gorgun, S. "Studies on the Interaction Between Electromagnetic Fields and Living Matter Neoplastic Cellular Culture.", 7(2):22 pages (1998), <http://bodyvibes.com/study1.htm>.
Hibbs et al. "Signal Enhancement in a r.f. SQUID using Stochastic Resonance." *IL Nuovo Cimento*, 17:811-817 (1995).
Hoffman, F. "An Introduction to Fourier Theory", 10 pages, <http://aurora.phys.utk.edu/.about.forrest/papers/fourier/index.html&g- t> (2004).
Ingram, D.J.E. "Spectroscopy at Radio and Microwave Frequencies." pp. 1-16, Butterworths, London, UK (1967).
Kaufman, I. et al. "Zero-dispersion stochastic resonance in a model for a superconducting quantum interference device." *Physical Review E*, 57(1):78-87, The American Physical Society (1998).
Lugrum, P.J.E. "Spectroscopy at Radio and Microwave Frequencies." Buterwort's London, pp. 1-16 (1967).
Harris, R.K. Chapter 18, Longman, London, "Nuclear Magnetic Resonance." pp. 535-563 (1986).
Neuhauser, R., "Hydrogenlike Rydberg Electrons Orbiting Molecular Clusters." *Physical Review Letters*, The American Physical Society, 80(23):5089-5092 (1998).
Nokazi, D., et al. "Effects of Colored Noise on Stochastic Resonance in Sensory Neurons." *Physical Review Letters*, The American Physical Society, 82(11):2402-2405 (1999).
Oppenheim, et al. "Digital Signal Processing." Prentice-Hall, ISBN 0-13-214635-5, pp. 87-121 (1975).
Proakis, J.G., et al. "Advanced digital signaling processing." Maxwell MacMillan, pp. 31-57 (1992).
Soma, R. "Noise Outperforms White Noise in Sensitizing Baroreflex Function in the Human Brain." The American Physical Society, *Physical Review Letters*, 91(7), 4 pages (2003).
Thomas, et al. "Direct transmission to cells of a molecular signal via an electronic device." *FASEB Journal*, p. A227, Poster # 1320, Abstract only (1995).
Thomas, et al. "Modulation of Human Neutrophil Activation by 'Electronic' Phorbol Myristate Acetate (PMA)." *DigiBio*, Abstract only, <http://www.digibio.com/cgibin/node.pl?lg=us&nd=n4.sub.--5> (1996).
Thomas, Y., et al. "Activation of human neurophils by electronically transmitted phorbol-myristate acetate." *Medical Hypotheses*, 54(1):33-39 (2000).
Turin, L. "A spectroscopic mechanism for primary olfactory reception." *Chemical Senses*, 21 (6):773-791 (1996).
Weaver, J., et al. "The response of living cells to very weak electric fields: the thermal noise limit." *Science*, 247(4941):459-462, Abstract only, <http://www.ncbi.nlm.nih.gov/entrez/query.fcgi?db=PubMed&cmd=Retrieve&-list.sub.--uids=2300806&dopt=Citation> (1990).
Atkins, P.W. "Magnetic Resonance." Chapter 18, *Physical Chemistry*, Oxford University Press, Oxford, UK, 1990, pp. 535-563 (1990).

Maehle, et al. "The emergence of the drug receptor theory." *Nat. Rev. Drug Disc.*, vol. 1, No. 8, pp. 637-641 (2002).
Mulder, et al. "Improved HSQC experiments for the observation of exchange broadened signals." *J. Biomol. NMR*, vol. 8, No. 2, pp. 223-228 (1996).
Balog, A. et al., "Total Synthesis of ( − )-Epothilone A**", Angewandte Chemie International Edition in English, vol. 35, Issue 23-24, Dec. 1996, pp. 2801-2803.
Bendat, J. S. et al., Engineering Applications of Correlation and Spectral Analysis, 2nd edition. Wiley-Interscience, 1993, Abstract only.
Crut, A. et al., "Detection of single DNA molecules by multicolor quantum-dot end-labeling", Nucleic Acids Research, vol. 33, No. 11, e98, 2005, pp. 1-9.
Dubertret, B. et al., "In Vivo Imaging of Quantum Dots Encapsulated in Phospholipid Micelles", Science, vol. 298, Nov. 29, 2002, pp. 1759-1762.
Gao, X. et al., "In vivo molecular and cellular imaging with quantum dots", Current Opinion in Biotechnology, vol. 16, 2005, pp. 63-72.
Grabarek, et al., "Zero-Length Crosslinking Procedure with the Use of Active Esters", Journal of Analytical Biochemistry, vol. 185, 1990, pp. 131-135.
Haller et al., "Low Tc SQUID Measurement System for Magnetic Relaxation Immunoassays in Unshielded Environment", IEEE Transactions on Applied Superconductivity, vol. 11, Mar. 2001, pp. 1371-1374.
Han et al., "Quantum-dot-tagged microbeads for multiplexed optical coding of biomolecules", Nature Biotechnology, vol. 19, Jul. 2001, pp. 631-635.
Hatanaka, S. et al.: "Direct immobilization of fluorescent dyes onto ferrite nanoparticles during their synthesis from aqueous solution", Journal of Applied Physics, American Institute of Physics. New York, US, vol. 93, No. 10, May 15, 2003, pp. 7569-7570.
Hendrickson, W., "Protein—DNA Interactions Studied by the Gel Electrophoresis—DNA Binding Assay", BioTechniques, vol. 3, May/Jun. 1985, pp. 198-207.
United States Patent and Trademark Office International Searching Authority, International Search Report; International Patent Application No. PCT/US2009/002184; Applicant: Nativis, Inc.; mailed: Jun. 4, 2009; 2 pages.
Lee, J. C. et al., "In Vitro Reconstitution of Calf Brain Microtubules: Effects of Solution Variables", Biochemistry, vol. 16, No. 8, Apr. 19, 1977, pp. 1754-1764.
Magana, D. J. et al., "Switching-on Superparamagnetism in MN/CdSE Quantum Dots", Journal of American Chemical Society, vol. 128, No. 9, 2006, pp. 2931-2939.
"MDA-MB-435S (ATCC HTB 129) Product Sheet", American Type Culture Collection, 3 pages, < http://www.atcc.org/Products/All/HTB-129.aspx#documentation> (2014).
Melle, S. et al., "Structure and dynamics of magnetorheological fluids in rotating magnetic fields", The American Physical Society: Physical Review E, vol. 61., No. 4, Apr. 2000, pp. 4111-4117.
Moini, H. et al., "Protein Binding of Procyanidins: Studies Using Polyacrylamide Gel Electrophoresis and French Maritime Pine Bark Extract", Methods in Enzymology, vol. 335, 2001, pp. 333-337.
Morozov et al.: "Active bead-linked immunoassay on protein microarrays", Analytica Chimica Acta, Elsevier, Amsterdam, NL, vol. 564, No. 1, Mar. 30, 2006, pp. 40-52.
Mulvaney, S. et al., "Incorporating fluorescent dyes and quantum dots into magnetic microbeads for immunoassays", BioTechniques, vol. 36, Apr. 2004, pp. 602-609.
Nuzzo, R. et al., "Adsorption of Bifunctional Organic Disulfides on Gold Surfaces", Journal of American Chemical Society, vol. 105, No. 13, 1983, pp. 4481-4483.
Olivos, H. et al., "Quantum Dots As a Visual Aid for Screening Bead-Bound Combinatorial Libraries", ChemBioChem, vol. 4, 2003, pp. 1242-1245.
Shelanski, M. L. et al., "Microtubule Assembly in the Absence of Added Nucleotides", Proceeding of the National Academy of Sciences U.S.A., vol. 70, No. 3, Mar. 1973, pp. 765-768.
Staros, J. et al., "Enhancement by N-Hydroxysulfosuccinimide of Water-Soluble CarbodiimideMediated Coupling Reactions", Analytical Biochemistry, vol. 156, 1986, pp. 220-222.

(56) References Cited

OTHER PUBLICATIONS

United States Patent and Trademark Office International Searching Authority, International Preliminary Report on Patentability; International Patent Application No. PCT/US2009/002184; Applicant: Nativis, Inc.; mailed: Oct. 11, 2011; 8 pages.

Temperton, C. "Implementation of a Self-Sorting In-Place Prime Factor FFT Algorithm", Journal of Computation Physics, v. 58, p. 283, 1985.

United States Patent and Trademark Office International Searching Authority, Written Opinion of the International Searching Authority; International Patent Application No. PCT/US2009/002184; Applicant: Nativis, Inc.; mailed: Jun. 4, 2009; 7 pages.

Wikswo, J. et al., "Magnetic Field of a Nerve Impulse: First Measurements", Science, vol. 208, Apr. 4, 1980, pp. 53-55.

Yi, D. et al., "Silica-Coated Nanocomposites of Magnetic Nanoparticles and Quantum Dots", Journal of American Chemical Society, vol. 127, 2005, pp. 4990-4991.

Hore et al., "Spin-Spin Coupling," Nuclear Magnetic Resonance, Chapter 3, Oxford University Press, 1995, pp. 22-43.

European Patent Office, Supplemental European Search Report; EP Application No. 13817486.7; Applicant: Nativis, Inc.; mailed: Dec. 2, 2015; 10 pages.

400 mV noise signal applied. No stochastic event visible.

600 mV noise signal applied. No stochastic event visible.

700 mV noise signal applied. Stochastic event visible.

900 mV noise signal applied. No stochastic event visible.

SYSTEM AND METHOD FOR COLLECTING, STORING, PROCESSING, TRANSMITTING AND PRESENTING VERY LOW AMPLITUDE SIGNALS

CROSS-REFERENCE TO RELATED APPLICATION(S)

This application is a continuation of U.S. patent application Ser. No. 12/209,088, filed Sep. 11, 2008, now abandoned which is a continuation of U.S. patent application Ser. No. 11/632,340 entitled SYSTEM AND METHOD FOR COLLECTING, STORING, PROCESSING, TRANSMITTING AND PRESENTING VERY LOW AMPLITUDE SIGNALS, filed Jun. 22, 2007, now abandoned, which is a U.S. National Stage of International Patent Application No. PCT/US2005/26629, filed Jul. 27, 2005, which claims the benefit of U.S. Provisional Patent Application No. 60/593,006, entitled SYSTEM AND METHOD FOR PRODUCING CHEMICAL OR BIOCHEMICAL SIGNALS, filed Jul. 30, 2004; U.S. Provisional Patent Application No. 60/591,549, entitled SIGNAL PROCESSING SYSTEM, SUCH AS FOR PRODUCING AND MANIPULATING SIGNALS FROM CHEMICAL OR BIOCHEMICAL COMPOUNDS OR SAMPLES, filed Jul. 27, 2004; U.S. Provisional Patent Application No. 60/602,962, entitled TRANSDUCING SIGNALS AND METHODS, filed Aug. 19, 2004; and U.S. Provisional Patent Application No. 60/674,083, entitled SYSTEM AND METHOD FOR PRODUCING CHEMICAL OR BIOCHEMICAL SIGNALS, filed Apr. 21, 2005.

TECHNICAL FIELD

The present invention relates to apparatus and effect for producing chemical or biological signals capable of producing one or more of the effects of a chemical or biological effector agent.

BACKGROUND

One of the accepted paradigms in the fields of chemistry and biochemistry is that chemical or biochemical effector agents, e.g., molecules, interact with target systems through various physicochemical forces, such as ionic, charge, or dispersion forces or through the cleavage or formation of covalent of charge-induced bonds. These forces may involve vibrational or rotational energy modes in either the effector agent or target system.

Thus, for example, when a drug molecule is administered to a biological organism, the action of the drug involves its interaction with target components, e.g., membrane, enzyme, or nucleic acid components, to produce or trigger a chain of events associated action of the drug. Similarly, if an enzyme is added to a biological substrate, the enzyme is able to interact with substrate through some type of spatial coordination, and energetic modes present in the system are transduced into an active or activated state leading to covalent bond cleavage or formation.

A corollary of this paradigm is the requirement, in effector-target systems, of the effector agent in the target environment. However, what is not known or understood is whether this requirement is related to the actual presence of the effector, or whether it may be due, at least as to certain effector functions, to the presence of energetic modes that are characteristic of the effector. If effector function can be simulated, at least in part, by certain characteristic energetic modes, it may be possible to "simulate" the effect of the effector agent in a target system by exposing the system to certain energetic modes that are characteristic of the effector. If so, the questions that naturally arise are: what effector-molecule energy modes are effective, how can they be converted or transduced into the form of measurable signals, and how can these signals be used to effect a target system, that is, mimic at least some of the effector functions of the molecule in a target system?

These questions were addressed in recently filed co-owned patent applications 60/593,006 and 60/591,549. Experiments conducted in support of the invention described in the application demonstrate that certain effector functions on a target system (in this case, one of a number of biological systems), can be duplicated by exposing the target system to electromagnetic waves produced by "transducing" a time-domain signal of the effector compound. According to the earlier-described invention, the time-domain signal is produced by recording a signal produced by the compound in a shielded environment, while injecting noise into the recording apparatus at a level that enhances the ability to observe low-frequency stochastic events produced by the compound. In the earlier-described application, the transducing signal was the actual compound time-domain signal of the effector compound.

The possibility of achieving effector-molecule functions by exposing a target system to characteristic effector-molecule signals, without the need for the actual presence of the effector agent, has a number of important and intriguing applications. Instead of treating an organism by the application of a drug, the same effect may be achieved by exposing the organism to drug-specific signals. In the field of nanofabrication, it might now be possible to catalyze or encourage self-assembly patterns by introducing in the assembly system, signals characteristic of a multivalent effector molecules capable of promoting the desired pattern of self-assembly.

The present invention describes apparatus and methods for achieving effector-specific results in systems known to be responsive to the effector, by transduction with low-frequency signals that are characteristic of the effector molecule.

SUMMARY

The invention includes, in one aspect, a method for producing an effect of a chemical or biochemical agent on a system responsive to such agent. In practicing the method, a plurality of low-frequency time domain signals are obtained by (i) placing a sample containing the agent in a container having both magnetic and electromagnetic shielding, (ii) injecting noise into the sample at a given noise amplitude; (iii) recording an electromagnetic time-domain signal composed of sample source radiation superimposed on the injected Gaussian noise, and (iv) repeating steps (ii)-(iii) at each of a plurality of noise levels in a selected range.

The plurality of time domain signals are then analyzed to identify an optimized agent-specific time-domain signal. This analysis may be carried out, for example, by one of three general methods disclosed herein. In the first, each signal is used to generate a histogram that shows, for each event bin f over a selected frequency range, the number of event counts in each bin, where f is a sampling rate for sampling the time domain signal, assigning to the histogram, a score related to the number of bins that are above a given threshold. The time-domain signal is selected on the basis of this bin-number score.

In the second approach, each of the time domain signals is autocorrelated and transformed by a Fast Fourier Transform, and the FFT of the autocorrelated signal is assigned a score related to the number of peaks above a noise mean average value. The time-domain signal(s) having the highest score are selected.

The third approach involves calculating a series of Fourier spectra of the time-domain signal over each of a plurality of defined time periods, in a selected frequency range between DC and 50 KHz, and averaging the Fourier spectra.

The agent-responsive system is exposed to the agent-specific spectral signal identified as above by placing the system within the magnetic field of an electromagnetic transducer, and applying the selected signal to the transducer at a signal amplitude and for a period sufficient to produce in the system an agent-specific effect on the system.

In obtaining the time-domain signals, the noise is preferably injected into a Helmholz coil surrounding the sample, at a selected noise output in the range up to 1 volt. The signal is preferably recorded using a gradiometer coupled to a SQUID, with the noise being injected into the gradiometer. The source of noise may be, for example, Gaussian or uniform noise, and the noise range over which the noise is injected is preferably between about 30 to 35 decibels above the molecular electromagnetic emissions sought to be detected The electromagnet transducer may include a coil winding defining an open interior, with the sample being placed within the open interior of said winding during exposure to the signal. In another embodiment, the electromagnet transducer includes an implantable coil, with the transducer being implanted in a biological system prior to exposure to the signal.

In another aspect, the invention includes an apparatus for producing an effect of a chemical or biochemical agent on a system responsive to such agent. The apparatus includes a shielded container for receiving a sample of the agent, an adjustable-power source of noise for injecting noise, e.g., Gaussian or uniform noise, into the sample at each of a plurality of noise levels in a selected range, e.g., up to a noise level of 1 volt, and between about 30 to 35 decibels above the molecular electromagnetic emissions sought to be detected. A detector in the apparatus records the electromagnetic time-domain signal composed of sample source radiation superimposed on the injected noise, and the signals recorded at the different noise levels are stored in a memory device.

An electronic unit in the apparatus functions to receive each of the plurality of time-domain signals stored in the memory device, and process the signals so as to permit identification of an optimized agent-specific time-domain signal, e.g., by one of the signal-analysis methods above. An electromagnet transducer in the apparatus is used for exposing the agent-responsive system to the optimized time-domain signal, at a signal amplitude and for a period sufficient to produce in the system an agent-specific effect on the system.

The sample container in the apparatus may be an attenuation tube having a sample-holding region, a magnetic shielding cage surrounding said region, and a Faraday cage contained within the magnetic shielding cage and also surrounding the sample-holding region. The source of noise may include a noise generator and a Helmholz coil which is contained within the magnetic cage and the Faraday cage, and which receives a noise output signal from the noise generator. The detector is preferably a gradiometer coupled to a SQUID, with the noise being injected into the gradiometer. The detector may further include a signal inverter operatively connected to the noise source and to the SQUID, for receiving noise from the noise source and outputting into said SQUID, noise in inverted form with respect to the noise injected into the sample.

The electromagnet transducer may include a coil winding and an open interior into which the sample is adapted to be placed. In another embodiment, the electrogmagnetic transducer may be a Helmholz coil having a pair of aligned electromagnetic coils defining an exposure station therebetween, and said exposing includes placing the sample within said station. In yet another embodiment, electromagnet transducer includes an implantable coil.

In another aspect, the invention includes an optimized agent specific time-domain signal produced by the above method.

These and other objects and features of the invention will become more fully apparent when the following detailed description of the invention is read in conjunction with the accompanying drawings.

Figure 16:
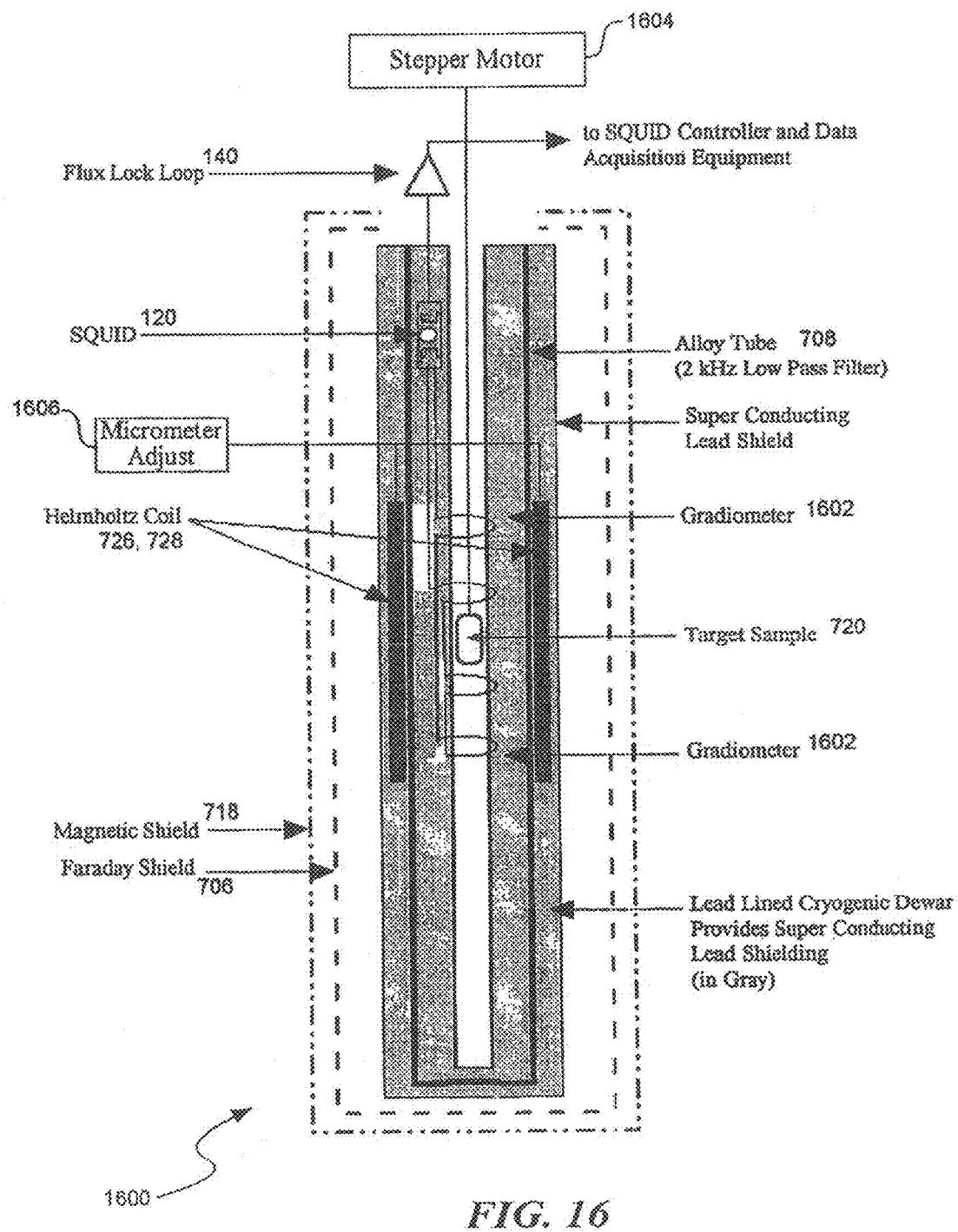

FIG. 16 is a schematic diagram illustrating an alternative embodiment of a molecular electromagnetic signaling detection apparatus.

Figure 17A:
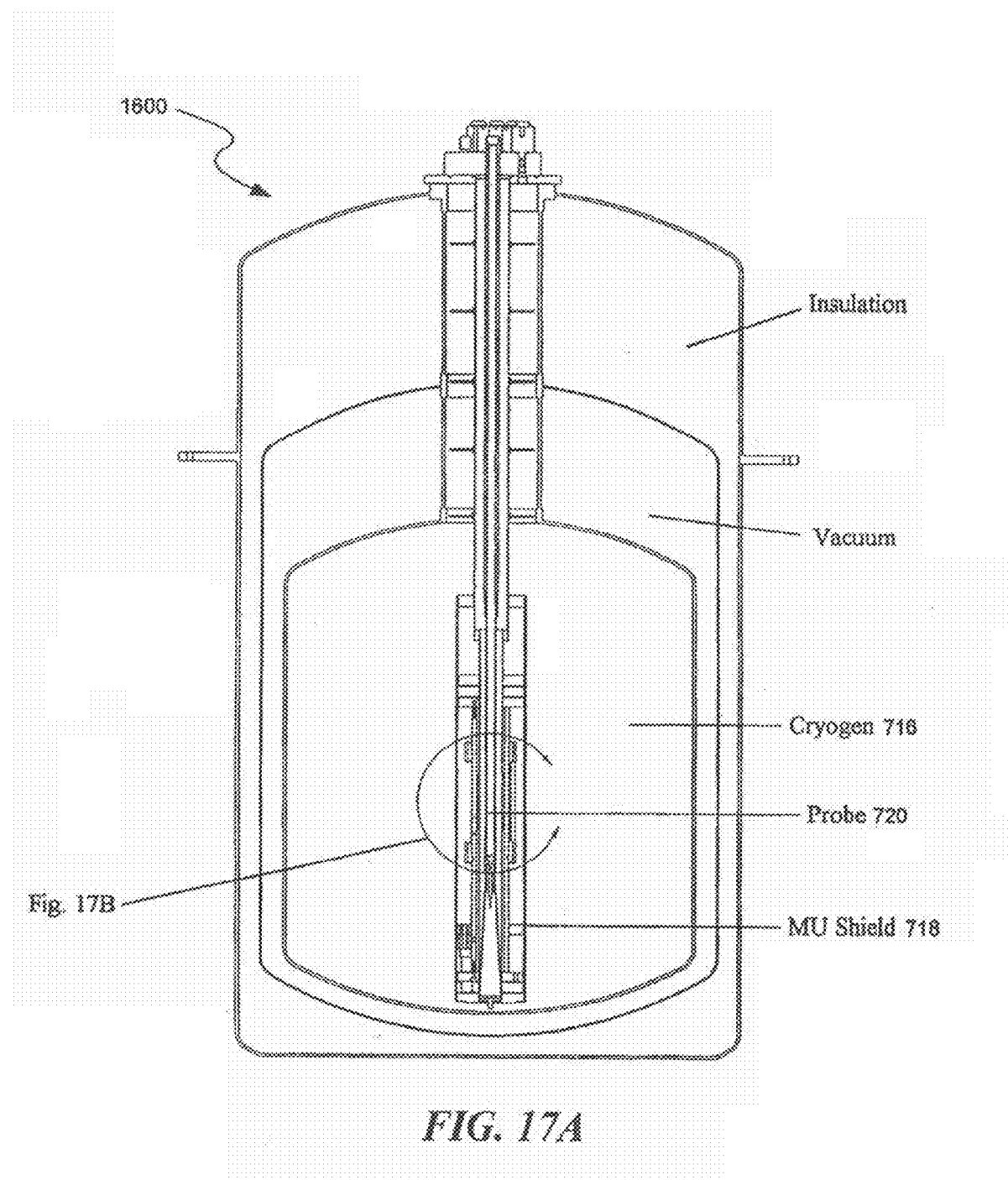
Figure 17B:
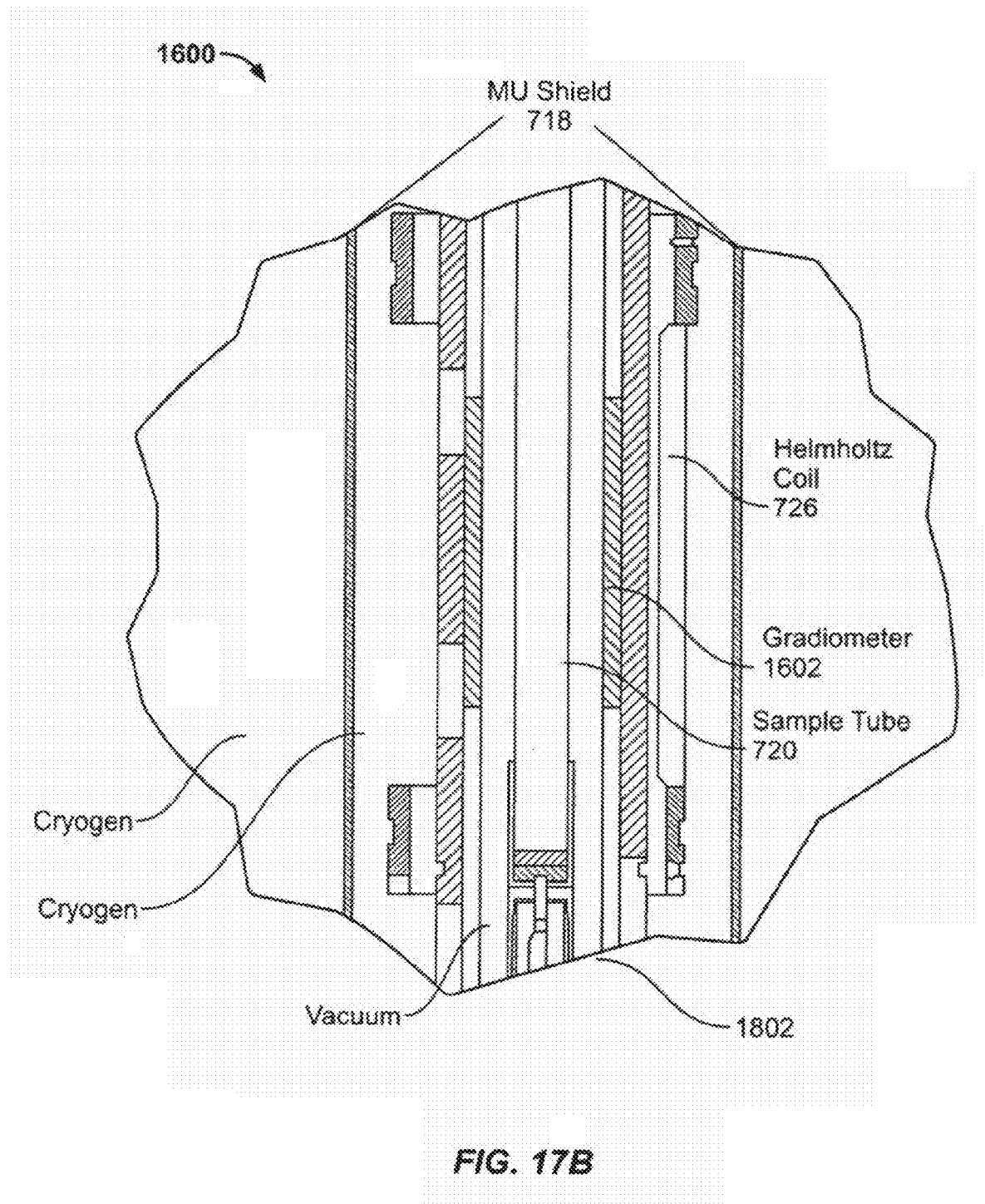

FIG. 17A is a cross-sectional view of the alternative embodiment of FIG. 16; FIG. 17B is an enlargement of a portion of FIG. 17A.

Figure 18:
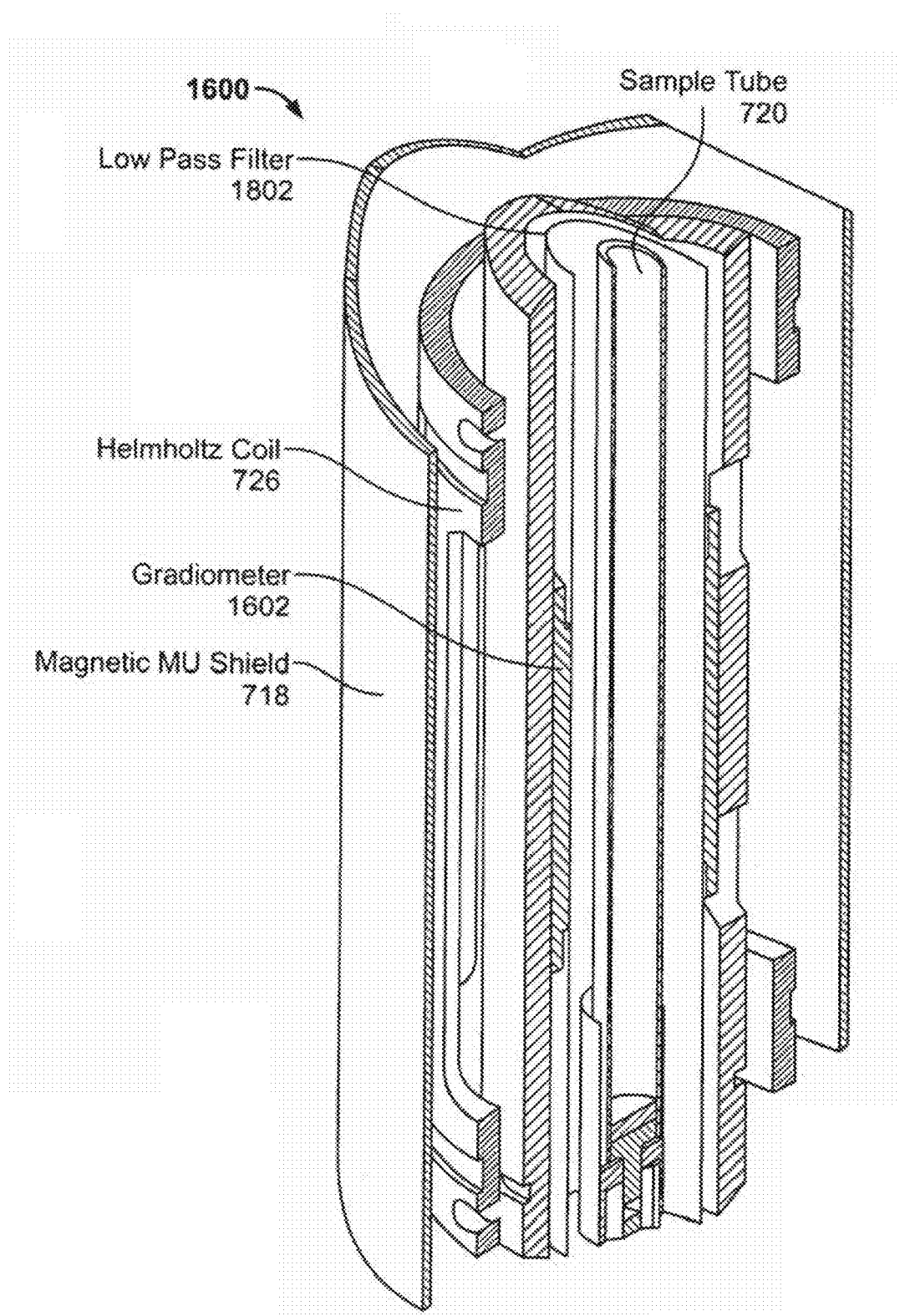

FIG. 18 is a cross-sectional isometric view of FIG. 17B.

Figure 9:
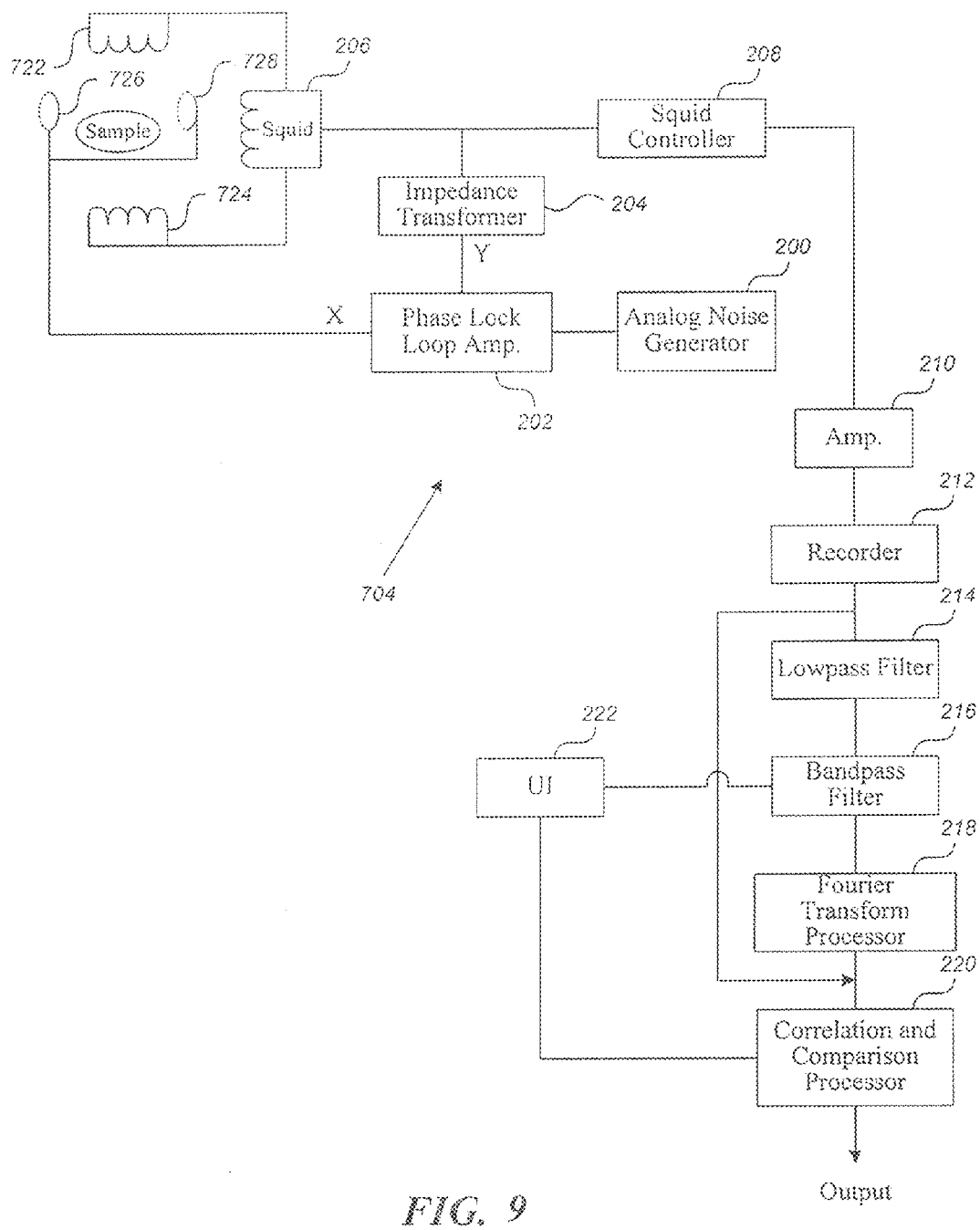
FIG. 9 is a diagram of an alternative processing unit to that of FIG. 8.
Figure 19:
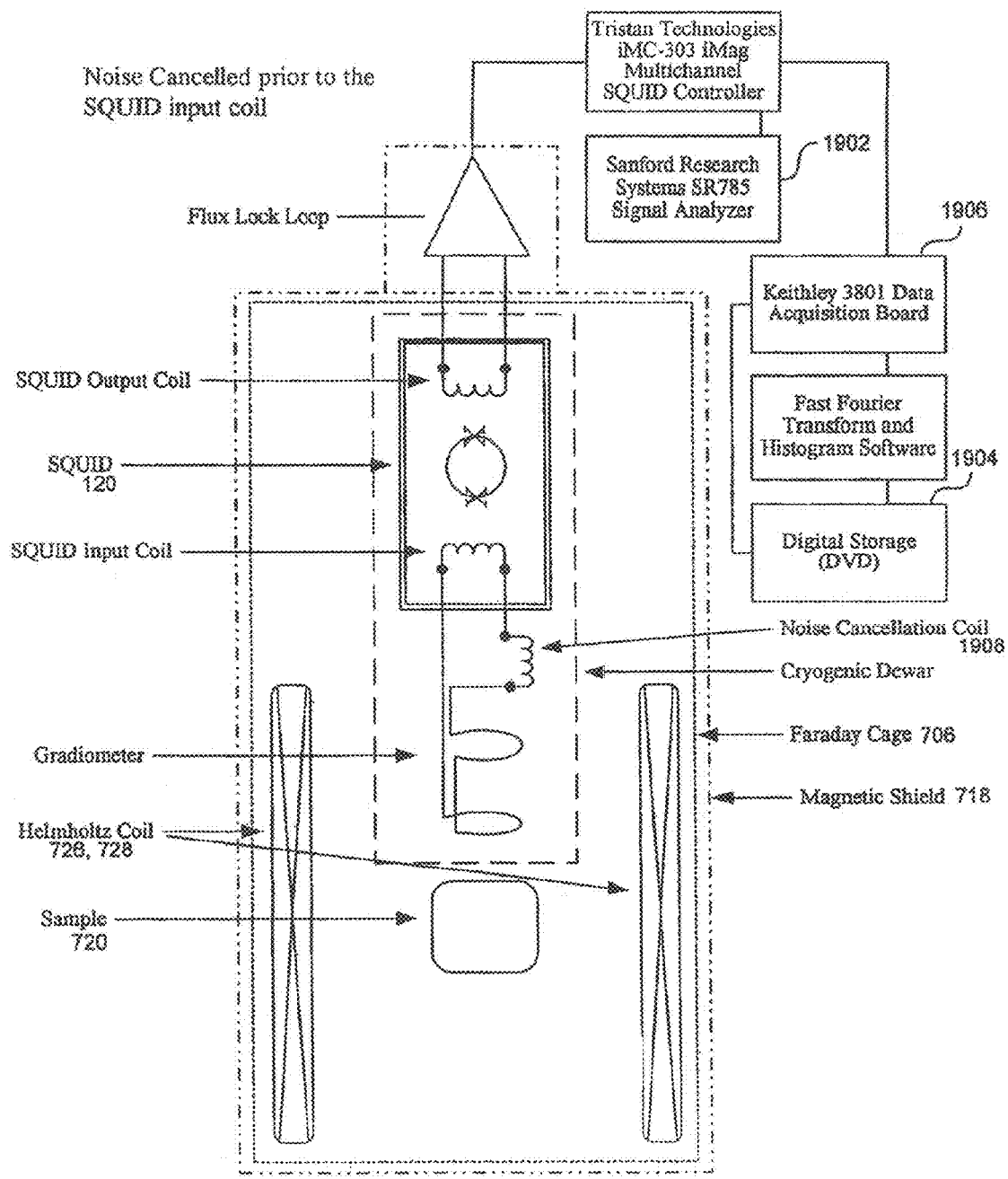

FIG. 19 is a diagram of an alternative processing unit to that of FIG. 9.

Figure 20:
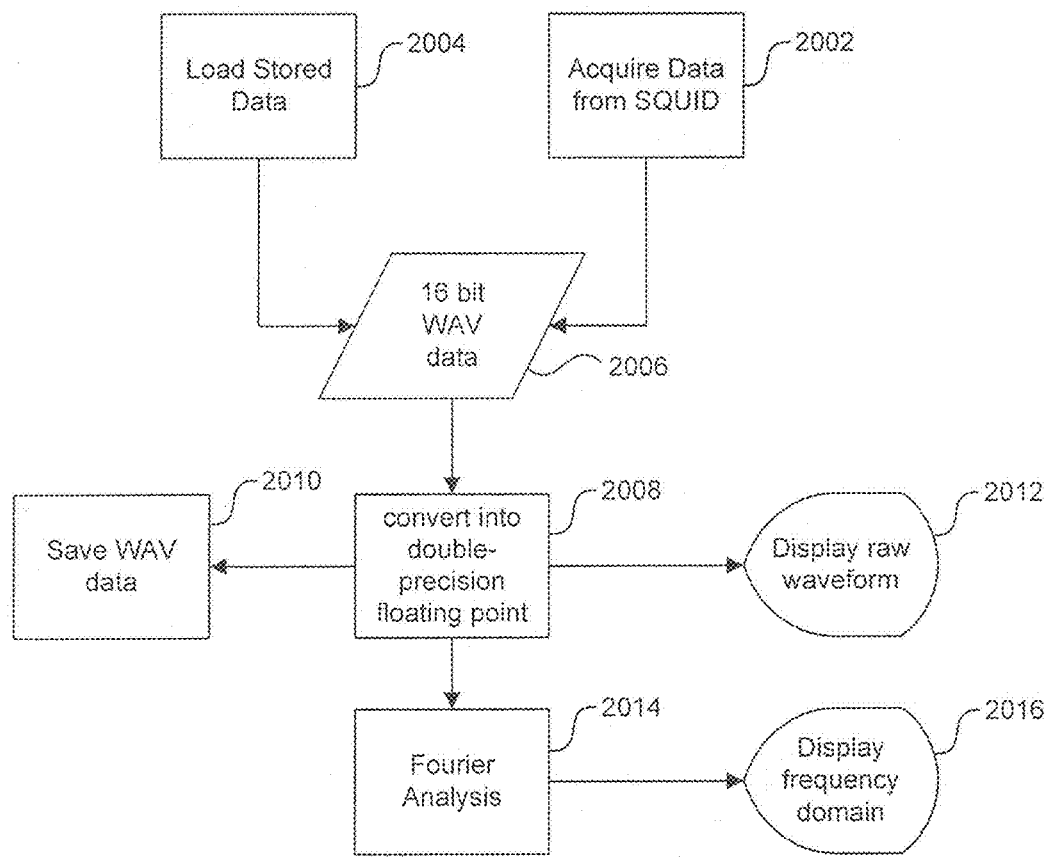
Figure 21:
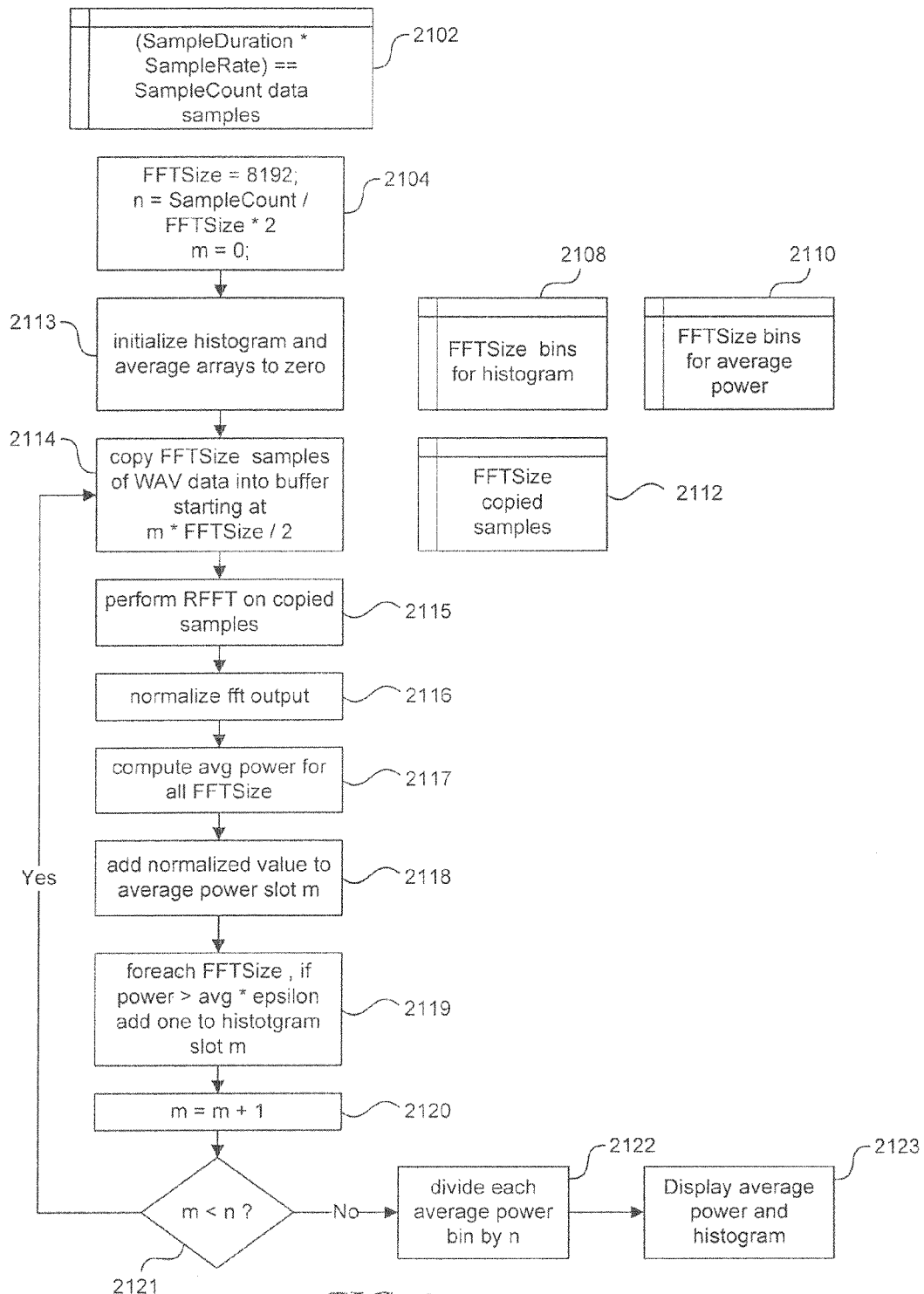

FIG. 20 shows a high-level flow diagram of data flow for the histogram spectral plot method of the invention;

FIG. 21 is a flow diagram of the algorithm for generating a spectral plot histogram, in accordance with the invention, and FIGS. 22A-22D are histogram spectra of a sample taken at four different noise power levels.

Figure 23A:
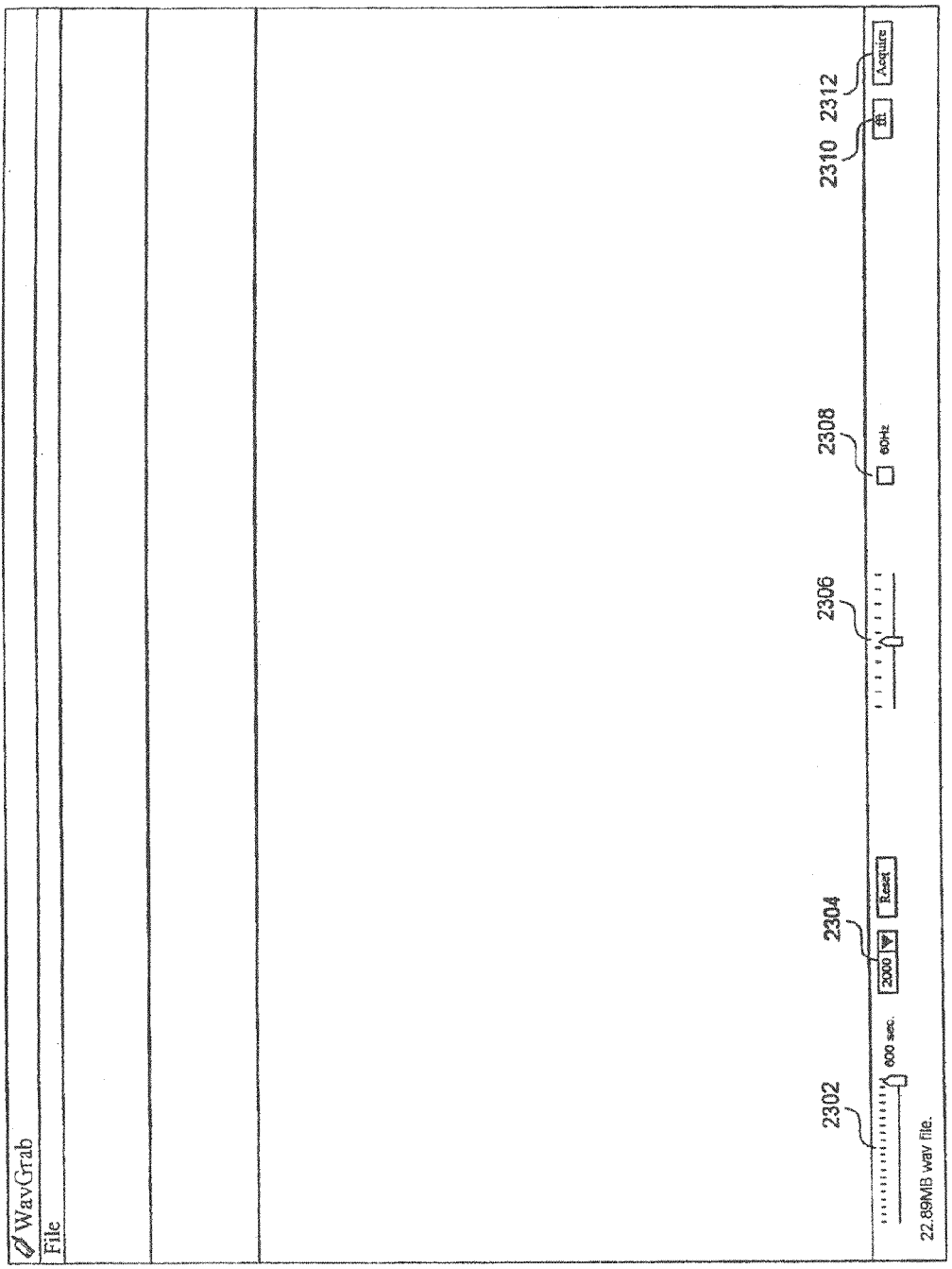
Figure 23B:
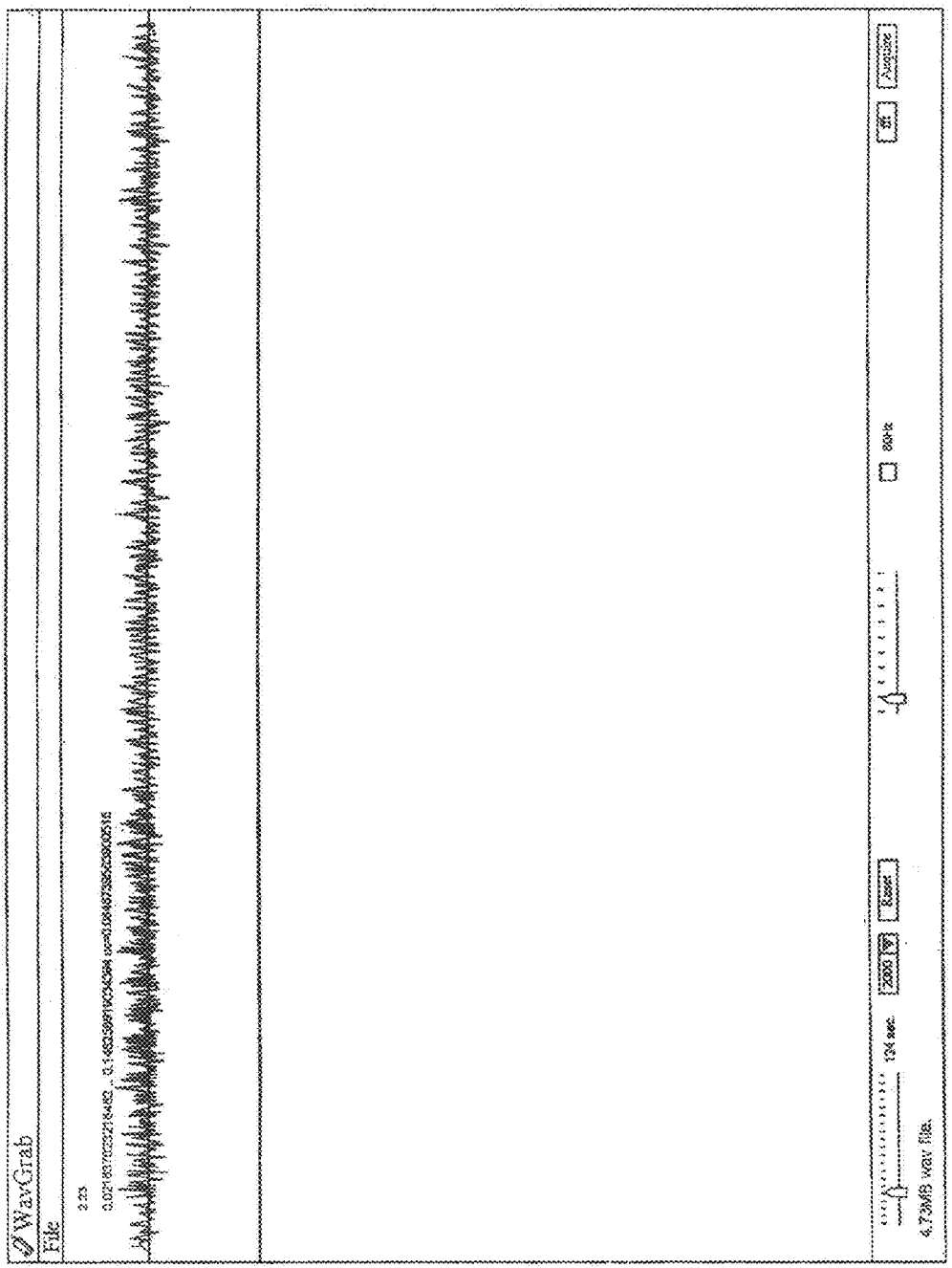
Figure 23C:
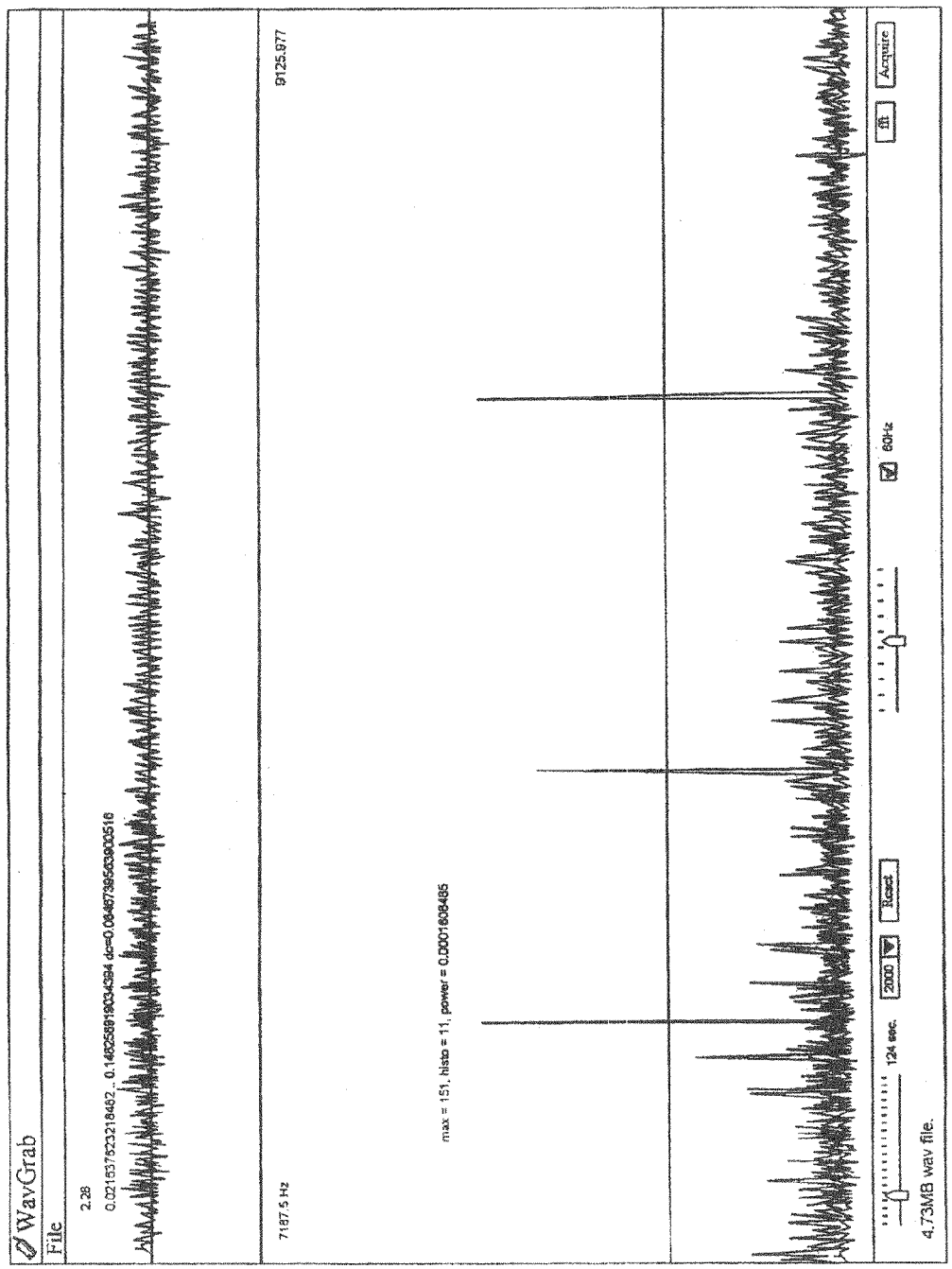
Figure 24:
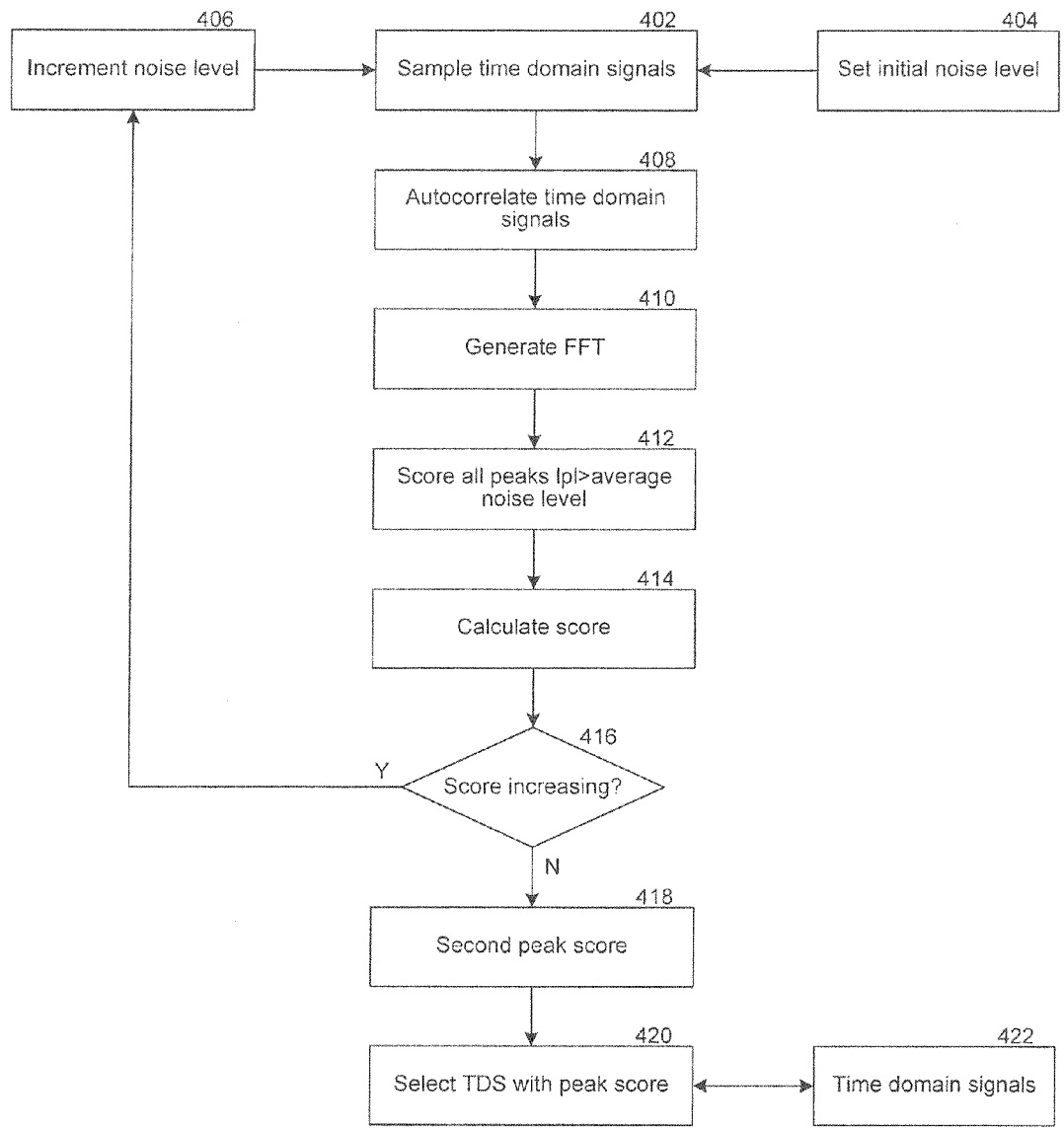
Figure 25A:
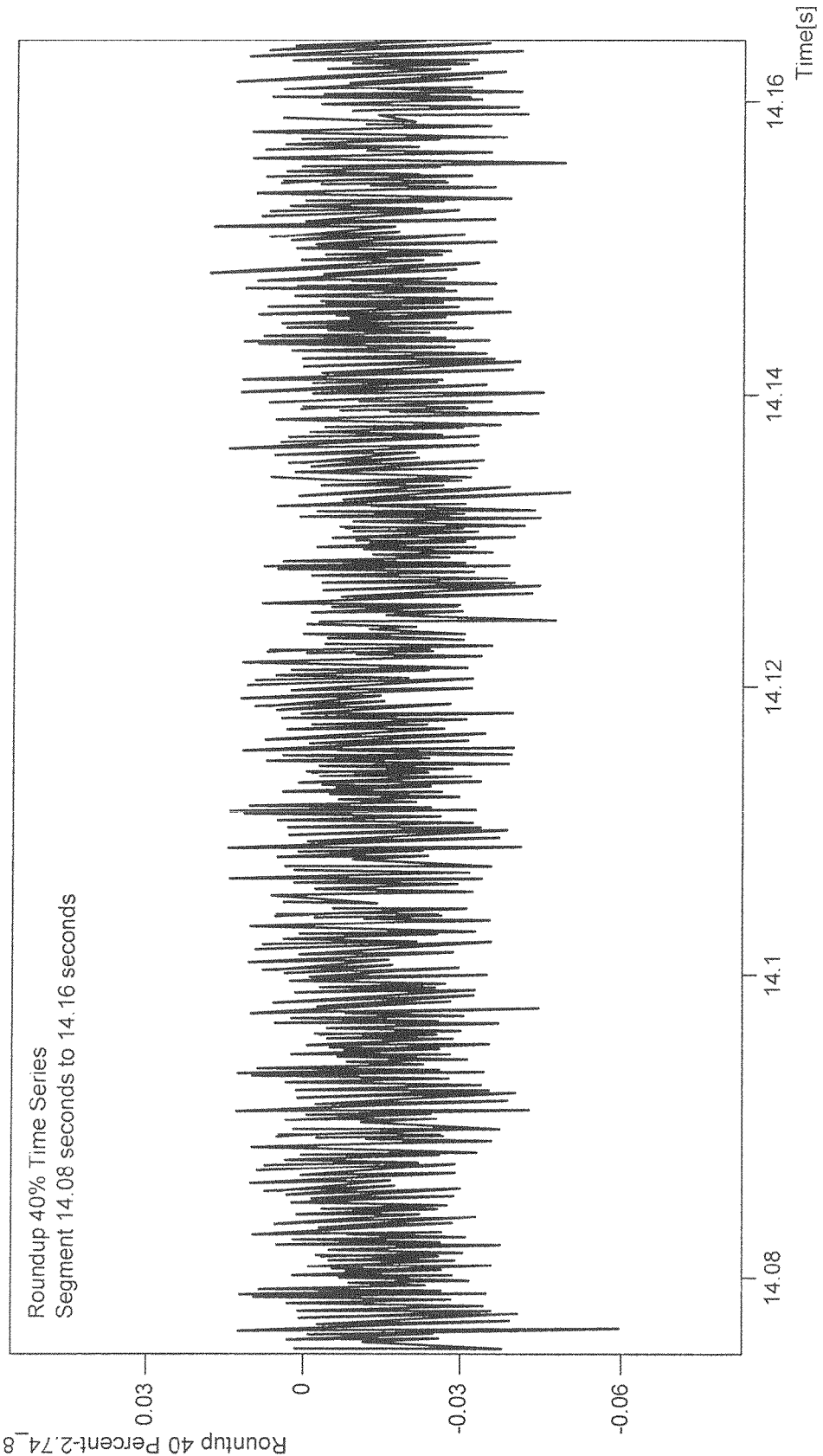
Figure 25B:
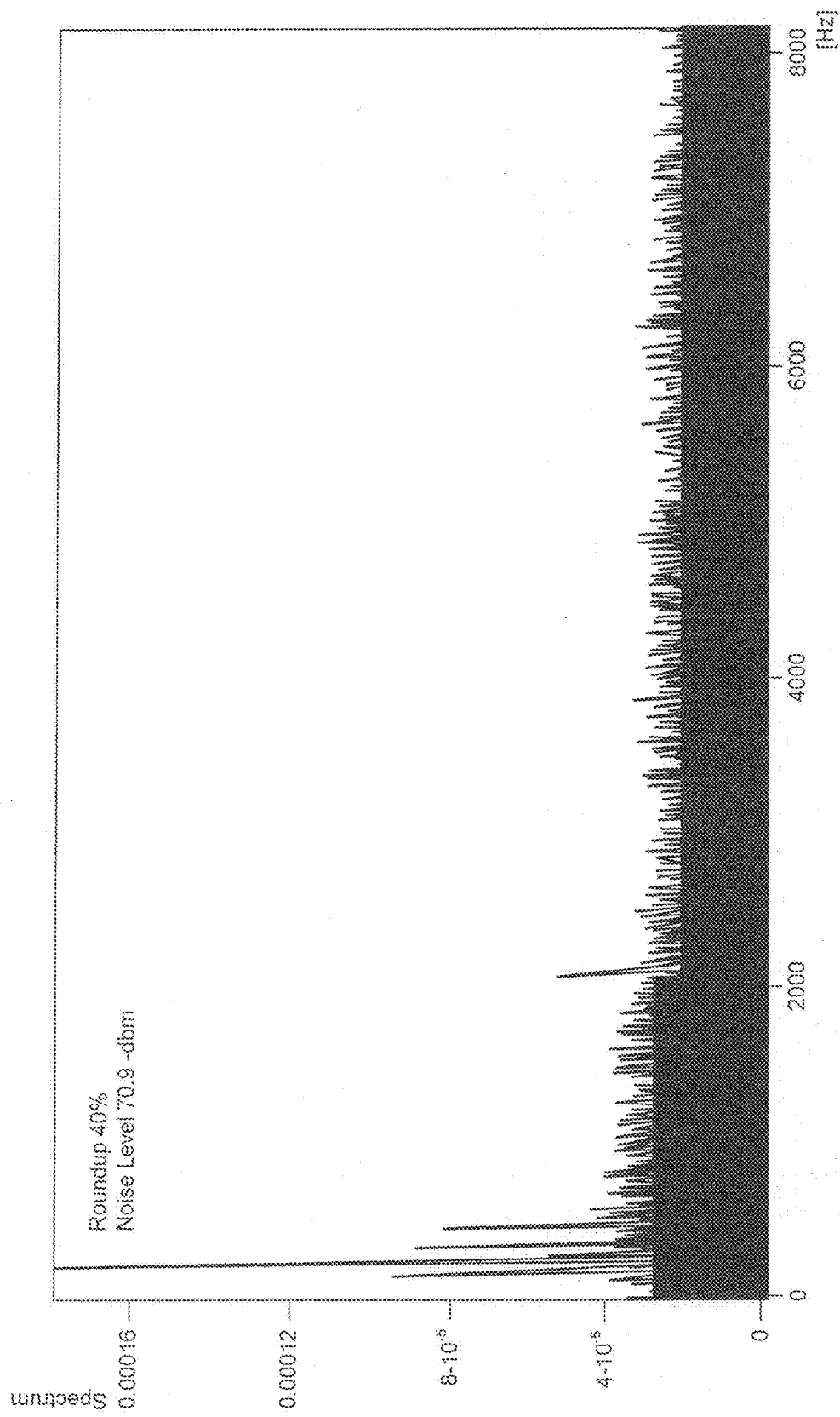
Figure 25C:
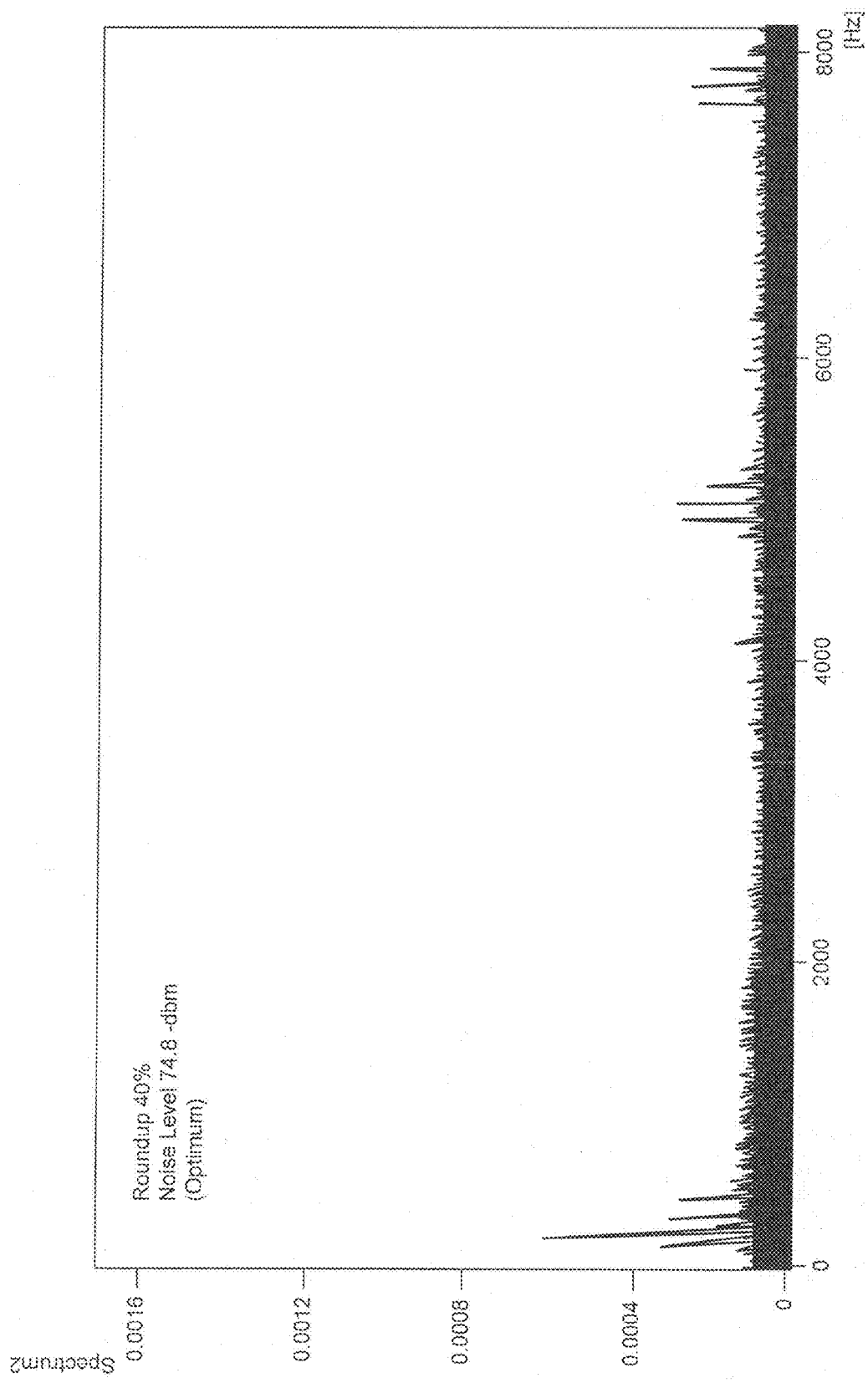
Figure 25D:
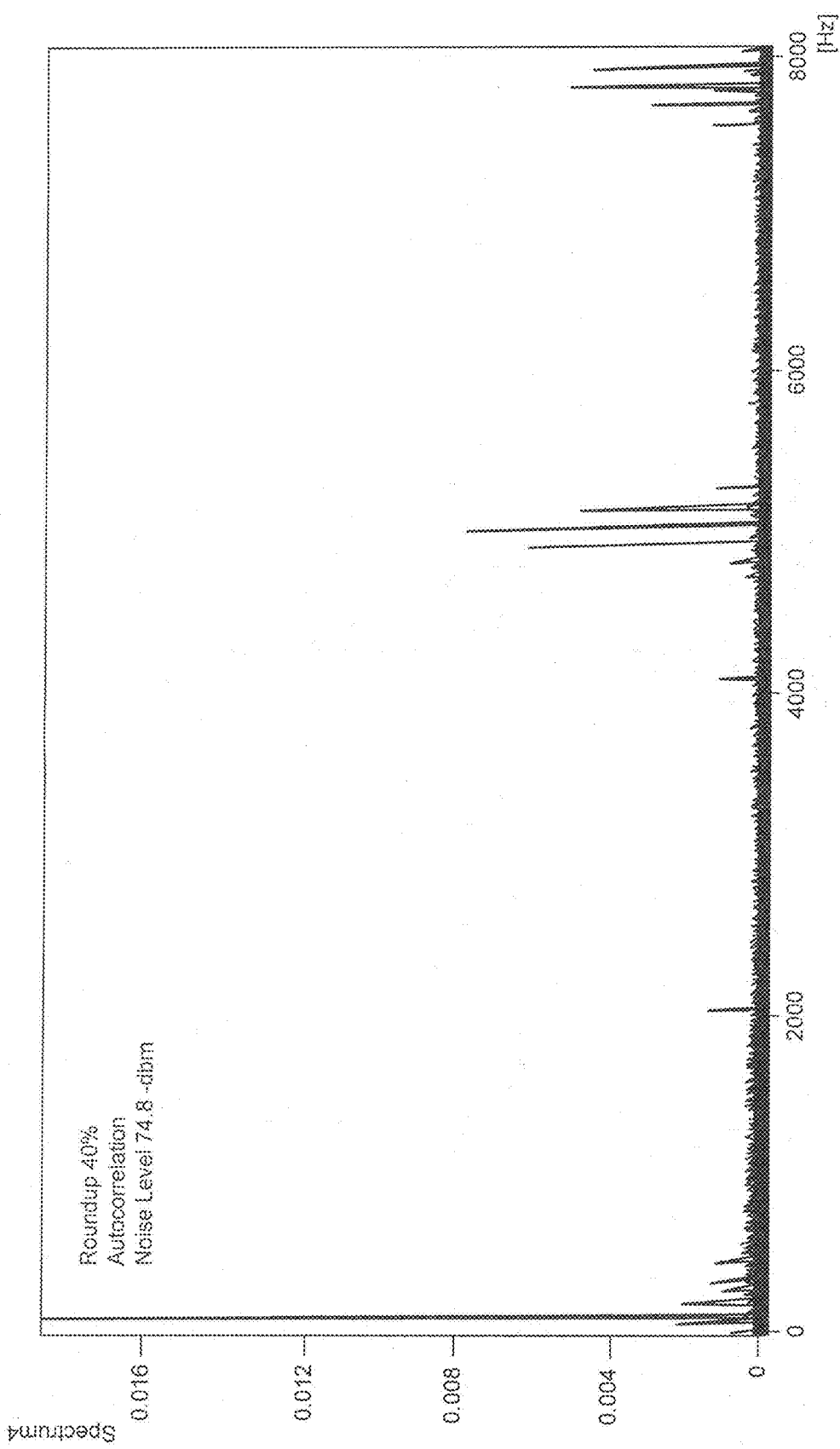
Figure 25E:
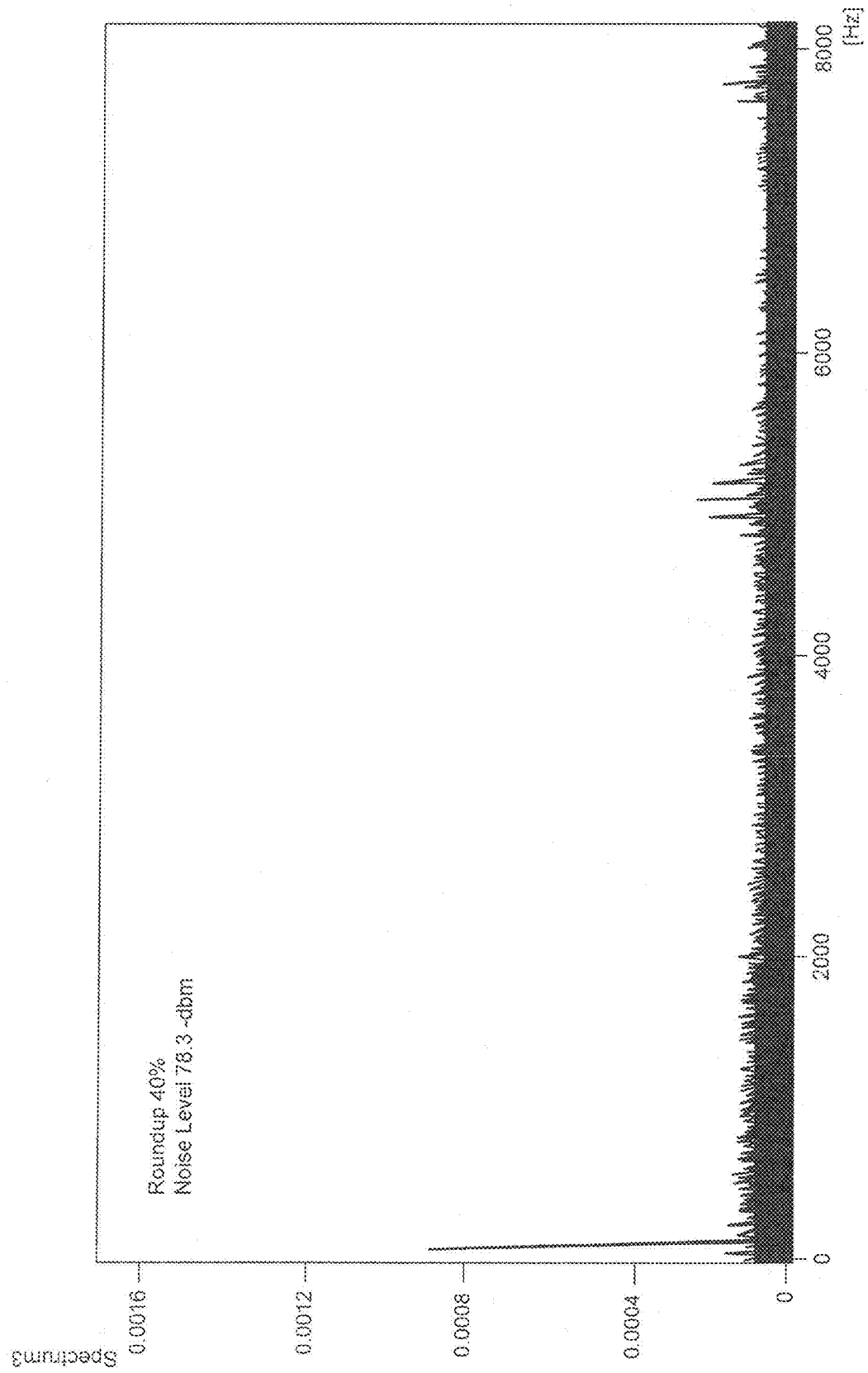
Figure 26:
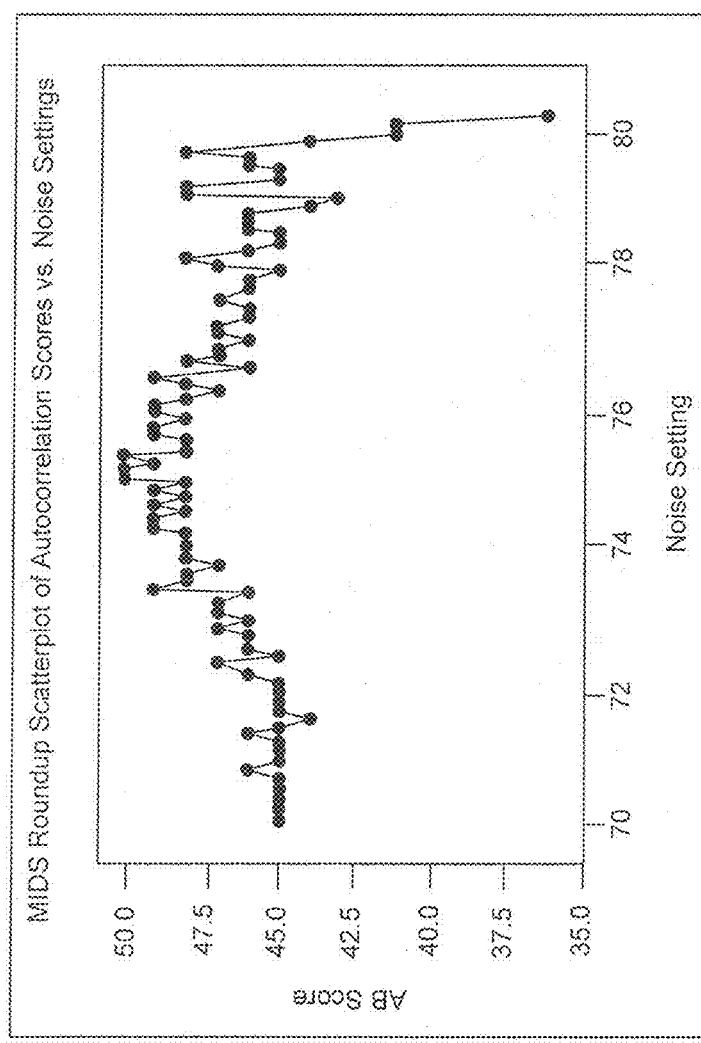
Figure 27:
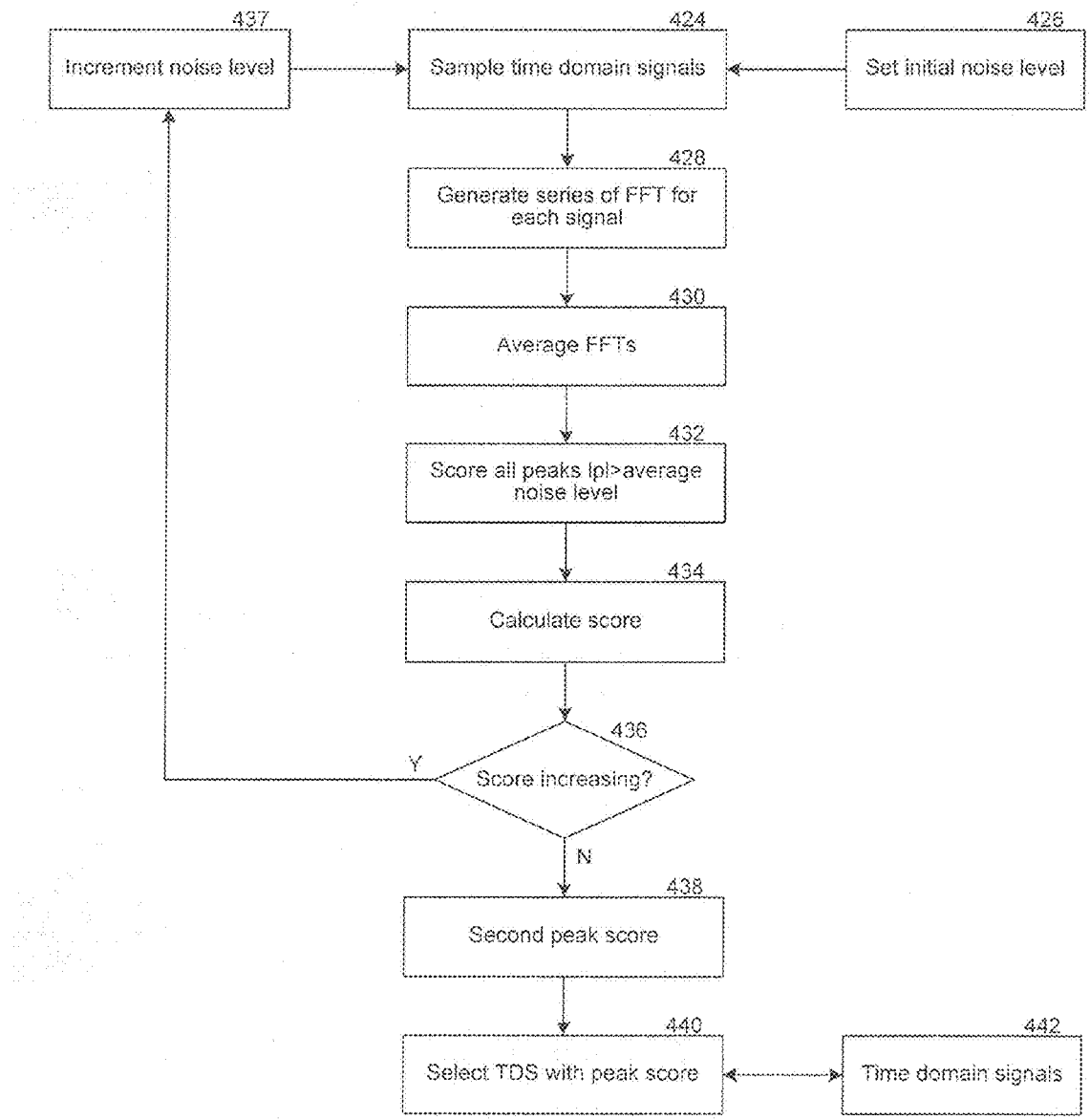
Figure 28A:
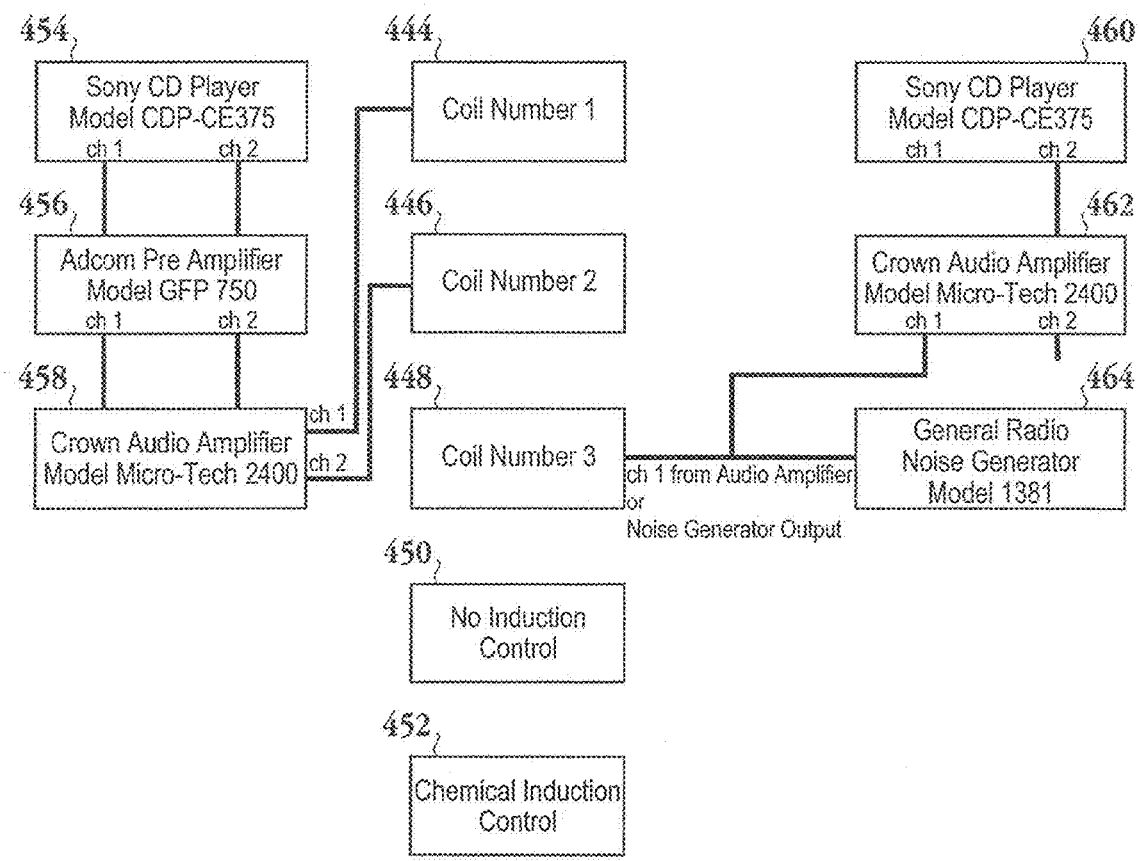
Figure 28B:
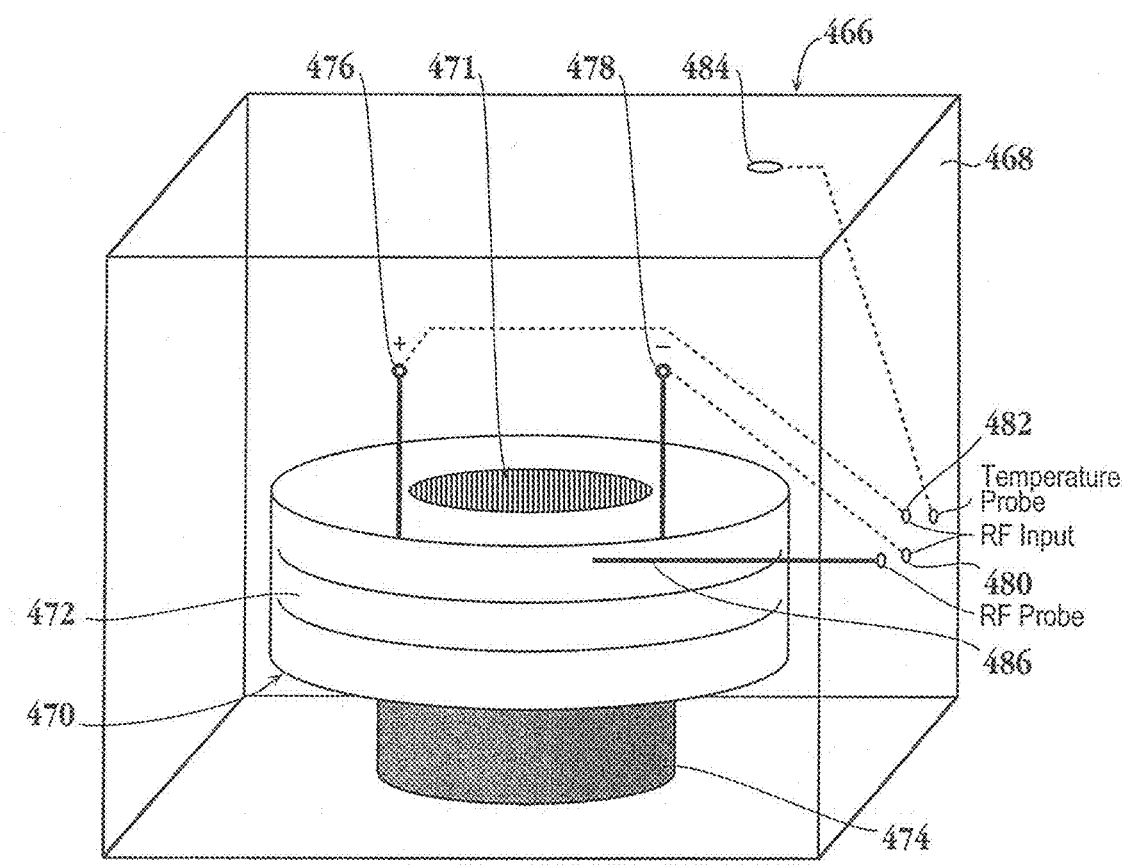
Figure 28C:
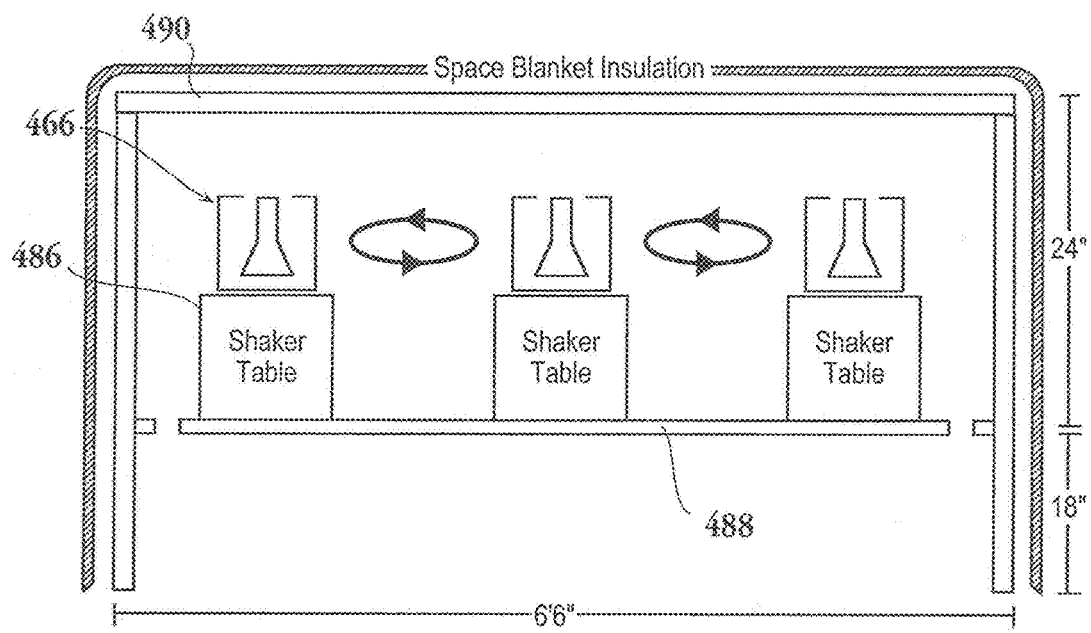
Figure 29A:
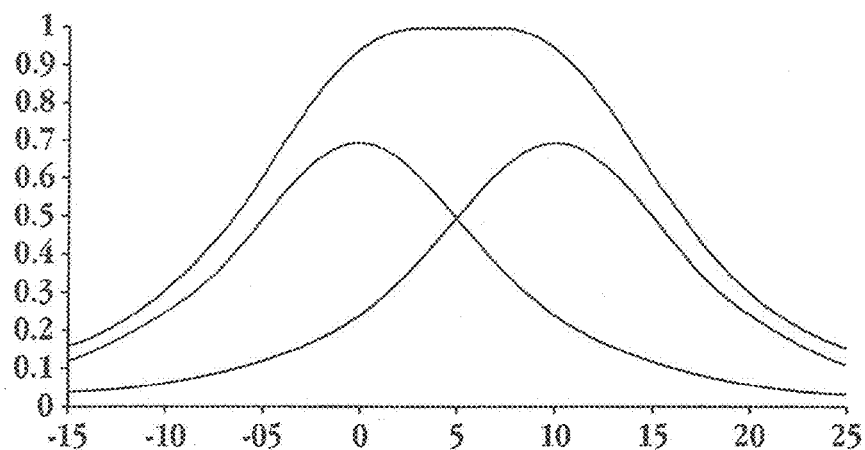
Figure 29B:
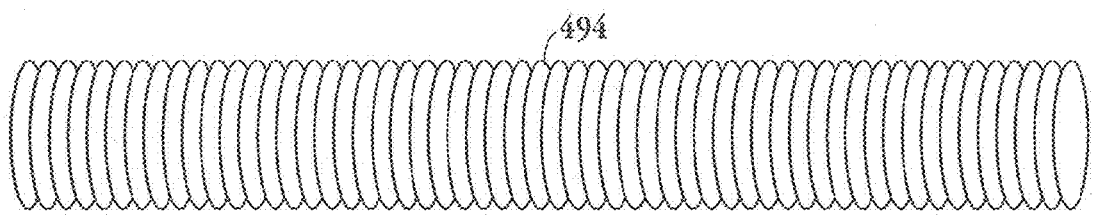
Figure 29C:
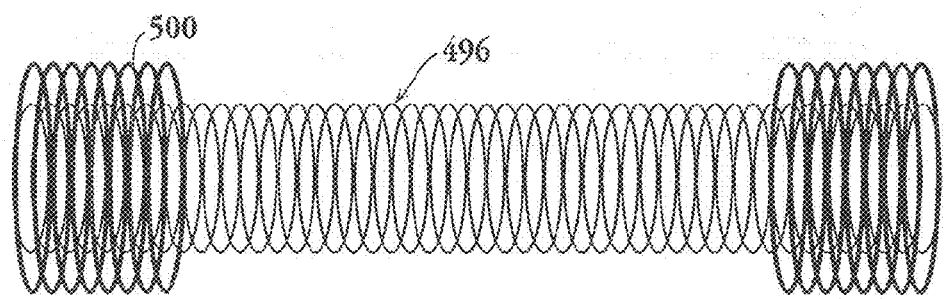
Figure 31:
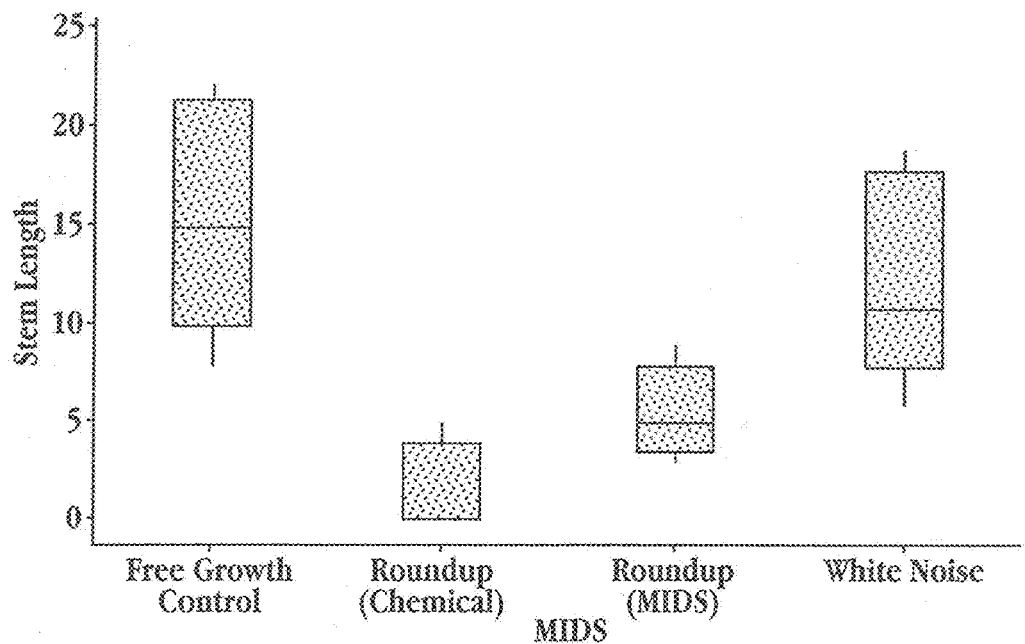
Figure 33:
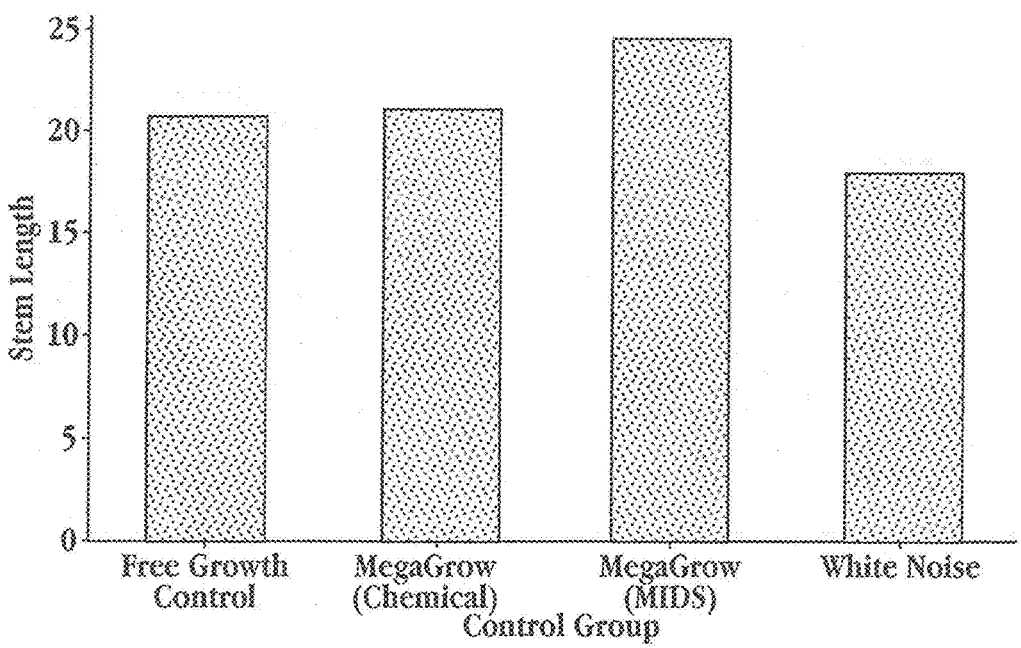
Figure 32A:
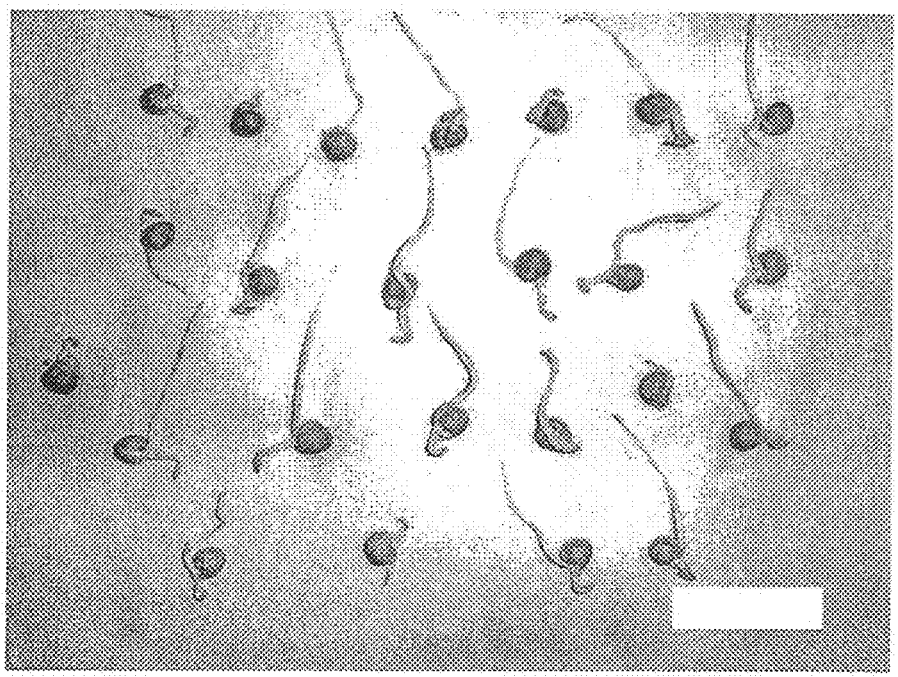
Figure 32B:
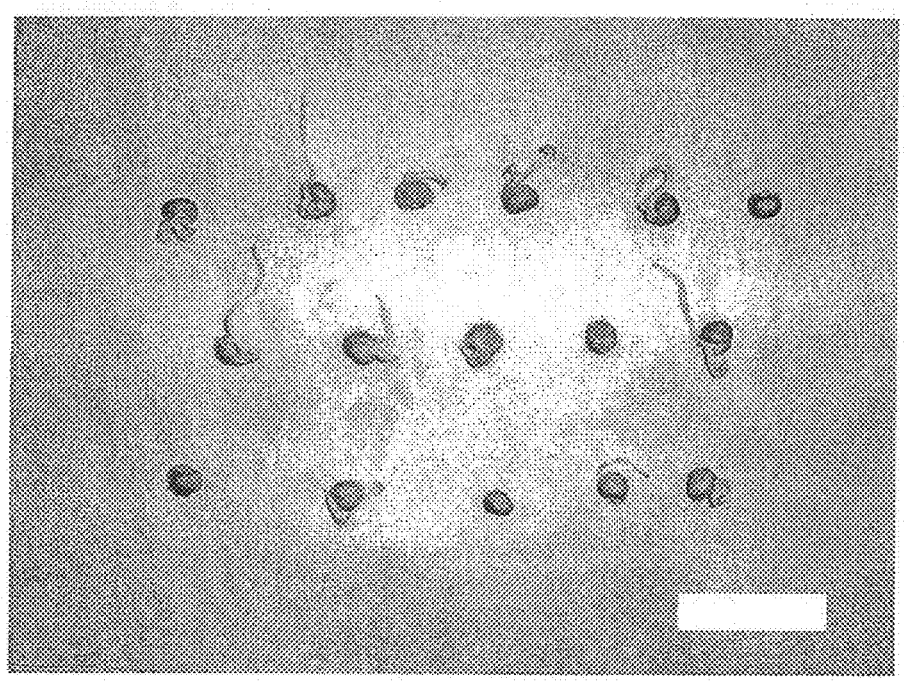

FIGS. 23A-23C are computer screen shots displaying a user interface for generating and displaying a spectral plot histogram;

FIG. 24 is a flow diagram of steps in identify optimal time-domain signals in accordance with a second embodiment of the method of the invention;

FIGS. 25A-25E shows (a portion of a time-domain signal for a sample containing 40% of an herbicide compound (25A), an FFT of autocorrelated time-domain signals from the sample in 25A, recorded at a noise levels of 70.9-dbm (25B), 74.8-dbm (25C and 25D), and 78.3-dbm (25E);

FIG. 26 is a plot of autocorrelation scores vs. noise setting for the sample in FIG. 25;

FIG. 27 is a flow diagram of steps in identify optimal time-domain signals in accordance with a third embodiment of the method of the invention;

FIG. 28A shows the transduction equipment layout in a typical transduction experiment; and FIGS. 28B and 28C show a transduction coil and container used in a typical transduction experiment (28B); and an arrangement of transduction coil on a shaker table (28C);

FIGS. 29A-29C show a plot of magnetic fields in a Helmholz coil transducer, as a function of position between the coils (29A); a solenoid transducer (29B), and a modified solenoid transducer (29C);

FIGS. 30A-30E show the response of AraL(+)-inducable green fluorescent protein in $E\ coli$ to various stimuli, including a MIDS AraL(+) signal;

FIG. 31 shows a boxplot of stem length in response to various stimuli, including a herbicide MIDS signal;

FIGS. 32A and 32B are photographs of sugar pea sprouts without (32A) and with (32B) exposure to a MIDS herbicide signal; and FIG. 33 shows the effect of various stimuli on stem length, including a growth stimulator MIDS signal, expressed as a boxplot of stem length in response to the stimuli.

Figure 34:
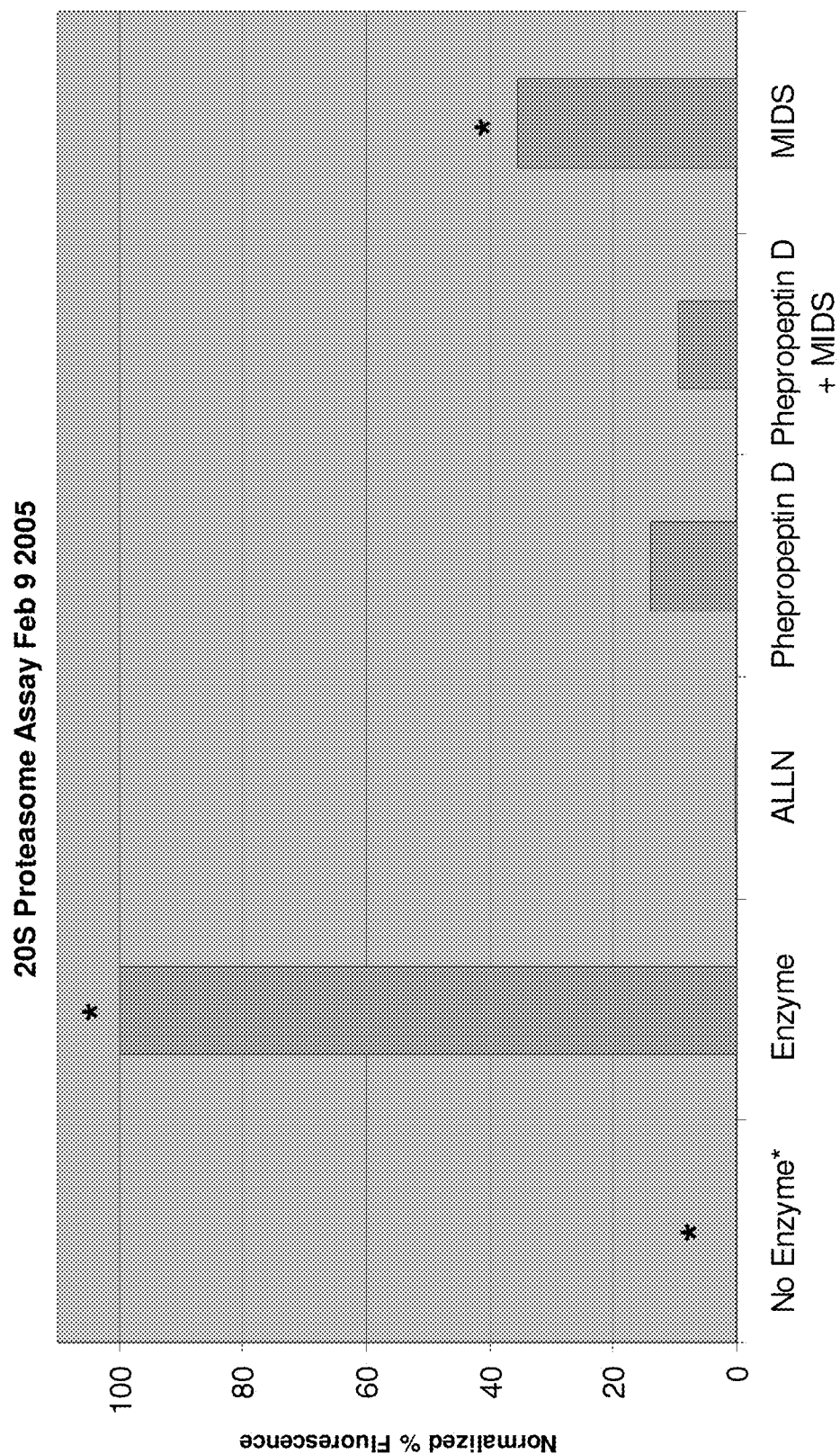

FIG. 34 is a bar graph for a 20S proteasome assay.

Discussion of any particular element or art, the most significant digit or digits in a reference number refer to the figure number in which that element is first introduced.

The headings provided herein are for convenience only and do not necessarily affect the scope or meaning of the claimed invention.

DETAILED DESCRIPTION

I. Definitions

The terms below have the following definitions unless indicated otherwise.

"Sample that exhibits molecular rotation" refers to a sample material, which may be in gaseous, liquid or solid form (other than a solid metal) in which one or more of the molecular compounds or atomic ions making up or present in the sample exhibit rotation.

"Magnetic shielding" refers to shielding that decreases, inhibits or prevents passage of magnetic flux as a result of the magnetic permeability of the shielding material.

"Electromagnetic shielding" refers to, e.g., standard Faraday electromagnetic shielding, or other methods to reduce passage of electromagnetic radiation.

"Time-domain signal" or "time-series signal" refers to a signal with transient signal properties that change over time.

"Sample-source radiation" refers to magnetic flux or electromagnetis flux emissions resulting from molecular motion of a sample, such as the rotation of a molecular dipole in a magnetic field.

"Gaussian noise" means random noise having a Gaussian power distribution. "Stationary white Gaussian noise" means random Gaussian noise that has no predictable future components. "Structured noise" may contain a logarithmic characteristic which shifts energy from one region of the spectrum to another, or it may be designed to provide a random time element while the amplitude remains constant. These two represent pink and uniform noise, as compared to truly random noise which has no predictable future component. "Uniform noise" means noise having a constant amplitude.

"Frequency-domain spectrum" refers to a Fourier frequency plot of a time-domain signal.

"Spectral components" refer to singular or repeating qualities within a time-domain signal that can be measured in the frequency, amplitude, and/or phase domains. Spectral components will typically refer to signals present in the frequency domain.

"Similar sample," with reference to a first sample, refers to the same sample or a sample having substantially the same sample components as the first sample.

"Faraday cage" refers to an electromagnetic shielding configuration that provides an electrical path to ground for unwanted electromagnetic radiation, thereby quieting an electromagnetic environment.

A "spectral-features score" refers to a score based on the number and/or amplitude of agent-specific spectral peaks observed over a selected low-frequency range, e.g., DC to 1 kHz or DC to 8 kHz, in a time-domain signal recorded for an agent or sample that has been processed by a suitable method, such as one of the three methods described herein, to reveal identifiable spectral features that are specific to the agent or sample.

An "optimized agent-specific time-domain signal" refers to a time-domain signal having a maximum or near-maximum spectral-features score.

II. Apparatus for Producing and Processing Low-Frequency Time-Domain Signals

Described in detail below is a system and method for detecting, processing, and presenting low frequency electromagnetic emissions or signals of a sample of interest. In one embodiment, a known white or Gaussian noise signal is introduced to the sample. The Gaussian noise is configured to permit the electromagnetic emissions from the sample to be sufficiently detected by a signal detection system. Sets of detected signals are processed together to ensure repeatability and statistical relevance. The resulting emission pattern or spectrum can be displayed, stored, and/or identified as a particular substance.

Some embodiments of the present invention describe signals for use with a transducing system for producing compound-specific electromagnetic waves that can act on target systems placed in the field of the waves, and methods of producing such signals. Other embodiments, relate to generating and distributing such signals.

The following description provides specific details for a thorough understanding of, and enabling description for, embodiments of the invention. However, one skilled in the art will understand that the invention may be practiced without these details. In other instances, well-known structures and functions have not been shown or described in detail to avoid unnecessarily obscuring the description of embodiments of the invention.

As explained in detail below, embodiments of the present invention are directed to providing an apparatus and method for the repeatable detection and recording of low-threshold molecular electromagnetic signals for later, remote use. A magnetically shielded faraday cage shields the sample material and detection apparatus from extraneous electromagnetic signals. Within the magnetically shielded faraday cage, a coil injects white or Gaussian noise, a nonferrous tray holds the sample, and a gradiometer detects low-threshold molecular electromagnetic signals. The apparatus further includes a superconducting quantum interference device ("SQUID") and a preamplifier.

The apparatus is used by placing a sample within the magnetically shielded faraday, cage in close proximity to the noise coil and gradiometer. White noise is injected through the noise coil and modulated until the molecular electromagnetic signal is enhanced through stochastic resonance. The enhanced molecular electromagnetic signal, shielded from external interference by the faraday cage and the field generated by the noise coil, is then detected and measured by the gradiometer and SQUID. The signal is then amplified and transmitted to any appropriate recording or measuring equipment.

Figure 1:
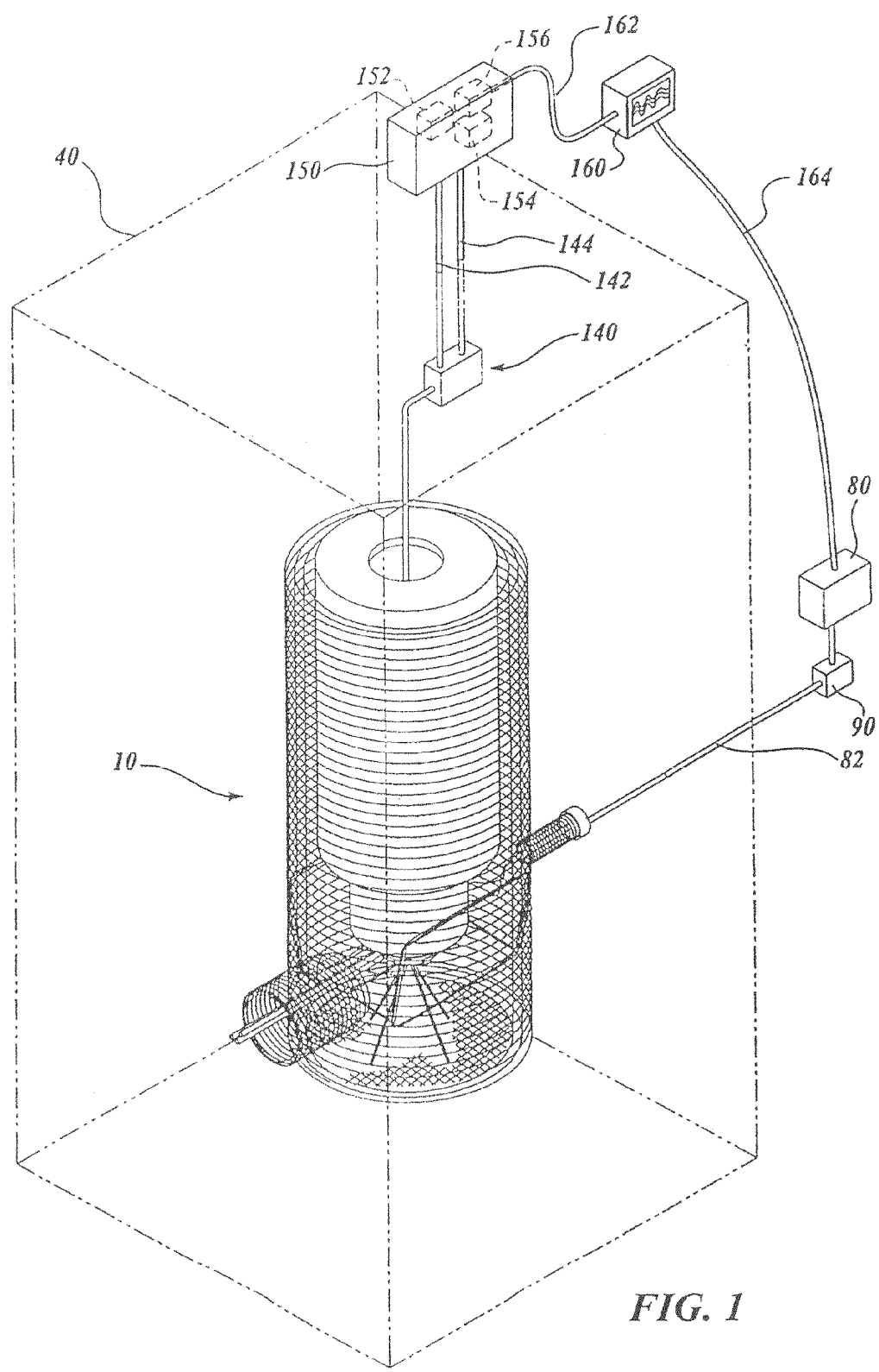
FIG. 1 is an isometric view of one embodiment of a molecular electromagnetic signaling detection apparatus formed in accordance with one embodiment of the present invention.

Referring to FIG. 1, there is shown a shielding structure 10 which includes, in an outer to inner direction, a conductive wire cage 16 which is a magnetic shield and inner conductive wire cages 18 and 20 which provide electromagnetic shielding. In another embodiment, the outer magnetic shield is formed of a solid aluminum plate material having an aluminum-nickel alloy coating, and the electromagnetic shielding is provided by two inner wall structures, each formed of solid aluminum.

Figure 2:
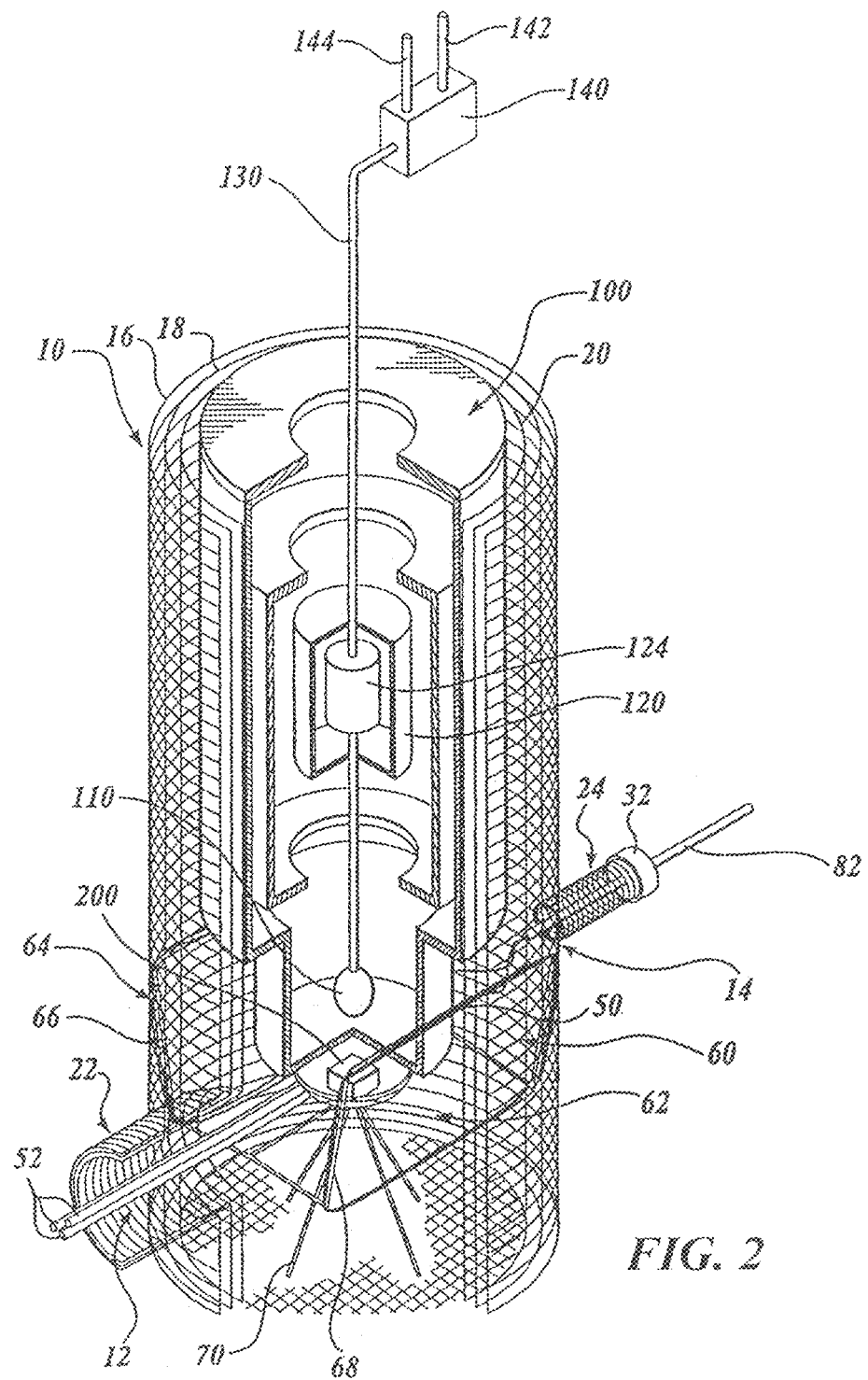
FIG. 2 is an enlarged, detail view of the faraday cage and its contents shown in FIG. 1.

Referring to FIG. 2, the faraday cage 10 is open at the top, and includes side openings 12 and 14. The faraday cage 10 is further comprised of three copper mesh cages 16, 18 and 20, nestled in one another. Each of the copper mesh cages 16, 18 and 20 is electrically isolated from the other cages by dielectric barriers (not shown) between each cage.

Figure 3:
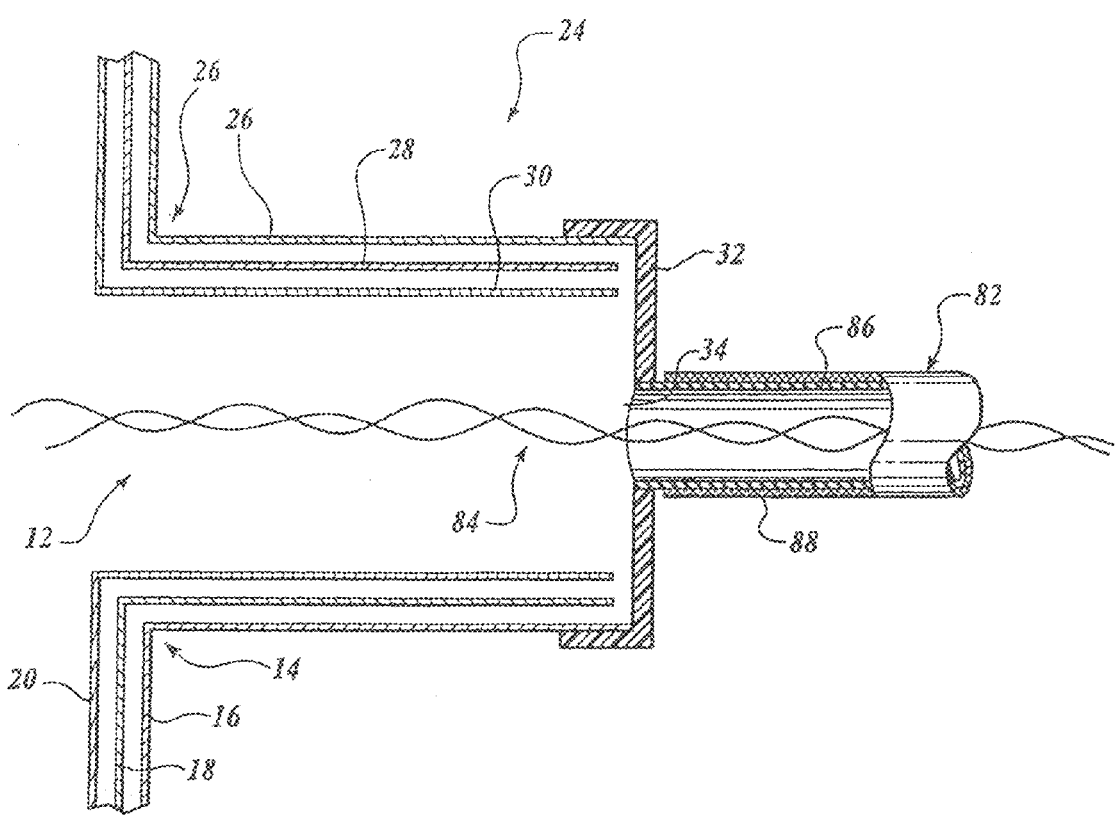
FIG. 3 is an enlarged, cross sectional view of one of the attenuation tubes shown in FIGS. 1 and 2.

Side openings 12 and 14 further comprise attenuation tubes 22 and 24 to provide access to the interior of the faraday cage 10 while isolating the interior of the cage from external sources of interference. Referring to FIG. 3, attenuation tube 24 is comprised of three copper mesh tubes 26, 28 and 30, nestled in one another. The exterior copper mesh cages 16, 18 and 20 are each electrically connected to one of the copper mesh tubes 26, 28 and 30, respectively. Attenuation tube 24 is further capped with cap 32, with the cap having hole 34. Attenuation tube 22 is similarly comprised of copper mesh tubes 26, 28 and 30, but does not include cap 32.

Referring again to FIG. 2, a low-density nonferrous sample tray 50 is mounted in the interior of the faraday cage 10. The sample tray 50 is mounted so that it may be removed from the faraday cage 10 through the attenuation tube 22 and side opening 12. Three rods 52, each of which is greater in length than the distance from the center vertical axis of the faraday cage 10 to the outermost edge of the attenuation tube 22, are attached to the sample tray 50. The three rods 52 are adapted to conform to the interior curve of the attenuation tube 22, so that the sample tray 50 may be positioned in the center of the faraday cage 10 by resting the rods in the attenuation tube. In the illustrated embodiment, the sample tray 50 and rods 52 are made of glass fiber epoxy. It will be readily apparent to those skilled in the art that the sample tray 50 and rods 52 may be made of other nonferrous materials, and the tray may be mounted in the faraday cage 10 by other means, such as by a single rod.

Referring again to FIG. 2, mounted within the faraday cage 10 and above the sample tray 50 is a cryogenic dewar 100. In the disclosed embodiment, the dewar 100 is adapted to fit within the opening at the top of faraday cage 10 and is a Model BMD-6 Liquid Helium Dewar manufactured by Tristan Technologies, Inc. The dewar 100 is constructed of a glass-fiber epoxy composite. A gradiometer 110 with a very narrow field of view is mounted within the dewar 100 in position so that its field of view encompasses the sample tray 50. In the illustrated embodiment, the gradiometer 110 is a first order axial detection coil, nominally 1 centimeter in diameter, with a 2% balance, and is formed from a superconductor. The gradiometer can be any form of gradiometer excluding a planar gradiometer. The gradiometer 110 is connected to the input coil of one low temperature direct current superconducting quantum interference device ("SQUID") 120. In the disclosed embodiment, the SQUID is a Model LSQ/20 LTS dc SQUID manufactured by Tristan Technologies, Inc. It will be recognized by those skilled in the art that high temperature or alternating current SQUIDs can be used without departing from the spirit and scope of the invention. In an alternative embodiment, the SQUID 120 includes a noise suppression coil 124.

The disclosed combination of gradiometer 110 and SQUID 120 have a sensitivity of 5 microTesla/Hz when measuring magnetic fields.

The output of SQUID 120 is connected to a Model SP Cryogenic Cable 130 manufactured by Tristan Technologies, Inc. The Cryogenic Cable 130 is capable of withstanding the temperatures within and without the dewar 100 and transfers the signal from the SQUID 120 to Flux-Locked Loop 140, which is mounted externally to the faraday cage 10 and dewar 100. The Flux-Locked Loop 140 in the disclosed embodiment is an iFL-301-L Flux-Locked Loop manufactured by Tristan Technologies, Inc.

Referring to FIG. 1, the Flux Locked Loop 140 further amplifies and outputs the signal received from the SQUID 120 via high-level output circuit 142 to an iMC-303 iMAG® SQUID controller 150. The Flux-Locked Loop 140 is also connected via a model CC-60 six-meter fiber-optic composite connecting cable 144 to the SQUID controller 150. The fiber-optic connecting cable 144 and SQUID controller 150 are manufactured by Tristan Technologies, Inc. The controller 150 is mounted externally to the magnetic shielding cage 40. The fiber-optic connecting cable 144 carriers control signals from the SQUID controller 150 to the Flux Locked Loop 140, further reducing the possibility of electromagnetic interference with the signal to be measured. It will be apparent to those skilled in the art that other Flux-Locked Loops, connecting cables, and Squid controllers can be used without departing from the spirit and scope of the invention.

The SQUID controller 150 further comprises high resolution analog to digital converters 152, a standard GP-IB bus 154 to output digitalized signals, and BNC connectors 156 to output analog signals. In the illustrated embodiment, the BNC connectors are connected to a dual trace oscilloscope 160 through patch cord 162.

Referring to FIG. 2, a two-element Helmholtz transformer 60 is installed to either side of the sample tray 50 when the sample tray is fully inserted within the faraday cage 10. In the illustrated embodiment, the coil windings 62 and 64 of the Helmholtz transformer 60 are designed to operate in the direct current to 50 kilohertz range, with a center frequency of 25 kilohertz and self-resonant frequency of 8.8 megahertz. In the illustrated embodiment, the coil windings 62 and 64 are generally rectangular in shape and are approximately 8 inches tall by 4 inches wide. Other Helmholtz coil shapes may be used but should be shaped and sized so that the gradiometer 110 and sample tray 50 are positioned within the field produced by the Helmholtz coil. Each of coil windings 62 and 64 is mounted on one of two low-density nonferrous frames 66 and 68. The frames 66 and 68 are hingedly connected to one another and are supported by legs 70. Frames 66 and 68 are slidably attached to legs 70 to permit vertical movement of the frames in relation to the lower portion of dewar 100. Movement of the frames permits adjustment of the coil windings 62 and 64 of the Helmholtz transformer 60 to vary the amplitude of white noise received at gradiometer 110. The legs 70 rest on or are epoxied onto the bottom of the faraday cage 10. In the illustrated embodiment, the frames 66 and 68 and legs 70 are made of glass fiber epoxy. Other arrangements of transformers or coils may be used around the sample tray 50 without departing from the spirit and scope of the invention.

Figure 4:
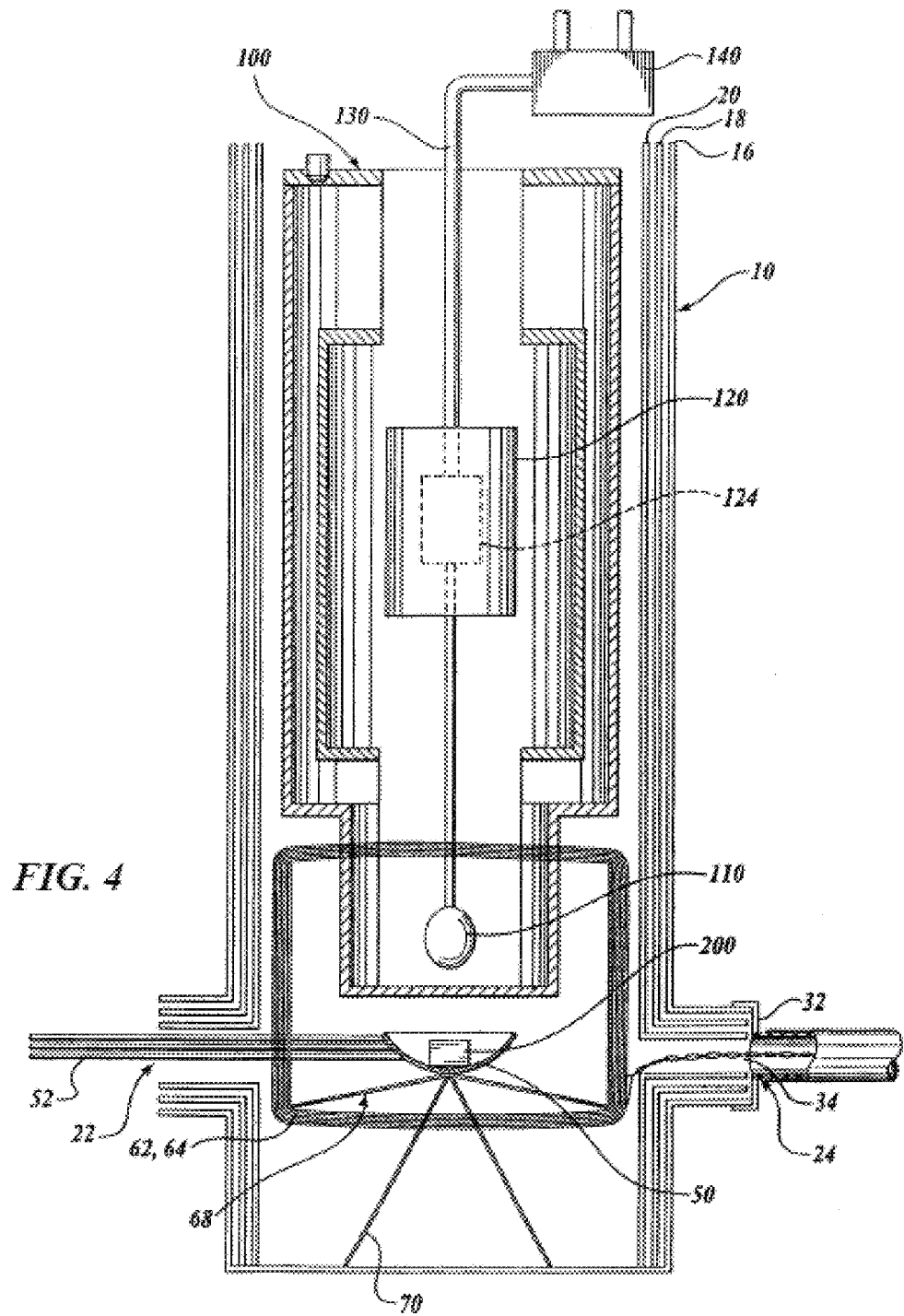
FIG. 4 is a cross-section view of the faraday cage and its contents shown in FIG. 2.

Referring to FIG. 4, there is shown a cross-sectional view of the faraday cage and its contents, showing windings 62 of Helmholtz transformer 60 in relation to dewar 100 and faraday cage 10. Note also in FIG. 4 the positioning of sample tray 50 and sample 200.

Figure 5:
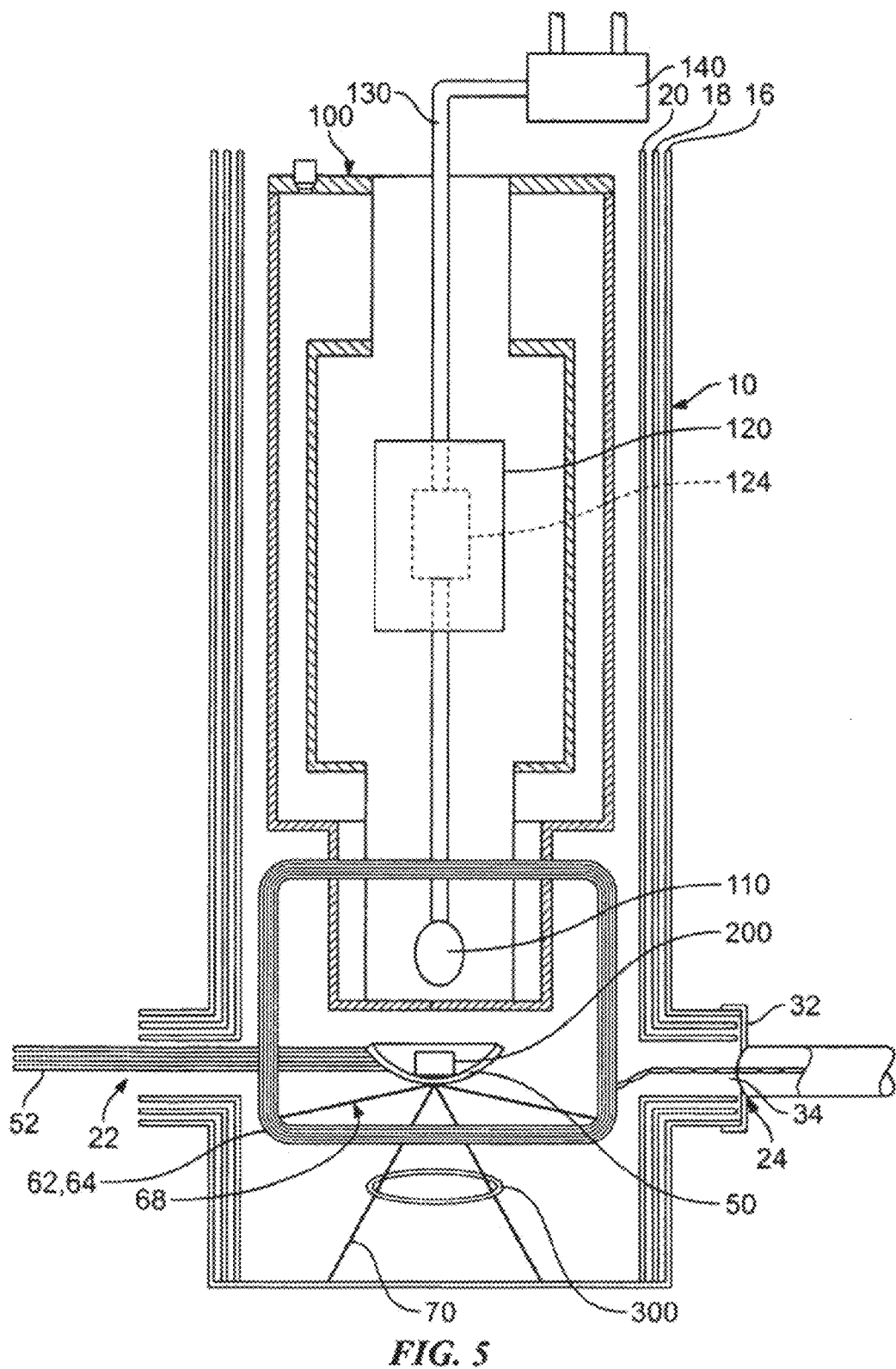
FIG. 5 is a cross-section view of an alternative embodiment of the invention shown in FIGS. 1 through 4.

Referring to FIG. 5, there is shown an alternative embodiment in which the Helmholtz coil windings 62 and 64 are fixed in a vertical orientation and an additional noise coil 300 is positioned below sample tray 50. The windings of the additional noise coil 300 are substantially perpendicular to the vertical windings 62 and 64 of Helmholtz transformer 60, and the windings of the additional noise coil 300 are thus substantially in parallel orientation to the bottom of faraday cage 10.

In this alternative embodiment, noise would be fed to noise coil 300 from an identical twisted pair wire (not shown) as that supplying the Helmholtz coil. The noise source would originate with the same noise generator used to supply noise to the Helmholtz coil. Noise would be sampled either at the noise generator via an additional noise output connection, or via a balanced splitter from an output connection to the noise generator. Attenuation of the noise signal at additional noise coil 300 would be through an adjustable RF signal attenuation circuit, of which many are available commercially, or via a suitable series of fixed value RF attenuation filters.

Figure 6:
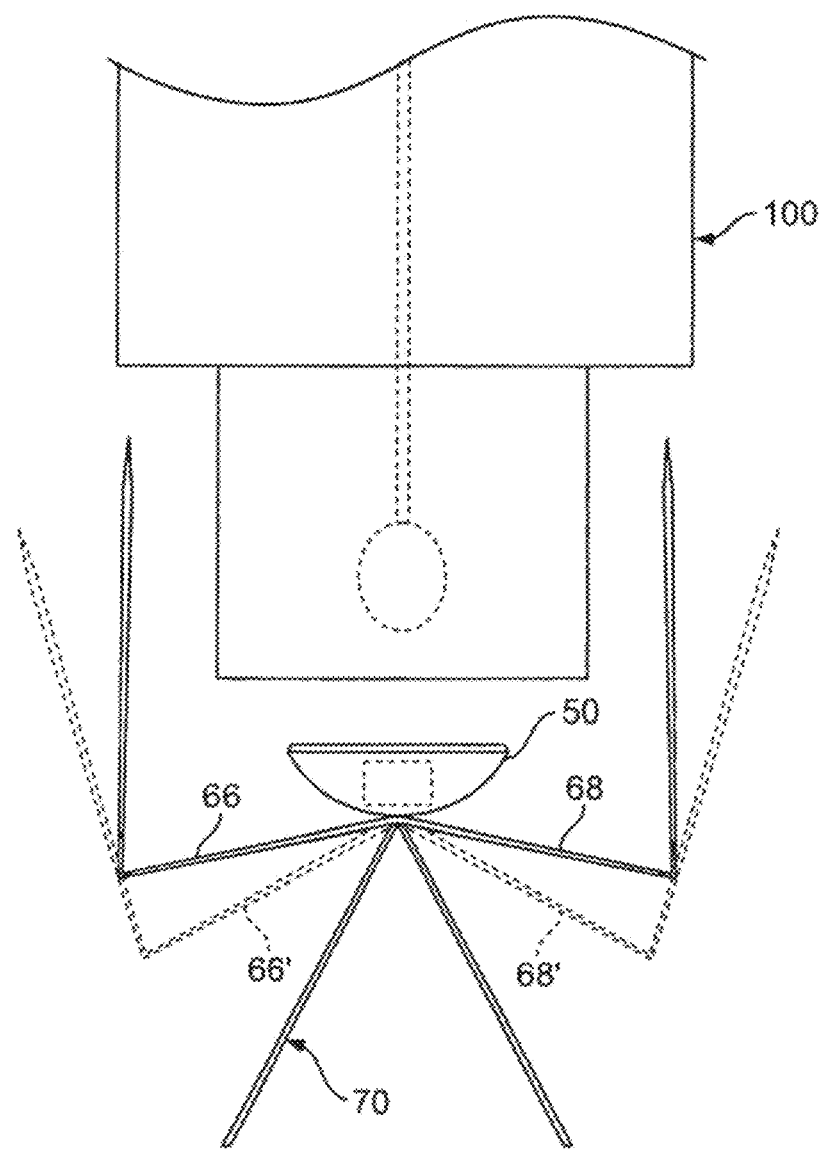
FIG. 6 is an enlarged, detail view of the frames supporting the coils of the Helmholtz transformer described herein.

Referring to FIG. 6, a detail of the frames supporting the coils of Helmholtz transformer 60 may be seen; the reference point of FIG. 6 is 90 degrees from the view of FIG. 4, and omits the faraday cage 10. Frames 66 and 68 are disposed to show the coil windings of the Helmholtz coil in a substantially vertical position and parallel to one another. Frames 66' and 68' illustrate the rotation of said frames about the axis of the hinged connection joining said frames, so as to dispose the coil windings of the Helmholtz transformer in an non-parallel relationship with one another.

Referring again to FIG. 1, an amplitude adjustable white noise generator 80 is external to magnetic shielding cage 40, and is electrically connected to the Helmholtz transformer 60 through filter 90 by electrical cable 82. Referring to FIG. 3, cable 82 is run through side opening 12, attenuation tube 24, and through cap 32 via hole 34. Cable 82 is a co-axial cable further comprising a twisted pair of copper conductors 84 surrounded by interior and exterior magnetic shielding 86 and 88, respectively. In other embodiments, the conductors can be any nonmagnetic electrically conductive material, such as silver or gold. The interior and exterior magnetic shielding 86 and 88 terminates at cap 32, leaving the twisted pair 84 to span the remaining distance from the end cap to the Helmholtz transformer 60 shown in FIG. 1. The interior magnetic shielding 86 is electrically connected to Faraday cage 16 through cap 32, while the exterior magnetic shielding is electrically connected to the magnetically shielded cage 40 shown in FIG. 1.

Referring to FIG. 1, the white noise generator 80 can generate nearly uniform noise across a frequency spectrum from zero to 100 kilohertz. In the illustrated embodiment, the filter 90 filters out noise above 50 kilohertz, but other frequency ranges may be used without departing from the spirit and scope of the invention.

White noise generator 80 is also electrically connected to the other input of dual trace oscilloscope 160 through patch cord 164.

Referring to FIGS. 1, 2 and 3, a sample of the substance 200 to be measured is placed on the sample tray 50 and the sample tray is placed within the faraday cage 10. In the first embodiment, the white noise generator 80 is used to inject white noise through the Helmholtz transformer 60. The noise signal creates an induced voltage in the gradiometer 110. The induced voltage in the gradiometer 110 is then detected and amplified by the SQUID 120, the output from the SQUID is further amplified by the flux locked loop 140 and sent to the SQUID controller 150, and then sent to the dual trace oscilloscope 160. The dual trace oscilloscope 160 is also used to display the signal generated by white noise generator 80.

The white noise signal is adjusted by altering the output of the white noise generator 80 and by rotating the Helmholtz transformer 60 around the sample 200, shown in FIG. 2. Rotation of the Helmholtz transformer 60 about the axis of the hinged connection of frames 66 and 68 alters its phasing with respect to the gradiometer 110. Depending upon the desired phase alteration, the hinged connection of frames 66 and 68 permits windings 62 and 64 to remain parallel to one another while rotating approximately 30 to 40 degrees around sample tray 50. The hinged connection also permits windings 62 and 64 to rotate as much as approximately 60 degrees out of parallel, in order to alter signal phasing of the field generated by Helmholtz transformer 60 with respect to gradiometer 110. The typical adjustment of phase will include this out-of-parallel orientation, although the other orientation may be preferred in certain circumstances, to accommodate an irregularly shaped sample 200, for example. Noise is applied and adjusted until the noise is 30 to 35 decibels above the molecular electromagnetic emissions sought to be detected. At this noise level, the noise takes on the characteristics of the molecular electromagnetic signal through the well-known phenomenon of stochastic resonance. The stochastic product sought is observed when the oscilloscope trace reflecting the signal detected by gradiometer 110 varies from the trace reflecting the signal directly from white noise generator 80. In alternative embodiments, the signal can be recorded and or processed by any commercially available equipment.

In an alternative embodiment, the method of detecting the molecular electromagnetic signals further comprises injecting noise 180.degree. out of phase with the original noise signal applied at the Helmholz transformer 60 through the noise suppression coil 124 of the SQUID 120. The stochastic product sought can then be observed when the oscilloscope trace reflecting the signal detected by gradiometer 110 becomes non-random.

Regardless of how the noise is injected and adjusted, the stochastic product can also be determined by observing when an increase in spectral peaks occurs. The spectral peaks can be observed as either a line plot on oscilloscope 160 or as numerical values, or by other well known measuring devices.

Embodiments of the present invention provide a method and apparatus for detecting extremely low-threshold molecular electromagnetic signals without external interference. They further provide for the output of those signals in a format readily usable by a wide variety of signal recording and processing equipment.

Figure 7:
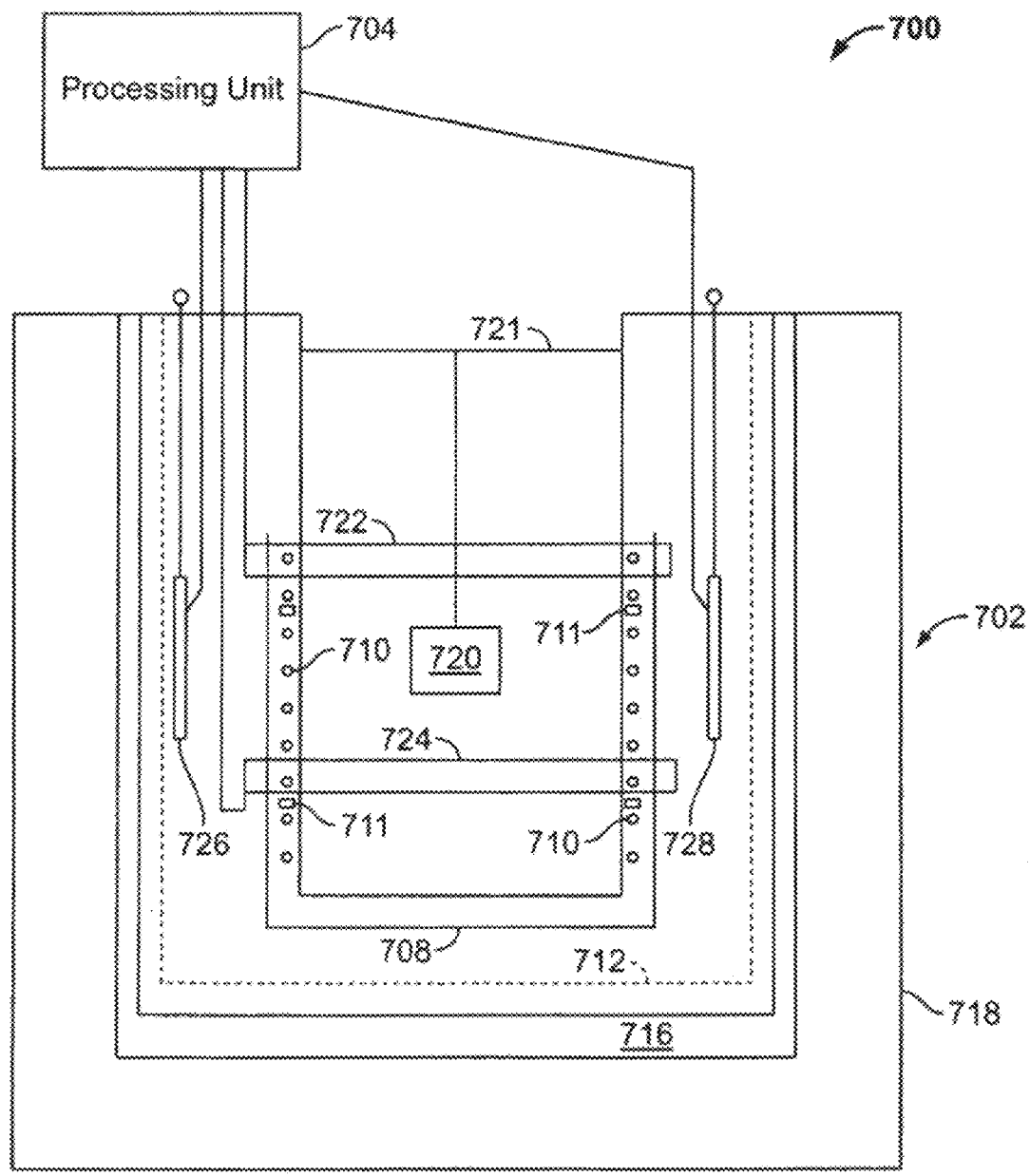
FIG. 7 is a diagram of an alternative electromagnetic emission detection system.

Referring now to FIG. 7, an alternative embodiment to the molecular electromagnetic emission detection and processing system of the above Figures is shown. A system 700 includes a detection unit 702 coupled to a processing unit 704. Although the processing unit 704 is shown external to the detection unit 702, at least a part of the processing unit can be located within the detection unit.

The detection unit 702, which is shown in a cross-sectional view in FIG. 7, includes a plurality of components nested or concentric with each other. A sample chamber or faraday cage 706 is nested within a metal cage 708. Each of the sample chamber 706 and the metal cage 708 can be comprised of aluminum material. The sample chamber 706 can be maintained in a vacuum and may be temperature controlled to a preset temperature. The metal cage 708 is configured to function as a low pass filter.

Between the sample chamber 706 and the metal cage 708 and encircling the sample chamber 706 are a set of parallel heating coils or elements 710. One or more temperature sensor 711 is also located proximate to the heating elements 710 and the sample chamber 706. For example, four temperature sensors may be positioned at different locations around the exterior of the sample chamber 706. The heating elements 710 and the temperature sensor(s) 711 may be configured to maintain a certain temperature inside the sample chamber 706.

A shield 712 encircles the metal cage 708. The shield 712 is configured to provide additional magnetic field shielding or isolation for the sample chamber 706. The shield 712 can be comprised of lead or other magnetic shielding materials. The shield 712 is optional when sufficient shielding is provided by the sample chamber 706 and/or the metal cage 708.

Surrounding the shield 712 is a cryogen layer 716 with G10 insulation. The cryogen may be liquid helium. The cryogen layer 716 (also referred to as a cryogenic Dewar) is at an operating temperature of 4 degrees Kelvin. Surrounding the cryogen layer 716 is an outer shield 718. The outer shield 718 is comprised of nickel alloy and is configured to be a magnetic shield. The total amount of magnetic shielding provided by the detection unit 702 is approximately −100 dB, −100 dB, and −120 dB along the three orthogonal planes of a Cartesian coordinate system.

The various elements described above are electrically isolated from each other by air gaps or dielectric barriers (not shown). It should also be understood that the elements are not shown to scale relative to each other for ease of description.

A sample holder 720 can be manually or mechanically positioned within the sample chamber 706. The sample holder 720 may be lowered, raised, or removed from the top of the sample chamber 706. The sample holder 720 is comprised of a material that will not introduce Eddy currents and exhibits little or no inherent molecular rotation. As an example, the sample holder 720 can be comprised of high quality glass or Pyrex.

The detection unit 702 is configured to handle solid, liquid, or gas samples. Various sample holders may be utilized in the detection unit 702. For example, depending on the size of the sample, a larger sample holder may be utilized. As another example, when the sample is reactive to air, the sample holder can be configured to encapsulate or form an airtight seal around the sample. In still another example, when the sample is in a gaseous state, the sample can be introduced inside the sample chamber 706 without the sample holder 720. For such samples, the sample chamber 706 is held at a vacuum. A vacuum seal 721 at the top of the sample chamber 706 aids in maintaining a vacuum and/or accommodating the sample holder 720.

A sense coil 722 and a sense coil 724, also referred to as detection coils, are provided above and below the sample holder 720, respectively. The coil windings of the sense coils 722, 724 are configured to operate in the direct current (DC) to approximately 50 kilohertz (kHz) range, with a center frequency of 25 kHz and a self-resonant frequency of 8.8 MHz. The sense coils 722, 724 are in the second derivative form and are configured to achieve approximately 100% coupling. In one embodiment, the coils 722, 724 are generally rectangular in shape and are held in place by G10 fasteners. The coils 722, 724 function as a second derivative gradiometer.

Helmholtz coils 726 and 728 may be vertically positioned between the shield 712 and the metal cage 708, as explained herein. Each of the coils 726 and 728 may be raised or lowered independently of each other. The coils 726 and 728, also referred to as a white or Gaussian noise generation coils, are at room or ambient temperature. The noise generated by the coils 726, 728 is approximately 0.10 Gauss.

The degree of coupling between the emissions from the sample and the coils 722, 724 may be changed by repositioning the sample holder 720 relative to the coils 722, 724, or by repositioning one or both of the coils 726, 728 relative to the sample holder 720.

The processing unit 704 is electrically coupled to the coils 722, 724, 726, and 728. The processing unit 704 specifies the white or Gaussian noise to be injected by the coils 726, 728 to the sample. The processing unit 104 also receives the induced voltage at the coils 722, 724 from the sample's electromagnetic emissions mixed with the injected Gaussian noise.

Figure 8:
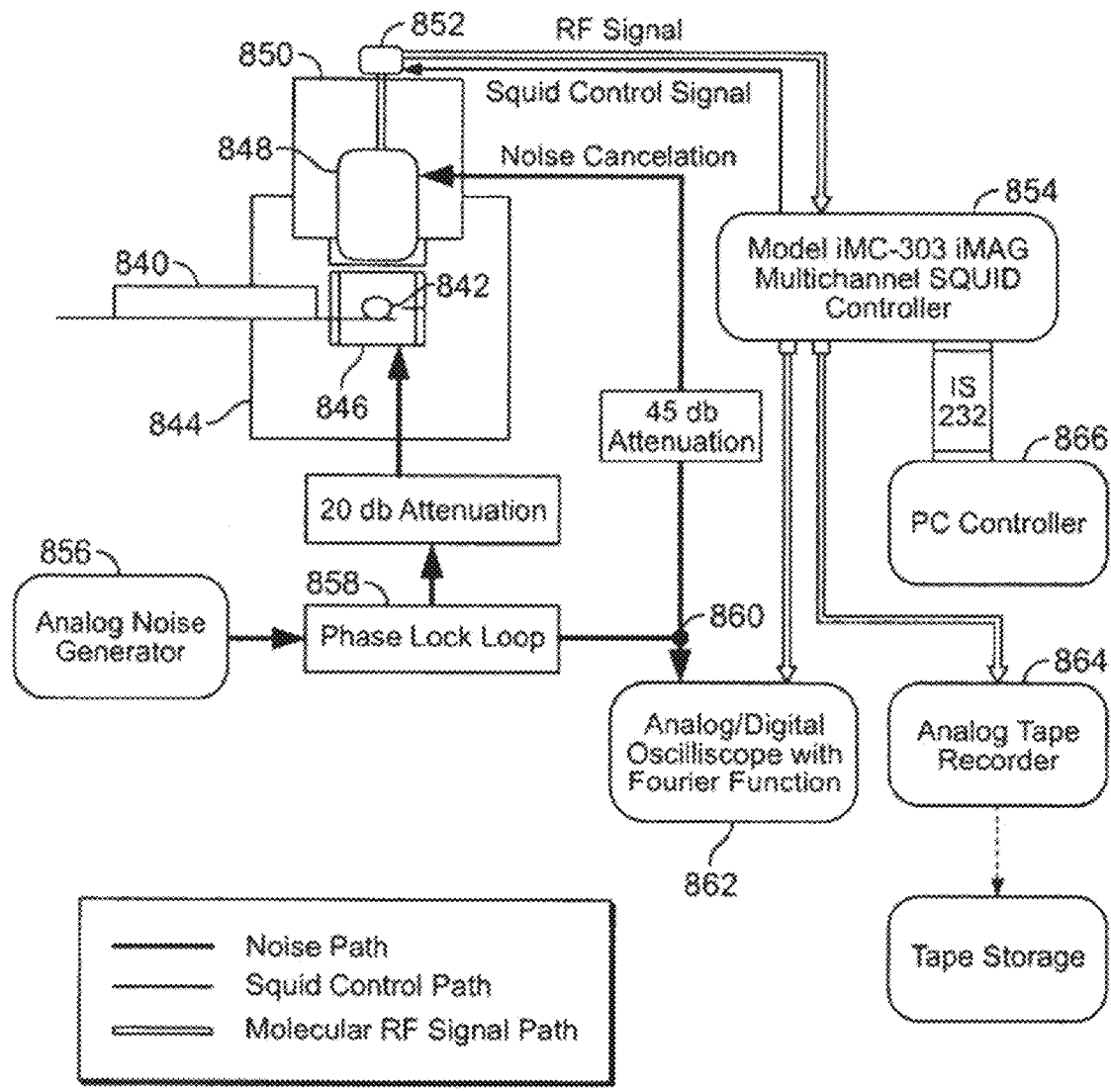
FIG. 8 diagram of the processing unit included in the detection system of the above Figures.

Referring to FIG. 8, a processing unit employing aspects of the invention includes a sample tray 840 that permits a sample 842 to be inserted into, and removed from, a Faraday cage 844 and Helmholtz coil 746. A SQUID/gradiometer detector assembly 848 is positioned within a cryogenic dewar 850. A flux-locked loop 852 is coupled between the SQUID/gradiometer detector assembly 848 and a SQUID controller 854. The SQUID controller 854 may be a model iMC-303 iMAG multichannel controller provided by Tristan.

An analog noise generator 856 provides a noise signal (as noted above) to a phase lock loop 858. The x-axis output of the phase lock loop is provided to the Helmholtz coil 846, and may be attenuated, such as by 20 dB. The y-axis output of the phase lock loop is split by a signal splitter 860. One portion of the y-axis output is input the noise cancellation coil at the SQUID, which has a separate input for the gradiometer. The other portion of the y-axis signal is input oscilloscope 862, such as an analog/digital oscilloscope having Fourier functions like the Tektronix TDS 3000b (e.g., model 3032b). That is, the x-axis output of the phase lock loop drives the Helmholz coil, and the y-axis output, which is in inverted form, is split to input the SQUID and the oscilloscope. Thus, the phase lock loop functions as a signal inverter. The oscilloscope trace is used to monitor the analog noise signal, for example, for determining when a sufficient level of noise for producing non-stationary spectral components is achieved. An analog tape recorder or recording device 864, coupled to the controller 854, records signals output from the device, and is preferably a wideband (e.g. 50 kHz) recorder. A PC controller 866 may be an MS Windows based PC interfacing with the controller 854 via, for example, an RS 232 port.

In FIG. 9, a block diagram of another embodiment of the processing unit is shown. A dual phase lock-in amplifier 202 is configured to provide a first signal (e.g., "x" or noise signal) to the coils 726, 728 and a second signal (e.g., "y" or noise cancellation signal) to a noise cancellation coil of a superconducting quantum interference device (SQUID) 206. The amplifier 202 is configured to lock without an external reference and may be a Perkins Elmer model 7265 DSP lock-in amplifier. This amplifier works in a "virtual mode," where it locks to an initial reference frequency, and then removes the reference frequency to allow it to run freely and lock to "noise."

An analog noise generator 200 is electrically coupled to the amplifier 202. The generator 200 is configured to generate or induce an analog white Gaussian noise at the coils 726, 728 via the amplifier 202. As an example, the generator 200 may be a model 1380 manufactured by General Radio.

An impedance transformer 204 is electrically coupled between the SQUID 206 and the amplifier 202. The impedance transformer 204 is configured to provide impedance matching between the SQUID 206 and amplifier 202.

The noise cancellation feature of the SQUID 206 can be turned on or off. When the noise cancellation feature is turned on, the SQUID 206 is capable of canceling or nullifying the injected noise component from the detected emissions. To provide the noise cancellation, the first signal to the coils 726, 728 is a noise signal at 20 dB or 35 dB above the molecular electromagnetic emissions sought to be detected. At this level, the injected noise takes on the characteristics of the molecular electromagnetic signal through stochastic resonance. The second signal to the SQUID 206 is a noise cancellation signal and is inverted from the first signal at an amplitude sufficient to null the noise at the SQUID output (e.g., 180 degrees out of phase with respect to the first signal).

The SQUID 206 is a low temperature direct element SQUID. As an example, the SQUID 206 may be a model LSQ/20 LTS dC SQUID manufactured by Tristan Technologies, Inc. Alternatively, a high temperature or alternating current SQUID can be used. The coils 722, 724 (e.g., gradiometer) and the SQUID 206 (collectively referred to as the SQUID/gradiometer detector assembly) combined has a magnetic field measuring sensitivity of approximately 5 microTesla/Hz. The induced voltage in the coils 722, 724 is detected and amplified by the SQUID 206. The output of the SQUID 206 is a voltage approximately in the range of 0.2-0.8 microVolts.

The output of the SQUID 206 is the input to a SQUID controller 208. The SQUID controller 208 is configured to control the operational state of the SQUID 206 and further condition the detected signal. As an example, the SQUID controller 208 may be an iMC-303 iMAG multi-channel SQUID controller manufactured by Tristan Technologies, Inc.

The output of the SQUID controller 208 is inputted to an amplifier 210. The amplifier 210 is configured to provide a gain in the range of 0-100 dB. A gain of approximately 20 dB is provided when noise cancellation node is turned on at the SQUID 206. A gain of approximately 50 dB is provided when the SQUID 206 is providing no noise cancellation.

The amplified signal is inputted to a recorder or storage device 212. The recorder 212 is configured to convert the analog amplified signal to a digital signal and store the digital signal. In one embodiment, the recorder 212 stores 8600 data points per Hz and can handle 2.46 Mbits/sec. As an example, the recorder 212 may be a Sony digital audiotape (DAT) recorder. Using a DAT recorder, the raw signals or data sets can be sent to a third party for display or specific processing as desired.

A lowpass filter 214 filters the digitized data set from the recorder 212. The lowpass filter 214 is an analog filter and may be a Butterworth filter. The cutoff frequency is at approximately 50 kHz.

A bandpass filter 216 next filters the filtered data sets. The bandpass filter 216 is configured to be a digital filter with a bandwidth between DC to 50 kHz. The bandpass filter 216 can be adjusted for different bandwidths.

The output of the bandpass filter 216 is the input to a Fourier transformer processor 218. The Fourier transform processor 218 is configured to convert the data set, which is in the time domain, to a data set in the frequency domain. The Fourier transform processor 218 performs a Fast Fourier Transform (FFT) type of transform.

The Fourier transformed data sets are the input to a correlation and comparison processor 220. The output of the recorder 212 is also an input to the processor 220. The processor 220 is configured to correlate the data set with previously recorded data sets, determine thresholds, and perform noise cancellation (when no noise cancellation is provided by the SQUID 206). The output of the processor 220 is a final data set representative of the spectrum of the sample's molecular low frequency electromagnetic emissions.

A user interface (UI) 222, such as a graphical user interface (GUI), may also be connected to at least the filter 216 and the processor 220 to specify signal processing parameters. The filter 216, processor 218, and the processor 220 can be implemented as hardware, software, or firmware. For example, the filter 216 and the processor 218 may be implemented in one or more semiconductor chips. The processor 220 may be software implemented in a computing device.

This amplifier works in a "virtual mode," where it locks to an initial reference frequency, and then removes the reference frequency to allow it to run freely and lock to "noise." The analog noise generator (which is produced by General Radio, a truly analog noise generator) requires 20 dB and 45-dB attenuation for the Helmholz and noise cancellation coil, respectively.

The Helmholz coil may have a sweet spot of about one cubic inch with a balance of $\frac{1}{100}$th of a percent. In an alternative embodiments, the Helmholtz coil may move both vertically, rotationally (about the vertical access), and from a parallel to spread apart in a pie shape. In one embodiment, the SQUID, gradiometer, and driving transformer (controller) have values of 1.8, 1.5 and 0.3 micro-Henrys, respectively. The Helmholtz coil may have a sensitivity of 0.5 Gauss per amp at the sweet spot.

Approximately 10 to 15 microvolts may be needed for a stochastic response. By injecting noise, the system has raised the sensitivity of the SQUID device. The SQUID device had a sensitivity of about 5 femtotesla without the noise. This system has been able to improve the sensitivity by 25 to 35 dB by injecting noise and using this stochastic resonance response, which amounts to nearly a 1,500% increase.

After receiving and recording signals from the system, a computer, such as a mainframe computer, supercomputer or high-performance computer does both pre and post processing, such by employing the Autosignal software product by Systat Software of Richmond Calif., for the pre-processing, while Flexpro software product does the post-processing. Flexpro is a data (statistical) analysis software supplied by Dewetron, Inc. The following equations or options may be used in the Autosignal and Flexpro products.

Forward Transform:

$$\hat{x}_k = \frac{1}{N}\sum_{n=0}^{N-1} x_n e^{-2\pi i k n/N}$$

Inverse Transform:

$$\hat{x}_k = \frac{1}{N}\sum_{n=0}^{N-1} x_n e^{-2\pi i k n/N}$$

FFT Algorithm:
Best Exact N using Temperton's Prime Factor FFT (C. Temperton, "Implementation of a Self-Sorting In-Place Prime Factor FFT Algorithm, Journal of Computation Physics, v. 58, p. 283, 1985).

Data Tapering Windows:
[cs4 BHarris min] 0.35875-0.48829*cos(2*Pi*i/(n−1))+0.14128*cos(4*Pi*i/(n−1))−0.01168*(6*Pi*i/(n−1)), i=0.n−1
[Rectangular] No fixed shape tapering available (Oscilloscope)
Magnitude: sqrt(Re*Re+Im*Im) [Re=real component, Im=imaginary component]
Amplitude: 2.0*sqrt(Re*Re+Im*Im)/n
db, decibels: 10.0*log 10(Re*Re+Im*Im)

Averaging Replicates:
Replicates are based on the X-values coinciding to within 1 e-8 fractional precision.

Reference Subtraction:
Reference Signal Subtraction (baseline noise) is performed on Y axis (amplitude) at each point (channel) along the X (time) axis. Negative Y values are then zeroed.

Cross-Correlation:
The function calculates the cross correlation function using summation and integration. Since the signal is transient, the correlation function is calculated using direct multiplication and integration. All of the values required for the calculation which lie outside the source channels (data series) are taken to be 0. The points for which t<0 are also calculated.

Fourier Significance Levels:
Monte Carlo data is fitted to parametric models. Where data size N is the only factor, univariate TableCurve 2D parametric models are used. For a segmented FFT where segment size and overlap are additional influences, trivariate Chebyshev polynominals are implemented. These are options selected under Autosignal. One could have data sets that analyze individually, or could be analyzed in an overlapping fashion where data set one would be analyzed, then the second half of data set one and the first half of data set two, then data set two, then the second half.

Figure 10:
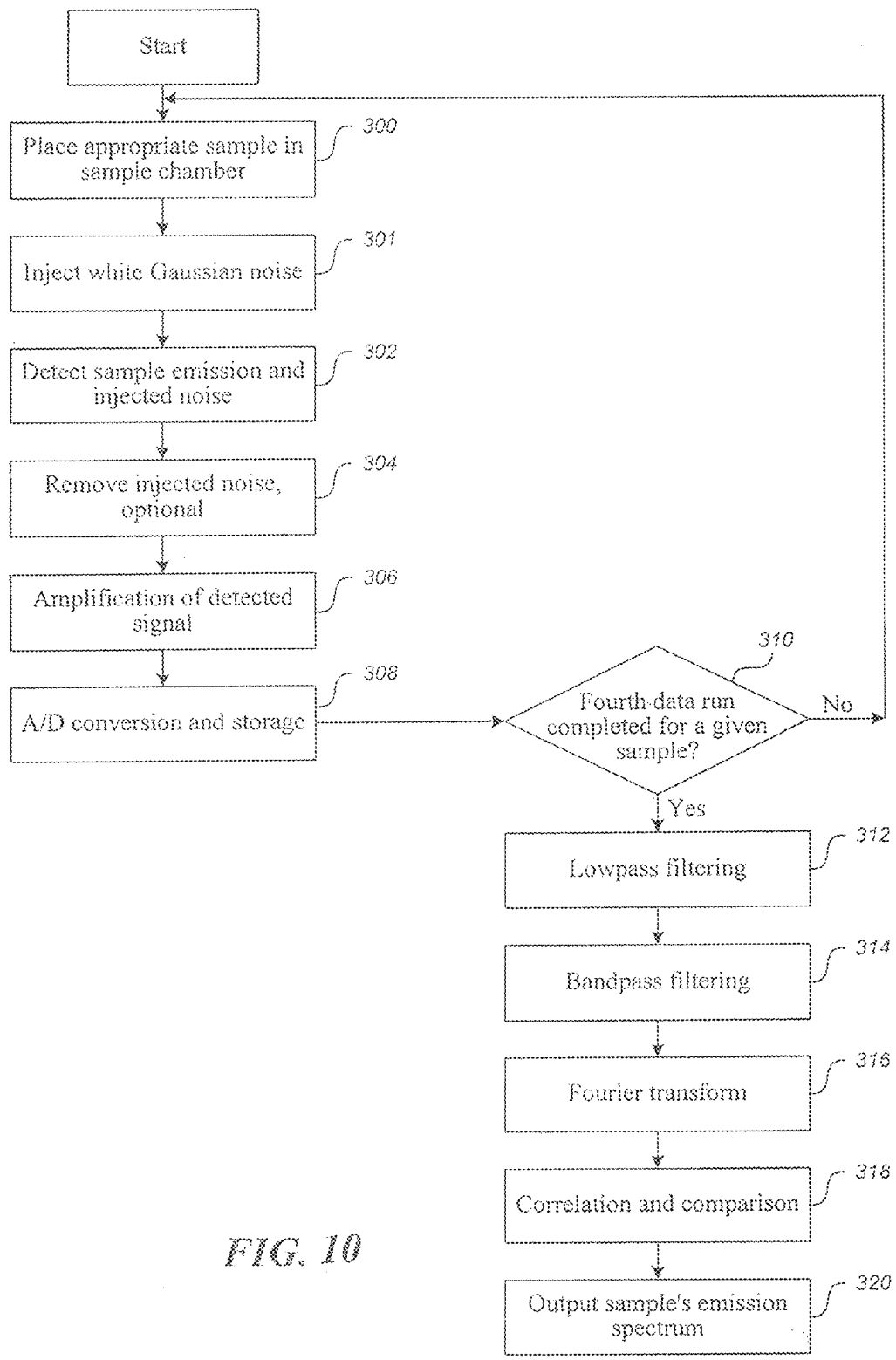
FIG. 10 is a flow diagram of the signal detection and processing performed by the present system.

A flow diagram of the signal detection and processing performed by the system 100 is shown in FIG. 10. When a sample is of interest, at least four signal detections or data runs are performed: a first data run at a time $t_1$ without the sample, a second data run at a time $t_2$ with the sample, a third data run at a time $t_3$ with the sample, and a fourth data run at a time $t_4$ without the sample. Performing and collecting data sets from more than one data run increases accuracy of the final (e.g., correlated) data set. In the four data runs, the parameters and conditions of the system 100 are held constant (e.g., temperature, amount of amplification, position of the coils, the noise signal, etc.).

At a block 300, the appropriate sample (or if it's a first or fourth data run, no sample), is placed in the system 100. A given sample, without injected noise, emits electromagnetic emissions in the DC-50 kHz range at an amplitude equal to or less than approximately 0.001 microTesla. To capture such low emissions, a white Gaussian noise is injected at a block 301.

At a block 302, the coils 722, 724 detect the induced voltage representative of the sample's emission and the injected noise. The induced voltage comprises a continuous stream of voltage values (amplitude and phase) as a function of time for the duration of a data run. A data run can be 2-20 minutes in length and hence, the data set corresponding to the data run comprises 2-20 minutes of voltage values as a function of time.

At a block 304, the injected noise is cancelled as the induced voltage is being detected. This block is omitted when the noise cancellation feature of the SQUID 206 is turned off.

At a block 306, the voltage values of the data set are amplified by 20-50 dB, depending on whether noise cancellation occurred at the block 304. And at a block 308, the amplified data set undergoes analog to digital (A/D) conversion and is stored in the recorder 212. A digitized data set can comprise millions of rows of data.

After the acquired data set is stored, at a block 310 a check is performed to see whether at least four data runs for the sample have occurred (e.g., have acquired at least four data sets). If four data sets for a given sample have been obtained, then lowpass filtering occurs at a block 312. Otherwise, the next data run is initiated (return to the block 300).

After lowpass filtering (block 312) and bandpass filtering (at a block 314) the digitized data sets, the data sets are converted to the frequency domain at a Fourier transform block 316.

Next, at a block 318, like data sets are correlated with each other at each data point. For example, the first data set corresponding to the first data run (e.g., a baseline or ambient noise data run) and the fourth data set corresponding to the fourth data run (e.g., another noise data run) are correlated to each other. If the amplitude value of the first data set at a given frequency is the same as the amplitude value of the fourth data set at that given frequency, then the correlation value or number for that given frequency would be 1.0. Alternatively, the range of correlation values may be set at between 0-100. Such correlation or comparison also occurs for the second and third data runs (e.g., the sample data runs). Because the acquired data sets are stored, they can be accessed at a later time as the remaining data runs are completed.

When the SQUID 206 provides no noise cancellation, then predetermined threshold levels are applied to each correlated data set to eliminate statistically irrelevant correlation values. A variety of threshold values may be used, depending on the length of the data runs (the longer the data runs, greater the accuracy of the acquired data) and the likely similarity of the sample's actual emission spectrum to other types of samples. In addition to the threshold levels, the correlations are averaged. Use of thresholds and averaging correlation results in the injected noise component becoming very small in the resulting correlated data set.

If noise cancellation is provided at the SQUID 206, then the use of thresholds and averaging correlations are not necessary.

Once the two sample data sets have been refined to a correlated sample data set and the two noise data sets have been refined to a correlated noise data set, the correlated noise data set is subtracted from the correlated sample data set. The resulting data set is the final data set (e.g., a data set representative of the emission spectrum of the sample) (block 320).

Since there can be 8600 data points per Hz and the final data set can have data points for a frequency range of DC-50 kHz, the final data set can comprise several hundred million rows of data. Each row of data can include the frequency, amplitude, phase, and a correlation value.

Figure 11A:
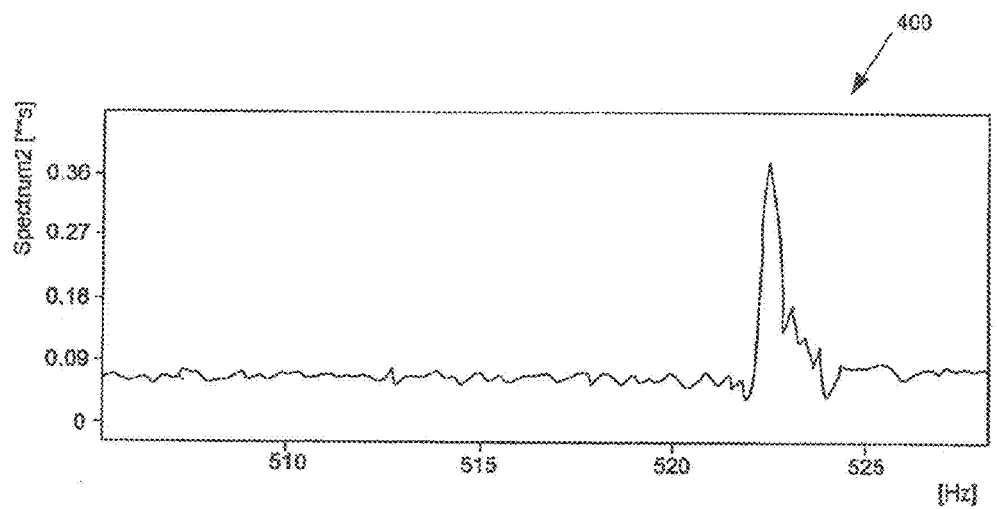
FIG. 11A is a spectral plot of the emissions of a first sample.
Figure 11B:
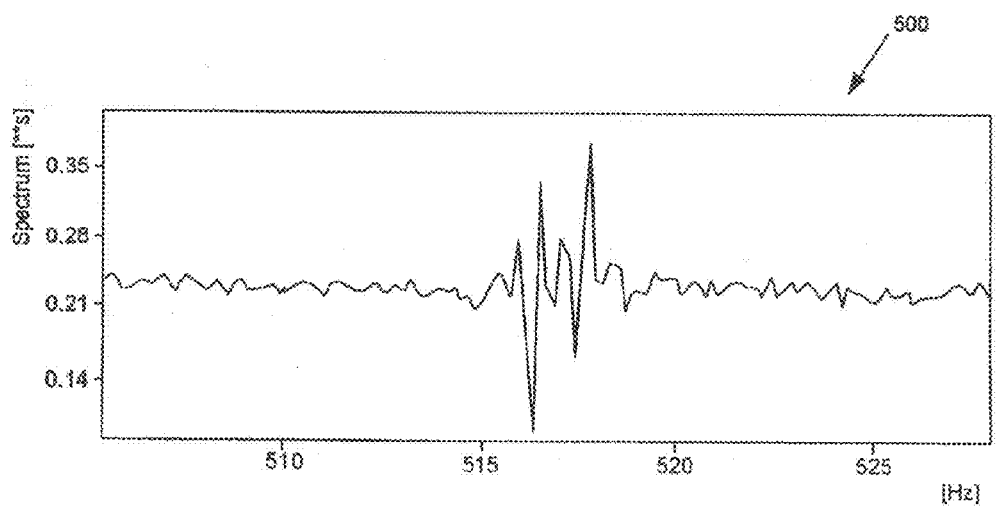
FIG. 11B is spectral plot of the emissions of a second sample.
Figure 12A:
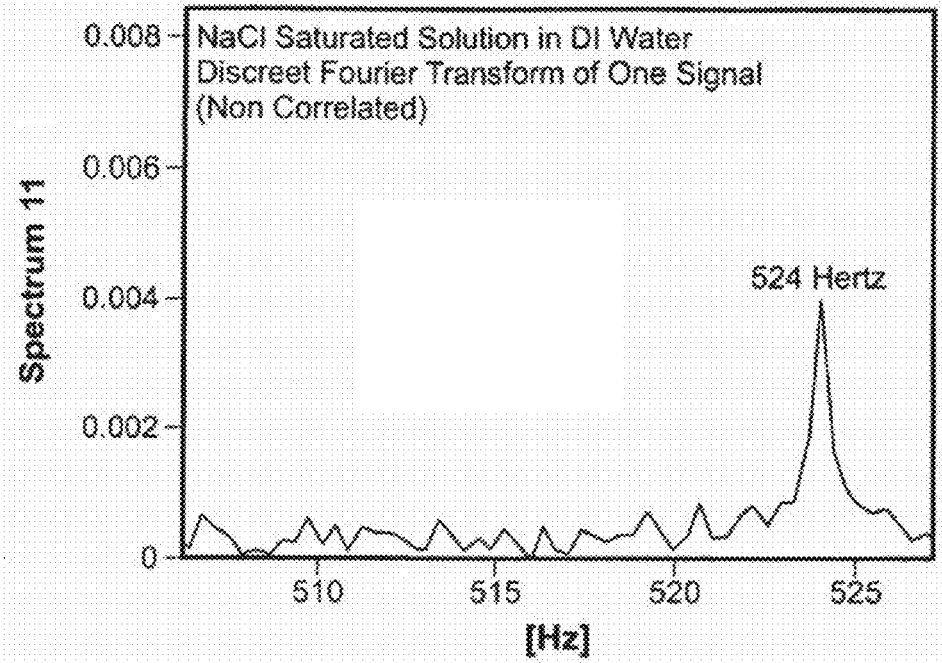
FIGS. 12A and 12B are spectral plots, in the spectral region between 500-530 Hz, for a sample of saturated NaCl, generated by Fourier transforming a non-correlated time-domain sample signal (12A), and Fourier transforming a cross-correlated sample spectrum (12B).
Figure 12B:
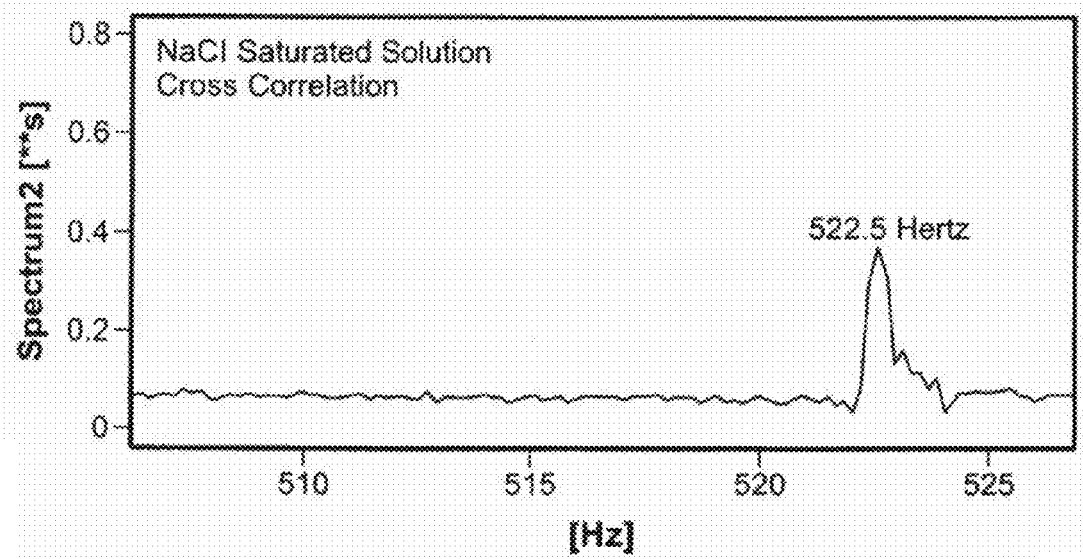
Figure 13A:
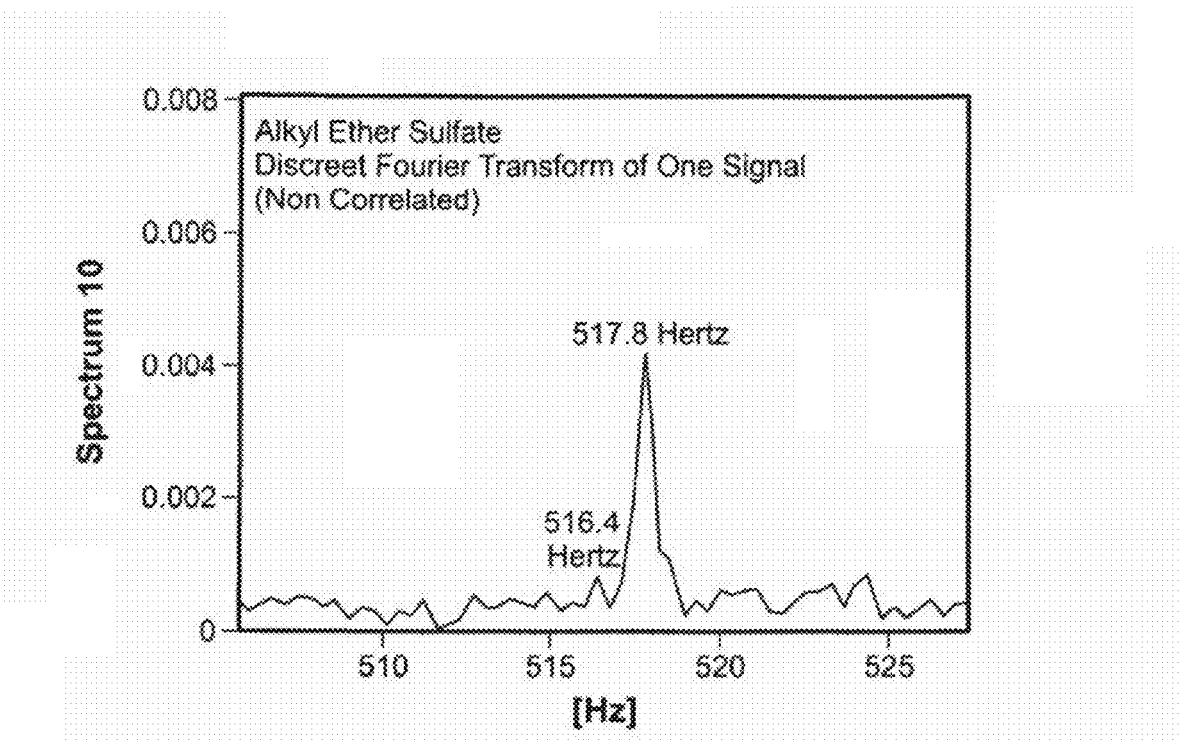
FIGS. 13A and 13B are spectral plots, in the spectral region between 500-530 Hz, for a sample of alkyl ether sulfate, generated by Fourier transforming a non-correlated time-domain sample signal (13A), and Fourier transforming a cross-correlated sample spectrum (13B).
Figure 13B:
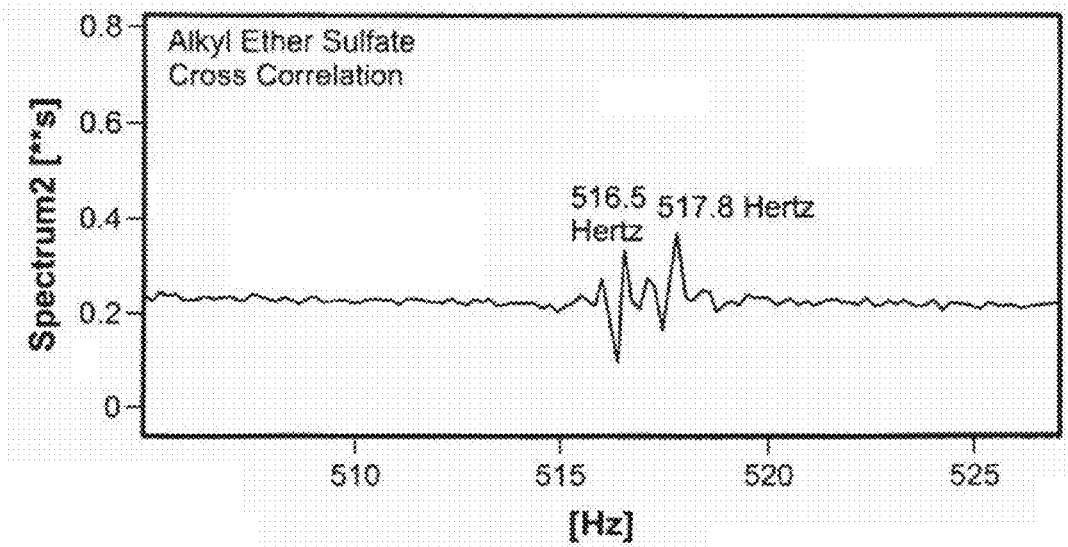
Figure 14A:
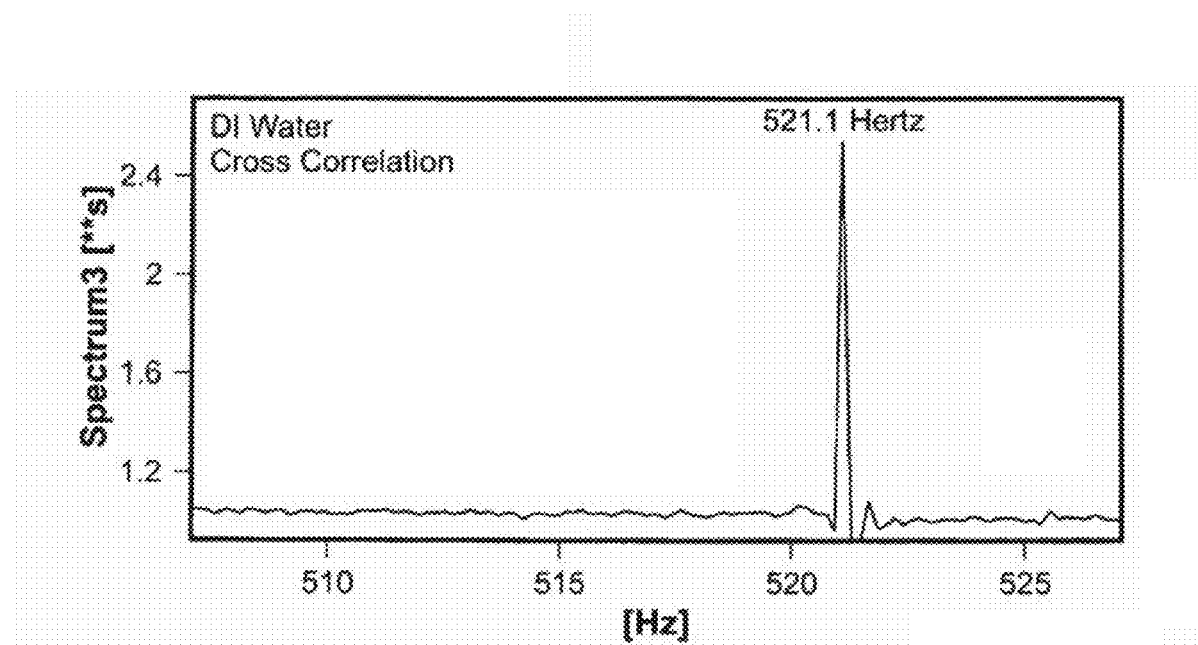
FIGS. 14A-14F are spectral plots, in the spectral region between 500-530 Hz, for samples of deionized water (14A), a saturated NaCl solution (14B), a solution of 1% NaCl in deionized water (14C); a saturated NaBr sample (14D), alkyl ether sulfate in deionized water (14E), and no sample (14F).
Figure 14B:
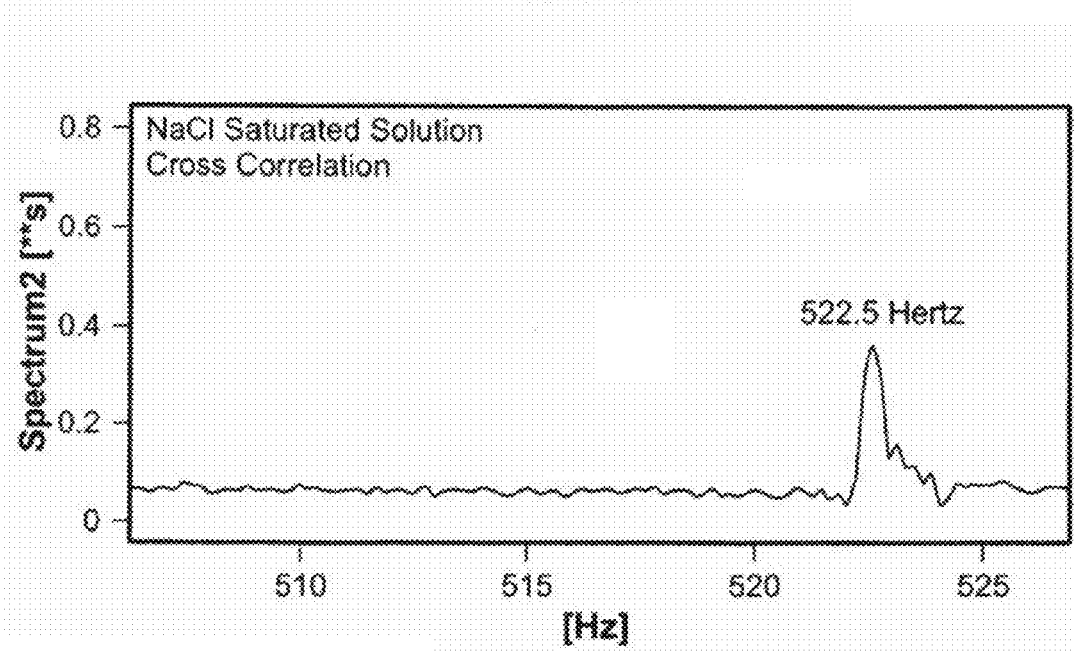
Figure 14C:
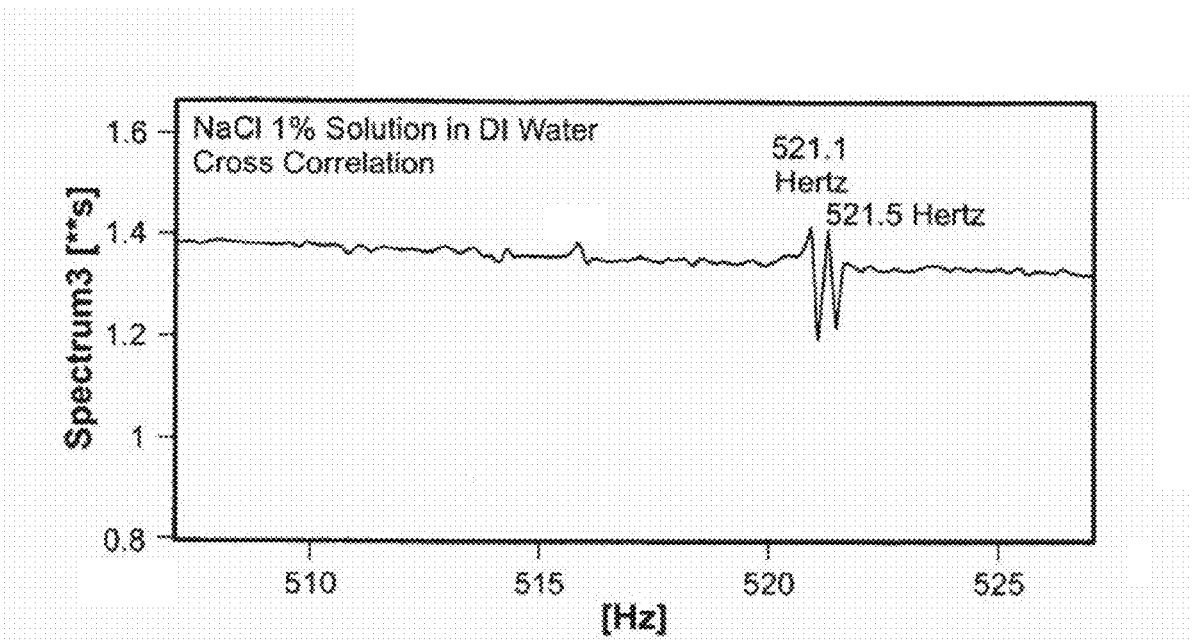
Figure 14D:
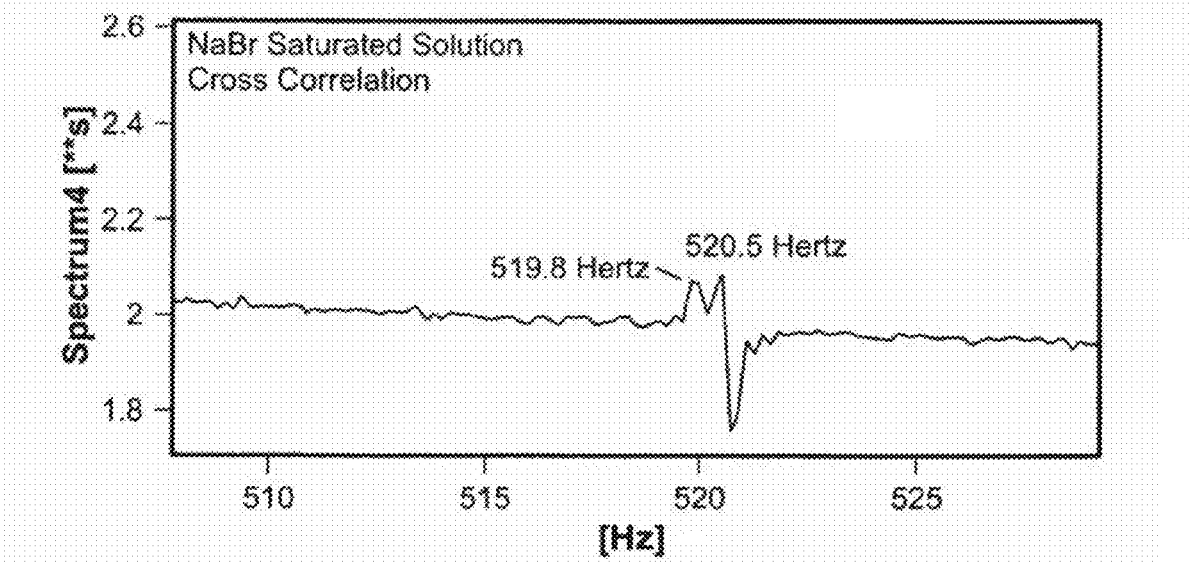
Figure 14E:
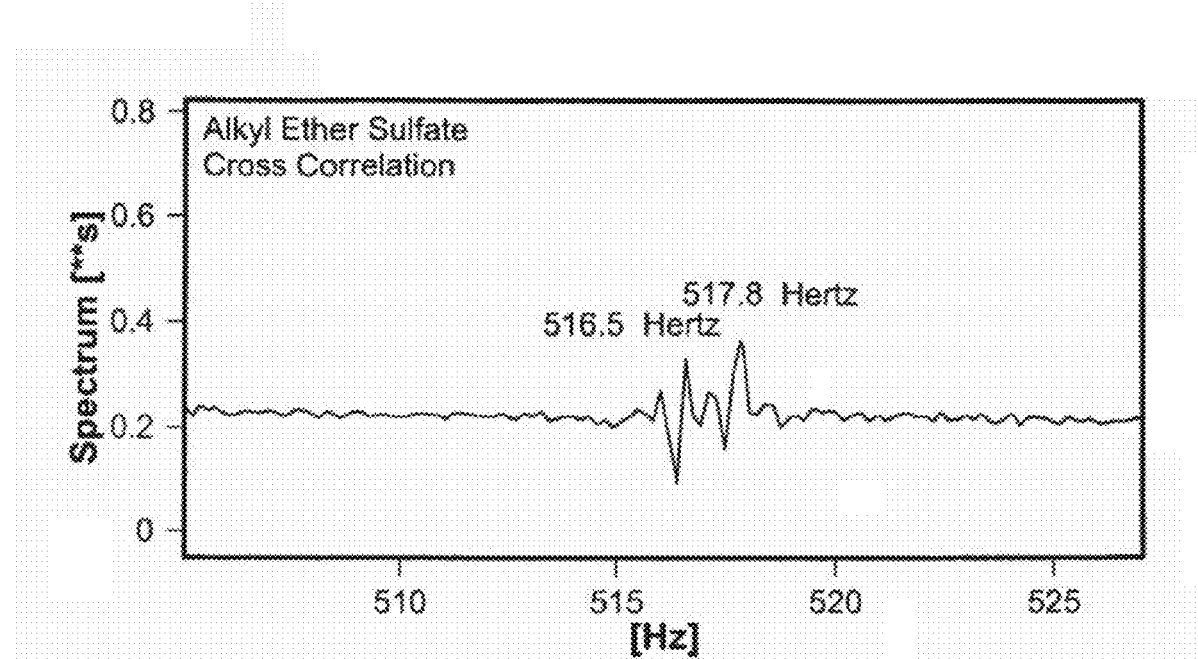
Figure 14F:
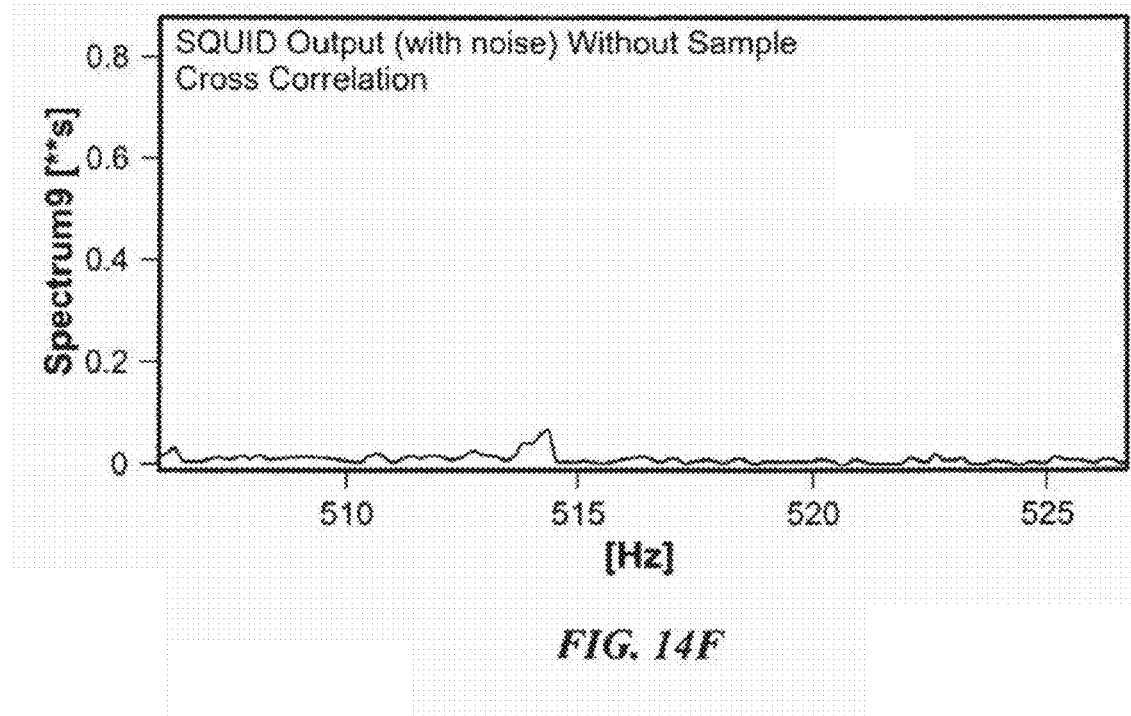
Figure 15A:
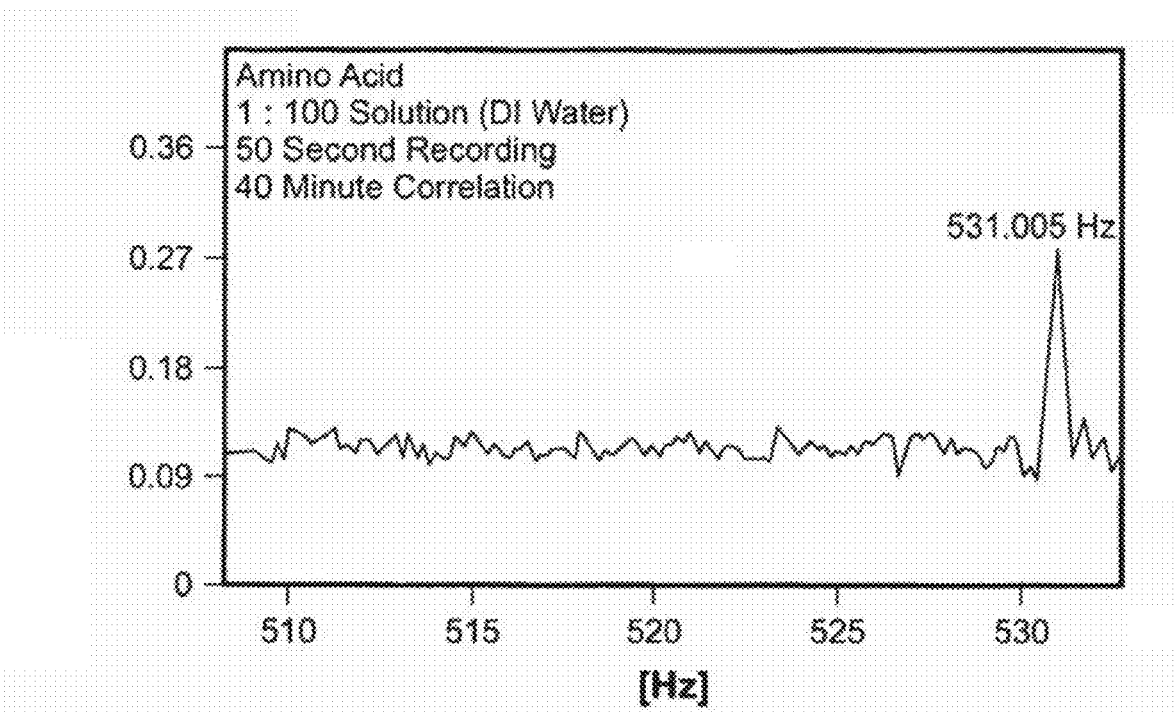
FIGS. 15A-15F are spectral plots, in the spectral region between 500 and 535 Hz, of a sample of an amino acid at a 1:100 wt/volume solution (15A) and at increasing w/v dilutions of 1:10,000 (15B), 1:1 million (15C), 1:100 million (15D), 1:10 billion (15E and 15F), where the spectra in FIGS. 15A-15E were generated with 50 second recordings and 40 minute correlations, and the spectrum of FIG. 15F was generated with a 4:25 minute recording with a 12 hour correlation.
Figure 15B:
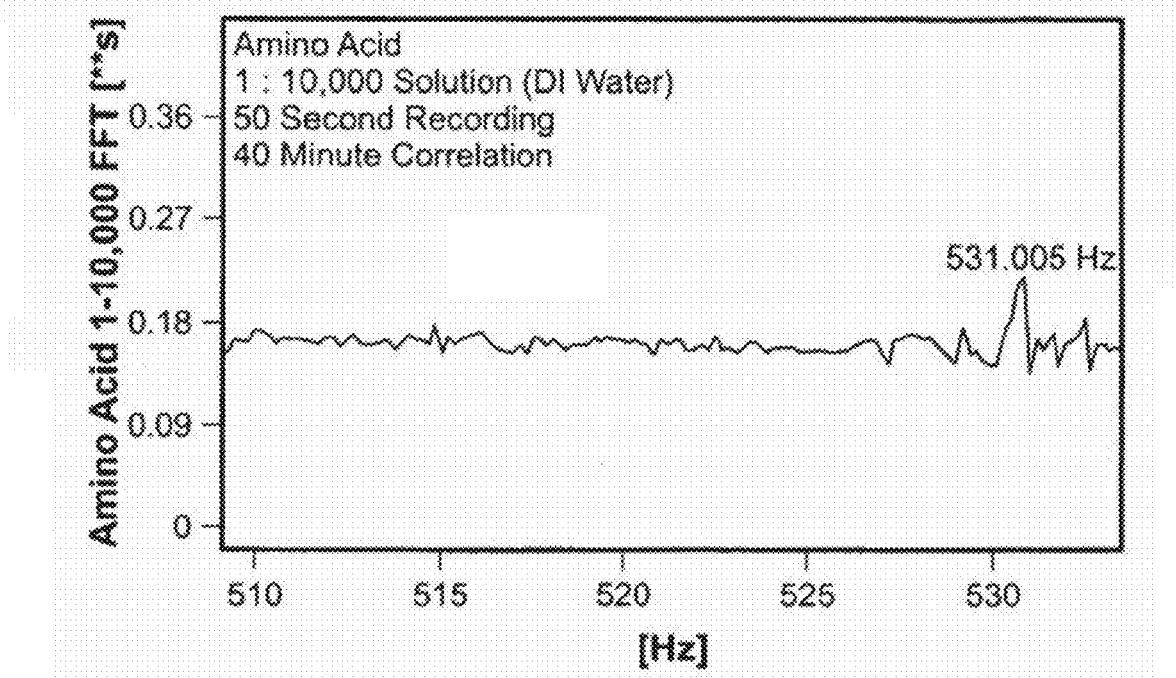
Figure 15C:
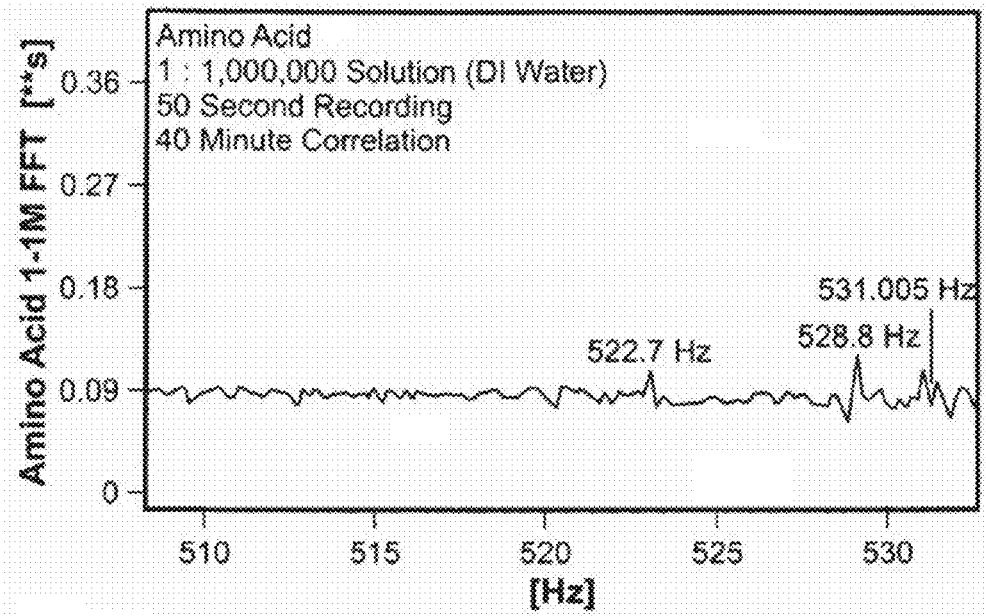
Figure 15D:
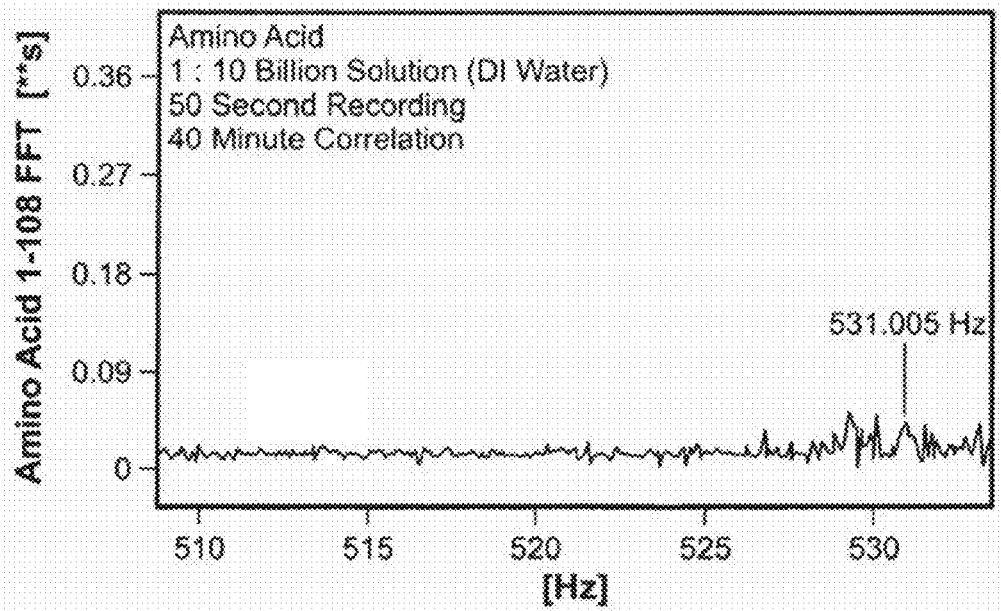
Figure 15E:
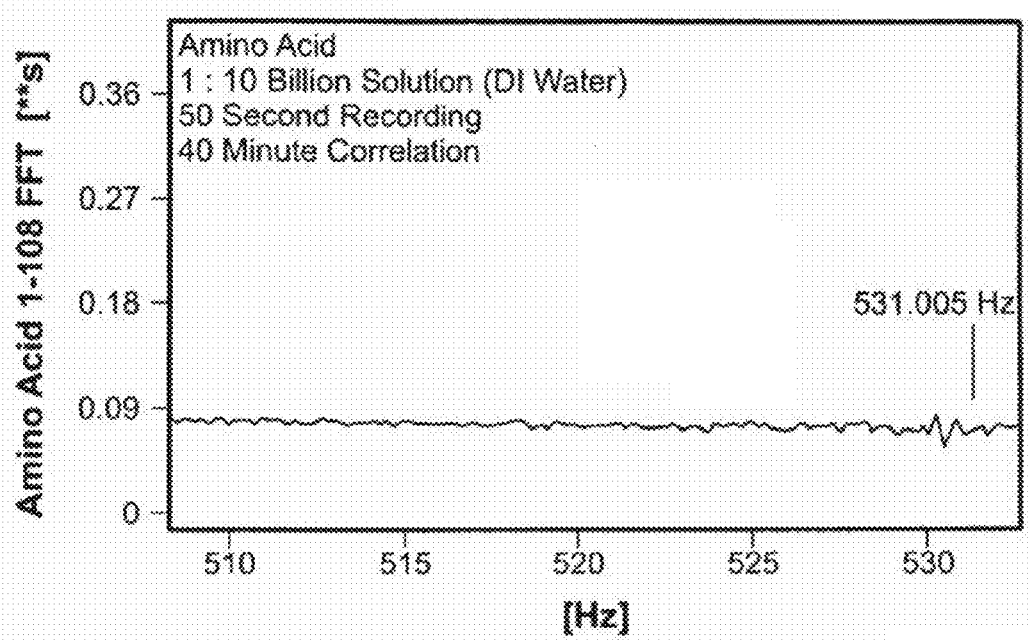
Figure 15F:
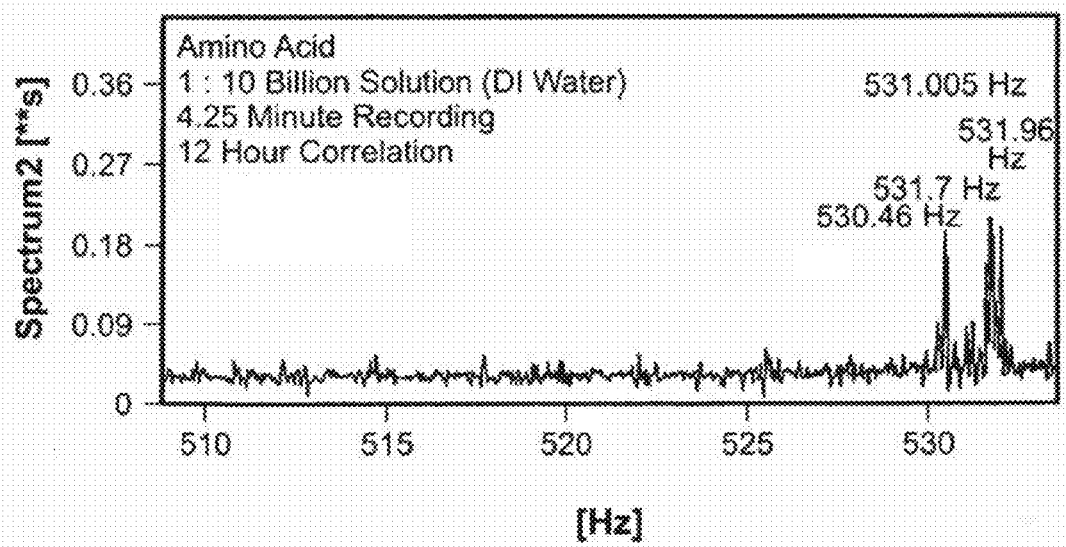

In FIGS. 11A and 11B, there are shown examples of sample emission spectrums. A Fourier plot 400 shown in FIG. 11A corresponds to a spectrum of a sample of saturated sodium chloride solution. A Fourier plot 500 shown in FIG. 11B corresponds to a spectrum of a sample of an enzyme.

Referring to FIG. 16, another alternative embodiment to the systems described above will now be described as a system 1600. In general, alternatives and alternative embodiments described herein are substantially similar to previously described embodiments, and the same reference numbers often identify common elements and functions. Only significant differences in construction or operation are described in detail.

A second derivative gradiometer is shown as 1602, where the target sample is positioned between upper and lower pairs of coils. Two inner coils on opposite sides of the sample complement each other, while two outer coils (top and bottom coils) each complement each other, and oppose the two inner coils. Such an arrangement allows for greater signal extraction from the sample and improved noise rejection.

While shown in the Figures and described in greater detail below, the system 1600 employs a concentric series of elements and an arrangement along a central axis extending into the dewar. A stepper motor 1604 allows the sample to be positioned axially within this arrangement of concentric elements. In particular, the sample may be positioned at a desired location within a middle of the gradiometer 1602.

Likewise, a micrometer adjustment mechanism 1606, such as a mechanical micrometer or stepper motor, allows the Helmholtz coils to be aligned with respect to elements in the system (such as the sample and gradiometer). Such an adjustment of the Helmholtz coil aids in manufacture and calibration of the system 1600, as well as allowing precise alignment of fields within the system, such as providing a uniform field with respect to the gradiometer 1602. It may be useful to also provide a field offset or change in field gradient to produce a better stochastic result, to offset noise in the system, or to provide other benefits.

FIGS. 17A, 17B, and 18 show more clearly the concentric arrangement of elements within the system 1600, wherein the sample tube extends axially through a center of a low pass filtering metal shield 1802 (such as a stainless steel alloy) to pass signals below 2 kHz. An outer magnetic (MU) shield surrounds the gradiometer, Helmholtz coils and sample. The arrangement of system 1600 is generally self-explanatory with respect to the Figures.

The random white noise generator, model 1381, manufactured by General Radio and described above, may be replaced by a programmable Gaussian white noise generator manufactured by Noise/Com. Such a generator employs two outputs, one inverted from the other. One output may be connected to the Helmholtz coil, with the other (inverted) output connected to the SQUID noise cancellation coil noted above.

Likewise, as shown in FIG. 19, the Tektronix digital oscilliscope noted above may be replaced by a two-channeled dynamic signal analyzer 1902, model SR 785, manufactured by Stanford Research Systems. Such a signal analyzer may process incoming signals by sampling multiple time domain signals and averaging them across multiple frequency domain FFT's. This may result in a full spectrum frequency domain record of all non-random signal components. Other changes that may be made include replacing the digital audio tape storage system with a digital versatile disk (DVD) recorder 1904. Further, a data acquisition board 1906 manufactured by Keithley, model 3801, may be used, which works with software for generating histograms, as described below.

In the alternative embodiment shown in FIG. 19, a noise cancellation coil 1908 is connected between the gradiometer and SQUID. (While a first derivative gradiometer is shown, a second derivative gradiometer, such as that shown in FIG. 16, may be used.) While not shown in FIG. 19, an inverted noise channel (inverted with respect to noise applied to the Helmholtz coils) may be applied to the noise cancellation coil 1908 (and may first pass through an impedance transformer that attenuates the noise signal by, for example, 45 dB). In an alternative embodiment, not shown, the noise cancellation coil may be positioned within the SQUID 120, between the SQUID input and output coils.

III. Method of Producing an Optimized Time-Domain Signal

According to one aspect of the invention, it has been discovered that sample-dependent spectral features in a low-frequency time-domain signal obtained for a given sample can be optimized by recording time-domain signals for sample over a range of noise levels, that is power gain on the noise injected into the sample during signal recording. The recorded signals are then processed to reveal spectral signal features, and the time domain signal having an optimal spectral-features score, as detailed below, is selected. The selection of optimized or near-optimized time-domain signals is useful because it has been found, also in accordance with the invention, that transducing a chemical or biological system with an optimized time-domain signal gives a stronger and more predictable response than with a non-optimized time-domain signal. Viewed another way, selecting an optimized (or near-optimized) time-domain signal is useful in achieving reliable, detectable sample effects when a target system is transduced by the sample signal.

In general, the range of injected noise levels over which time-domain signals are typically recorded between about 0 to 1 volt, typically, or alternatively, the noise injected is preferably between about 30 to 35 decibels above the molecular electromagnetic emissions sought to be detected, e.g., in the range 70-80-dbm. The number of samples that are recorded, that is, the number of noise-level intervals over which time-domain signals are recorded may vary from 10-100 or more, typically, and in any case, at sufficiently small intervals so that a good optimum signal can be identified. For example, the power gain of the noise generator level can be varied over 50 20 mV intervals. As will be seen below, when the spectral-feature scores for the signals are plotted against level of injected noise, the plot shows a peak extending over several different noise levels when the noise-level increments are suitable small.

The present invention contemplates three different methods for calculating spectral-feature scores for the recorded time-domain signals. These are (1) a histogram bin method, (2) generating an FFT of autocorrelated signals, and (3) averaging of FFTs, and each of these is detailed below.

Although not specifically described, it will be appreciated that each method may be carried out in a manual mode, where the user evaluates the spectra on which a spectral-feature score is based, makes the noise-level adjustment for the next recording, and determines when a peak score is reached, or it may be carried out in an automated or semi-automated mode, in which the continuous incrementing of noise level and/or the evaluation of spectral-feature score, is performed by a computer-driven program.

A. Histogram Method of Generating Spectral Information

FIG. 20 is a high level data flow diagram in the histogram method for generating spectral information. Data acquired from the SQUID (box 2002) or stored data (box 2004) is saved as 16 bit WAV data (box 2006), and converted into double-precision floating point data (box 2008). The converted data may be saved (box 2010) or displayed as a raw waveform (box 2012). The converted data is then passed to the algorithm described below with respect to FIG. 21, and indicated by the box 2014 labeled Fourier Analysis. The histogram can be displayed at 2016. Alternatively, and as will be described below, the converted data may be passed to one of two additional algorithms for identifying spectral features in time domain signals.

With reference to FIG. 21, the general flow of the histogram algorithm is to take a discrete sampled time-domain signal and use Fourier analysis to convert it to a frequency domain spectrum for further analysis. The time-domain signals are acquired from an ADC (analog/digital converter) and stored in the buffer indicated at 2102. This sample is SampleDuration seconds long, and is sampled at SampleRate samples per second, thus providing SampleCount (SampleDuration*SampleRate) samples. The FrequencyRange that can be recovered from the signal is defined as half the SampleRate, as defined by Nyquist. Thus, if a time-series signal is sampled at 10,000 samples per second, the FrequencyRange will be 0 Hz to 5 kHz. One Fourier algorithm that may be used is a Radix 2 Real Fast Fourier Transform (RFFT), which has a selectable frequency domain resolution (FFTSize) of powers of two up to $2^{16}$. An FFTSize of 8192 is selected, to provide provides enough resolution to have at least one spectrum bin per Hertz as long as the FrequencyRange stays at or below 8 kHz. The SampleDuration should be long enough such that SampleCount>(2*) FFTSize*10 to ensure reliable results.

Since this FFT can only act on FFTSize samples at a time, the program must perform the FFT on the samples sequentially and average the results together to get the final spectrum. If one chooses to skip FFTSize samples for each FFT, a statistical error of 1/FFTSize 0.5 is introduced. If, however, one chooses to overlap the FFT input by half the FFTSize, this error is reduced to 1/(0.81*2*FFTSize) 0.5. This reduces the error from 0.0110485435 to 0.0086805556. Additional information about errors and correlation analyses in general, consult Bendat & Piersol, "Engineering Applications of Correlation and Spectral Analysis", 1993.

Prior to performing the FFT on a given window, a data tapering filter may be applied to avoid spectral leakage due to sampling aliasing. This filter can be chosen from among Rectangular (no filter), Hamming, Hanning, Bartlett, Blackman and Blackman/Harris, as examples.

In an exemplary method, and as shown in box 2104, we have chosen 8192 for the variable FFTSize, which will be the number of time-domain samples we operate on at a time, as well as the number of discrete frequencies output by the FFT. Note that FFTSize=8192 is the resolution, or number of bins in the range which is dictated by the sampling rate. The variable n, which dictates how many discrete RFFT's (Real FFT's) performed, is set by dividing the SampleCount by FFTSize*2, the number of FFT bins. In order for the algorithm to generate sensible results, this number n should be at least 10 to 20 (although other valves are possible), where more may be preferred to pick up weaker signals. This implies that for a given SampleRate and FFTSize, the SampleDuration must be long enough. A counter m, which counts from 0 to n, is initialized to zero, also as shown in box 2104.

The program first establishes three buffers: buffer 2108 for FFTSize histogram bins, that will accumulate counts at each bin frequency; buffer 2110 for average power at each bin frequency, and a buffer 2112 containing the FFTSize copied samples for each m.

The program initializes the histograms and arrays (box 2113) and copies FFTSize samples of the wave data into buffer 2112, at 2114, and performs an RFFT on the wave data (box 2115). The FFT is normalized so that the highest amplitude is 1 (box 2116) and the average power for all FFTSize bins is determined from the normalized signal (box 2117). For each bin frequency, the normalized value from the FFT at that frequency is added to each bin in buffer 2108 (box 2118).

In box 2119 the program then looks at the power at each bin frequency, relative to the average power calculated from above. If the power is within a certain factor epsilon (between 0 and 1) of the average power, then it is counted and the corresponding bin is incremented in the histogram buffer at 16. Otherwise it is discarded.

Note that the average power it is comparing to is for this FFT instance only. An enhanced, albeit slower algorithm might take two passes through the data and compute the average over all time before setting histogram levels. The comparison to epsilon helps to represent a power value that is significant enough for a frequency bin. Or in broader terms, the equation employing epsilon helps answer the question, "is there a signal at this frequency at this time?" If the answer is yes, it could be one of two things: (1) stationary noise which is landing in this bin just this one time, or (2) a real low level periodic signal which will occur nearly every time. Thus, the histogram counts will weed out the noise hits, and enhance the low level signal hits. So, the averaging and epsilon factor allow one to select the smallest power level considered significant.

Counter m is incremented at box 2120, and the above process is repeated for each n set of WAV data until m is equal to n (box 2121). At each cycle, the average power for each bin is added to the associated bin at 2118, and each histogram bin is incremented by one when the power amplitude condition at 2114 is met.

Figure 22A:
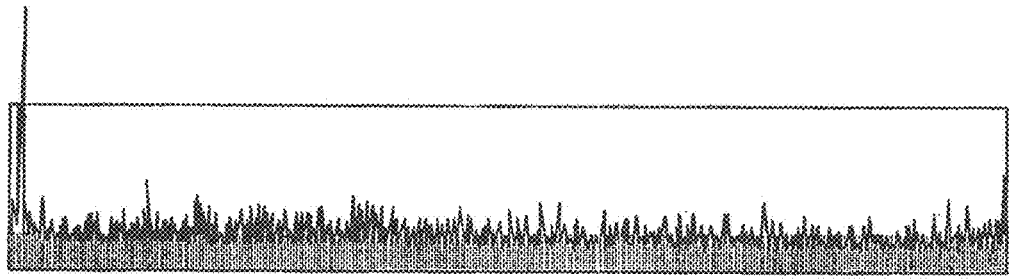
Figure 22B:
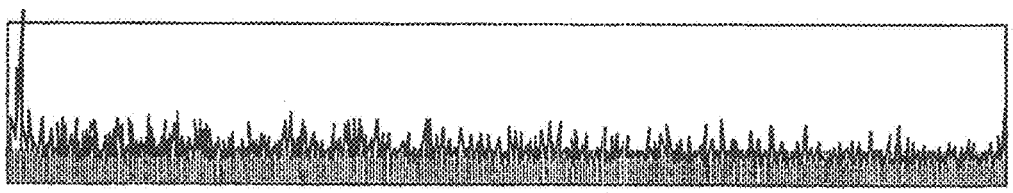
Figure 22C:
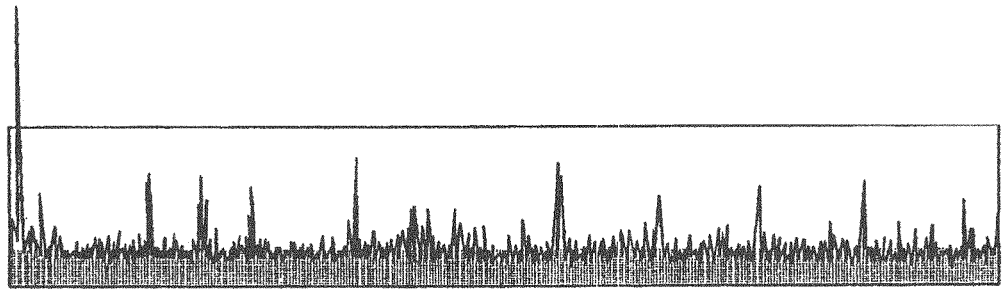
Figure 22D:
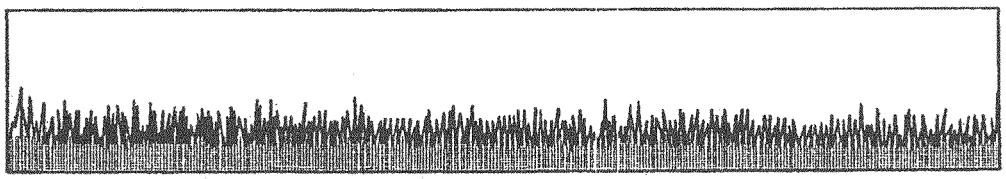

When all n cycles of data have been considered, the average power in each bin is determined by dividing the total accumulated average power in each bin by n, the total number of cycles (box 2122) and the results displayed (box 2123). Except where structured noise exists, e.g., DC=0 or at multiples of 60 Hz, the average power in each bin will be some relatively low number. This is indicated in the plots shown at FIGS. 22A-D (the histograms generated at 400, 600, 700, and 900 mV). The plots of FIGS. 22A-22D show only a portion of the histogram bins, namely a spectrum from 7953 Hz through 8533 Hz. As shown in FIGS. 22A and 22B, no stochastic event is visible at 400 mV or 600 mV of injected noise, respectively. However, as shown in FIG. 22C, at 700 mV, a visible stochastic event is evident. Thereafter, as shown in FIG. 22D, at 900 mV, the stochastic event is lost.

The histogram produced by the above steps contains, in each bin, a count between 0 and n of the number of times that the power at that frequency was above (epsilon*the average power for that whole FFT output). If a bin count is incremented due to unstructured noise, that noise will be distributed across all the frequency bins over time, thus not adding up to much in a given bin. If there is consistent signal at a given frequency, it will be present at each of the n time slices and thus have a bin count approaching n. Large amplitude noise, such as sixty hertz and its harmonics have both high bin counts as well as high average power. We can differentiate between these frequencies, and the ones we are interested in that have low average power, but high bin counts.

FIGS. 22A-22D show histograms generated by the method at four different noise power inputs. As shown, the program may display average power at each frequency as a vertical bar. The histogram bin counts may be represented as a connected upper line. If the power is considered "low" (e.g. less than average/3), and the histogram has a certain count, then a connecting line may become observable between the peak of a power bar and a peak of a histogram bar. Bins highlighted by the connecting lines are likely candidates for low energy molecular spectra.

It can be appreciated from FIGS. 22A-22D and from the above, that there are two settings of note used in generating a meaningful histogram, that is, a histogram that shows stochastic resonance effects related to a sample being interrogated. The first is the power level of noise (in this case, Gaussian white noise) supplied to the sample. If this level is too low, the noise level is not sufficient to create stochastic resonance and the bin histogram reflects noise only. If the power input is too high, the average power level calculated for each bin is high and stochastic events cannot be distinguished. An optimal noise level from this study is around 700 mV, although the true optimum may be further determined by applying the method to signals recorded at a signal gain at a number of smaller increments between, say 650 and 750 mV.

The spectral-feature score in this method is determined by counting the number of stochastic events which are above a bin count corresponding to value that is statistically greater than the average noise for that bin in the absence of a stochastic event. In the plots shown in FIGS. 22A-22C, this average bin count is at or slightly above the apparently random peaks distributed along the spectral axis, as seen particularly in FIGS. 22A-22C. At an optimal noise gain (FIG. 22A), a number of bin peaks that are clearly above this level are observed, and these peaks are counted over a selected frequency interval, e.g., DC to 1 kHz or DC-8 kHz, to determine a spectral-feature score for the corresponding time-domain signal.

The relevant settings in this method are noise gain and the value of epsilon. This value determines a power value that will be used to distinguish an event over average value. At a value of 1, no events will be detected, since power will never be greater than average power. As epsilon approaches zero, virtually every value will be placed in a bin. Between 0 and 1, and typically at a value that gives a number of bin counts between about 20-50% of total bin counts for structured noise, epsilon will have a maximum "spectral character," meaning the stochastic resonance events will be most highly favored over pure noise.

Therefore, one can systematically increase the power gain on the noise input, e.g., in 50 mV increments between 0 and 1 V, and at each power setting, adjust epsilon until a histogram having well defined peaks is observed. Where, for example, the sample being processed represents a 20 second time interval, total processing time for each different power and epsilon will be about 25 seconds. When a well-defined signal is observed, either the power setting or epsilon or both can be refined until an optimal histogram, meaning one with the largest number of identifiable peaks, is produced.

Under this algorithm, numerous bins may be filled and associated histogram rendered for low frequencies due to the general occurrence of noise (such as environmental noise) at the low frequencies. Thus, the system may simply ignore bins below a given frequency (e.g., below 1 kHz), but still render sufficient bin values at higher frequencies to determine unique signal signatures between samples.

Alternatively, since a purpose of the epsilon variable is to accommodate different average power levels determined in each cycle, the program could itself automatically adjust epsilon using a predefined function relating average power level to an optimal value of epsilon.

Similarly, the program could compare peak heights at each power setting, and automatically adjust the noise power setting until optimal peak heights or character is observed in the histograms.

Although the value of epsilon may be a fixed value for all frequencies, it is also contemplated to employ a frequency-dependent value for epsilon, to adjust for the higher value average energies that may be observed at low frequencies, e.g., DC to 1,000. A frequency-dependent epsilon factor could be determined, for example, by averaging a large number of low-frequency FFT regions, and determining a value of epsilon that "adjusts" average values to values comparable to those observed at higher frequencies.

Referring to FIGS. 23A-23C, an example of a user interface for generating histograms is shown. A slider bar 2302 determines the length of a sample waveform segment, such as up to 300-600 seconds, and allows a user to effectively scroll within a waveform. A box 2304 allows the user to set a Nyquist frequency, such as 5, 10 or 20 kHz, and also provided is an adjacent reset button. A slider bar 2306 allows the user to move the baseline for histograms, while a 60 Hz checkbox 2308 allows the user to identify the 60 Hz bin and all related 60 Hz harmonics with vertical lines (as shown in FIG. 23C). When an acquire button 2312 is selected, the software generates or acquires a waveform from a sample, such as that shown in FIG. 23B. When an fft button 2310 is selected, the software generates a histogram plot, such as that shown in FIG. 23C.

B. FFT of Autocorrelated Signals

In a second general method for determining spectral-feature scores, time-domain signals recorded at a selected noise are autocorrelated, and a fast Fourier transform (FFT) of the autocorrelated signal is used to generate a spectral-features plot, that is, a plot of the signal in the frequency domain. The FFTs are then used to score the number of spectral signals above an average noise level over a selected frequency range, e.g., DC to 1 kHz or DC to 8 kHz.

FIG. 24 is a flow diagram of steps carried out in scoring recorded time-domain signals according to this second embodiment. Time-domain signals are sampled, digitized, and filtered as above (box 402), with the gain on the noise level set to an initial level, as at 404. FIG. 25A shows a typical time domain signal for a sample compound, in this case the herbicide glyphosate (RoundupR), the segment shown here being taken over the time interval 14.08 to 14.16 seconds. The time-domain signal is then autocorrelated, as at 408, using a standard autocorrelation algorithm, and the FFT of the autocorrelated function is generated, as at 410, using a standard FFT algorithm.

Using the FFT plot, such as shown in FIGS. 25B-25D, the plot is scored by counting the number of spectral peaks that are statistically greater than the average noise observed in the autocorrelated FFT, as at 414. This process is repeated, through the logic of 416 and 406, until a peak score is recorded, that is, until the score for a given signal begins to decline with increasing noise gain. The peak score is recorded, at 418, and the program or user selects, from the file of time-domain signals at 422, the signal corresponding to the peak score (box 420).

The series of autocorrelated FFT plots in FIGS. 25B-25D illustrate the signal analysis involved in this method. At a noise level of 70.9-dbm (FIG. 22B), very few peaks above background noise are observed (the highest spike represents 60 cycle noise). At the optimum noise level of 74.8-dbm (FIGS. 25C and 25D), which represent different recordings at the same noise level), numerous peaks statistically greater than everage noise are observed throughout the frequency range of DC-8 kHz. Several of these peaks are less prominent or have disappeared at the higher noise gain of 78.3-dbm.

When the spectral-features scores for these signals are plotted as a function of noise setting, as shown in FIG. 26, the peak score in the noise setting of about 75-dbm is observed. From this plot, the time-domain signals corresponding to one or the peak score is selected.

As above, this embodiment may be carried out in a manual mode, where the user manually adjusts the noise setting in increments, analyzes (counts peaks) from the FFT spectral plots by hand, and uses the peak score to identify one or more optimal time-domain signals. Alternatively, one or more aspects of the steps can be automated.

C. Averaged FFTs

In another embodiment for determining spectral-peak scores, an FFT of many, e.g., 10-20 time domain signals at each noise gain are averaged to produce a spectral-peaks plot, and scores are calculated as above.

FIG. 27 is a flow diagram of steps carried out in scoring recorded time-domain signals according to this third embodiment. Time-domain signals are sampled, digitized, and filtered as above (box 424), with the gain on the noise level set to an initial level, as at 426. The program then generates a series of FFTs for the time domain signal(s) at each noise gain, at 428, and these plots are averaged at 430. Using the averaged FFT plot, scoring is done by counting the number of spectral peaks that are statistically greater than the average noise observed in the averaged FFT, as at 432, 434. This process is repeated, through the logic of 436 and 437, until a peak score is recorded, that is, until the score for a given signal begins to decline with increasing noise gain. The peak score is recorded, at 438, and the program or user selects, from the file of time-domain signals at 442, the signal corresponding to the peak score (box 440).

As above, this method may be carried out in a manual, semi-automated, or fully automated mode.

IV. Forming Transducing Signals

Signals for various therapeutic uses, or for uses to otherwise effect biological systems, may be generated directly from processed time-domain signals. Signals may also be formed by constructing a signal having specific identified peak frequencies. For example, the system can take advantage of "signal-activity relationship" in which molecular signal features, e.g., characteristic peak frequencies of a compound, are related to actual chemical activity for the compound, analogous to structure-activity relationships used in traditional drug design. In one general application, signal-activity relationships are used for drug screening, following, in one example, the following method.

First, one or more compounds having desired activity are identified, e.g., compounds capable of producing a desired response in a biological system. The system records a time-series signal for one of these compounds, and the wave form is processed or otherwise optimized to identify low-frequency peaks for that compound. ("Low-frequency" in this case refers to peaks at or below 10 kHz.) The steps are repeated for each of a group of structurally related compounds. The structurally related compounds include those that are active (produce a desired response), and some that are inactive for the tested biological response. The spectral components of the two groups of compounds are compared to identify those spectral components that are uniquely associated with compound activity. For example, by analyzing forms from three active and two inactive compounds, one may identify those peaks in the signal found in the active compounds, and not in the inactive compounds, some of which are presumed to provide the desired biological response.

In like manner, the system may record and optimize any unknown compound. One may then analyze the resulting wave form with signals associated with known compounds to see if the unknown compound displays structural features associated the desired activity, and lack components associated with inactive components to help identify an active compound. Rules derivable from signal-structure relationships are more accessible and more predictive than rules derived from structure-activity relationships, since activity can be correlated with a relatively small number of peak frequencies, rather than a large number of structural variables. Thus, for use in drug design, one can use the presence or absence of certain peak frequencies to guide synthesis of drugs with improved pharmacokinetic or target activity. For example, if poor pharmacokinetic properties, or an undesired side effect, can be correlated with certain peak frequencies, novel compounds that lack or have reduced amplitudes in these frequencies would be suggested. As a result, the inventive system greatly simplifies the task of formulating useful drug-design rules, since the rules can be based on the relatively small number of peak frequencies.

A large database of spectral peak frequencies representing numerous compounds would allow one to combine signal features to "synthesize" virtually any drug or drug-combination property desired. By combining this database with a chemical compound database, one may generate chemical structures that display a desired peak-frequency set. This approach would be similar to current computer-assisted chemical-synthesis programs used to generate compound syntheses for novel compounds of interest.

The system can employ numerous signal processing techniques, as described herein. For example, signals from two or more structurally-related compounds can be compared with one or more signals from a structurally-related, but inactive or undesirable compound to identify only the desired frequency components between the signals. A resulting signal may thus be constructed that includes only the desired peaks. By then generating a time-domain signal, that time-domain signal may be used for therapeutic purposes.

Of course, a time-domain signal may be generated from the processed frequency-domain signal of a single compound.

For example, one may obtain the frequency-domain signal for a desired sample, and produce a processed, desired signal. From the processed signal, a time-domain signal may be generated using known techniques, which can then be employed for therapeutic or other uses as an analog to the compound itself.

FIG. 25A shows a typical time domain signal for a sample compound, in this case the herbicide glyphosphate (Roundup®). The segment shown here is taken over the time interval 14.08 to 14.16 seconds. The time-domain signal is then autocorrelated using a standard autocorrelation algorithm, and the FFT of the autocorrelated function is generated using a standard FFT algorithm.

Using the FFT plot, such as shown in FIGS. 25B-25E, the plot is scored by counting the number of spectral peaks that are statistically greater than the average noise observed in the autocorrelated FFT. This process is repeated until a peak score is recorded, that is, until the score for a given signal begins to decline with increasing noise gain. The peak score is recorded and the program or user selects, from the file of time-domain signals, the signal corresponding to the peak score.

The series of autocorrelated FFT plots in FIGS. 25B-25E illustrate the signal analysis involved in this method. At a noise level of 70.9-dbm (FIG. 25B), very few peaks above background noise are observed (the highest spike represents 60 cycle noise). At the optimum noise level of 74.8-dbm (FIGS. 25C and 25D), which represent different recordings at the same noise level), numerous peaks statistically greater than average noise are observed throughout the frequency range of DC-8 kHz. Several of these peaks are less prominent or have disappeared at the higher noise gain of 78.3-dbm (FIG. 25E).

When the spectral-features scores for these signals are plotted as a function of noise setting, as shown in FIG. 26, the peak score in the noise setting of about 75-dbm is observed. From this plot, the time-domain signals corresponding to one or the peak score is selected.

V. Transduction Apparatus and Protocols

This section describes equipment and methodology for transducing a sample with an optimized, low-frequency, time-domain signal, and transduction experiments carried out on three biological samples. Detailed protocols for generating an optimized agent-specific signal are given in Example 1. The samples that are transduced are one which show a well-characterized and easily detectable response to a chemical or biochemical agent, and the transducing signal is an optimized, time-domain signal of the chemical or biochemical agent. Detailed protocols used in the transduction experiments for each of the Ara/lac operon system are given in Examples 2. Similar methods were used in the other two biological-response systems.

FIG. 28A shows the layout of equipment for transducing a sample with an agent-specific signal, in accordance with the invention. The particular layout accommodates five different samples, including three samples 444, 446, and 448 which are held within transductions coils, and exposed to electromagnetic signals, a sample 450 that serves as a control, and a sample 452 that serves as a chemical-induction control. As seen in FIG. 28C, the sample samples are typically held on a shaker table and maintained there, during the induction period, under identical shaking, temperature, and humidity conditions.

Transduction by an agent-specific signal is carried out by "playing" the optimized agent-specific signal to the sample, using, where the signal is recorded on a CD, and is played on a CD recorded 454 through a preamplifier 456 and an audio amplifier 458. This signal is supplied to the electromagnetic coils 444 and 446 through separate channels, as shown. In one embodiment, a Sony Model CDP CE375 CD Player is used. Channel 1 of the Player is connected to CD input 1 of Adcom Pre Amplifier Model GFP 750. Channel 2 is connected to CD input 2 of Adcom Pre Amplifier Model GFP 750. CD's are recorded to play identical signals from each channel. Alternatively, CD's may be recorded to play different signals from each channel. The coil in sample 448 is used primarily to produce a white noise field as a control for experiments. For example, a GR analog noise generator provides a white Gaussian noise source for this coil. Alternatively, this coil can be used to play any pre recorded transduction signal via a second Crown amplifier.

The cabling between the CD player and pre amplifier is standard RCA audio patch cable (6 foot). The Adcom Pre Amplifier Model GFP 750.receives the output from the Sony CD player and amplifies it sufficiently to drive the Crown amplifier. Alternatively, the pre amplifier may also be configured to receive transduction signals from other sources such a Sound Blaster PC board. Cabling between the pre amplifier and Crown amplifier is standard RCA audio patch cable fitted with an RCA to ¼ phone plug at one end of each cable (3 foot) for connecting to the Crown amplifier. The Crown Amplifier Model Micro-Tech 2400, Stereo (1000 watts per channel) receives the signals from the pre amplifier and boosts signal levels sufficient to drive the transduction coils. Cabling between the Crown amplifier and the transduction coils is 14 gauge stranded copper audio cable with banana plugs at each end. Banana plugs are mechanically connected to the cable with set screws.

Chemical induction control samples were placed inside a VWR compact incubator with shaker table and maintained at the same temperature as transduction coils.

FIG. 28B shows sample transduction equipment 466 such as represented by any of samples 444, 446, and 448 in FIG. 28A. The equipment includes a chamber 468 housing an electromagnet 470, and various probes for monitoring conditions within the chamber, e.g., temperature. The electromagnet sits on a base 474, and includes, conventionally a toroidal ferromagnetic core and wire windings.

In one embodiment, the coils are engineered and manufactured by American Magnetics to provide uniform performance between coils. Each coil consists of 416 turns of #8 gauge (awg) square copper magnet wire, enamel coated, about a 2" air core. Each coil can produce approximately 1500 Gauss in the center at 10 Volts RMS at 10 Amps RMS at 11 Hertz without exceeding a 15 degree Celsius rise in temperature. No induction control samples were placed inside a VWR compact incubator with shaker table and maintained at the same temperature as transduction coils.

The coil is supported on a two inch tall by four inch wide PVC support 474. A series of 1⅞ inch OD PVC tubes are cut to different vertical dimensions to facilitate positioning samples in the center of each coil. Samples are inserted through the top of the coil and rest on the PVC positioning tube (not illustrated). Coils and bases are secured to the floor of the enclosure with fast drying epoxy. Connection between the coil posts and RF input connectors is provided by mechanically connecting a four inch long piece of 14 Gauge copper stranded wire to the coil with aluminum bolts, nuts and washers. The other ends are soldered to the RF input connectors with 60% solder. RF probes are made of a single six inch length of 12 gauge copper wire soldered to the insulated center post of a male BNC connector. RF probes are connected to a Stanford Research Systems Model SR 785 2 Channel Dynamic Signal Analyzer using RG 6 coaxial cable installed with BNC connectors at each end.

A Sensatronics Model E4 temperature monitor is used to monitor the temperature of all three coils and incubator. Sensors are taped to the wall of each shielded enclosure and to the inside wall of the incubator. (Probes are Sensatronics Standard model temperature probes.) Probe cabling was supplied by Sensatronics to match the probe and monitor.

FIG. 28C shows a shaker table arrangement in which three sample chambers, such as chamber 466, are supported on individual shaker tables, such as table 486, all carried on a support table 488 within a shielded chamber or enclosure 490 which is maintained at a constant temperature and humidity during a transduction experiment.

The shielded enclosure is, for example, 10×10×10 inches in dimensions and formed of 125 inch 6061 T6 Aluminum plate, such as one manufactured by Rowe Air Manufacturing, Marysville, Wash.

In a second general embodiment, illustrated in FIG. 29A, the transduction coil is a Helmholz coil. The ideal Helmholtz coil consists of two coaxial circular current loops with the same radius, separated from each other by one radius. In other words, the loops are I apart, such that I=r. The magnetic field $B_x$ produced by the coils, in teslas, at any point on the axis of the Helmholtz coil is given by the following equation, where the direction of the field is perpendicular to the plane of the loops.

$$B_x = \frac{\mu_0 i}{2r}\left[\frac{1}{\left(\gamma^2 + \gamma + \frac{5}{4}\right)^{3/2}} + \frac{1}{\left(\gamma^2 - \gamma + \frac{5}{4}\right)^{3/2}}\right]$$

In this equation, m 0 is the permeability constant (1.26× 10-6 H/m), i is the current in the wire, in amperes, r is the radius of the current loops, in meters, and g is the ratio, x/r, where x is the distance, on axis, from the center of the Helmholtz coil, and r is the radius of the coil.

As can be seen from FIG. 29A, the field created by each coil adds to give a relatively large uniform field at the center of the coil. The coils could also be square or rectangular, where the coil separation is such as to create a uniform filed between the coils, according to known principles.

FIGS. 29B and 29C show alternative transduction coils suitable for use in the invention. The transducer 494 in FIG. 29B is a long solenoid, e.g., up to several feet in length. The field inside the solenoid is parallel to the axis of the solenoid and constant within the solenoid, going to zero outside the solenoid (in an approximation of an infinitely long solenoid). This finite length coil will have a substantially uniform field only near its center. Thus, by placing the sample at the center of the coil, a substantially uniform magnetic field is created at the sample when the coil is energized with the MIDS signal.

By adding additional turns to the solenoid, such as additional turns 500 in solenoid 496 in FIG. 29C, additional field strength can be added at the ends of the coil to compensate for the fall off of the coil's magnetic fields at its ends.

In still another embodiment, the transduction coil may be a small implantable ferromagnetic coil, in this case a vascular stent coil capable of receiving transducing signals either by electrodes attached to opposite ends of the coil or by a remote, inductive system in which an electromagnet is placed near the body surface, against the patient's chest, and signals are transmitted inductively to the implanted coil.

VI. Transduction Experiments

The sample/agent systems used for the transduction experiments include (1) an arabinose-inducable bacterial system having a lac operon that is inducable by L-(+) arabinose (+); (2) sugar pea plants whose stem length growth can be are inhibited by the presence of the herbicide glyphosphate, and (3) sugar pea plants whose stem length growth can be stimulated by the plant hormone gibberellic acid.

A. Induction of Bacterial Lac Operon by L(+) Arabinose

The arabinose operon in bacteria is a tightly regulated system consisting of a promoter under control of a gene product, araC and it's cognate inducer, L-arabinose, a sugar. Heterologous protein expression can be tightly controlled using plasmids with arabinose and the araC gene, which is both a positive and negative regulator of the promoter. The mechanism of induction involves an allosteric change in the binding characteristic of the araC gene to DNA elements upon ligation of arabinose.

The chemical sensor system chosen for this study is known to be selective for the L(+) arabinose form, while the D(−)-arabinose does not induce araC—PBAD promoter dependent induction and expression of the reporter GFP uv protein, despite their identical empirical formula and similar structures. Therefore, this system and related compounds provide an ideal set of tools to assess the specificity of the any gene expresssion transduced via playback of the recovered molecular emission signals (MIDS) characteristics of these similar molecules Optimized signals for both L(+)Ara and D(−)Ara were generated as detailed in Examples 1 and 2. Briefly, signals were optimized for stochastic resonance products by varying the injected noise levels, and physical concentration of material used for signal recovery. Comparison of optimized SR signal products derived from measurements of equimolar solutions of arabinose isomers were significantly different. The recovered MIDS signals were judged to be significantly different and distinct for the two different arabinose isomers. These results suggest that recovered molecular emission signals are sensitive to the chemical structure of these two molecules of identical chemical composition and empirical formula. These two isomers differ only in the cis-trans disposition of the four hydroxyl groups attached to the hexose ring.

Figure 30A:
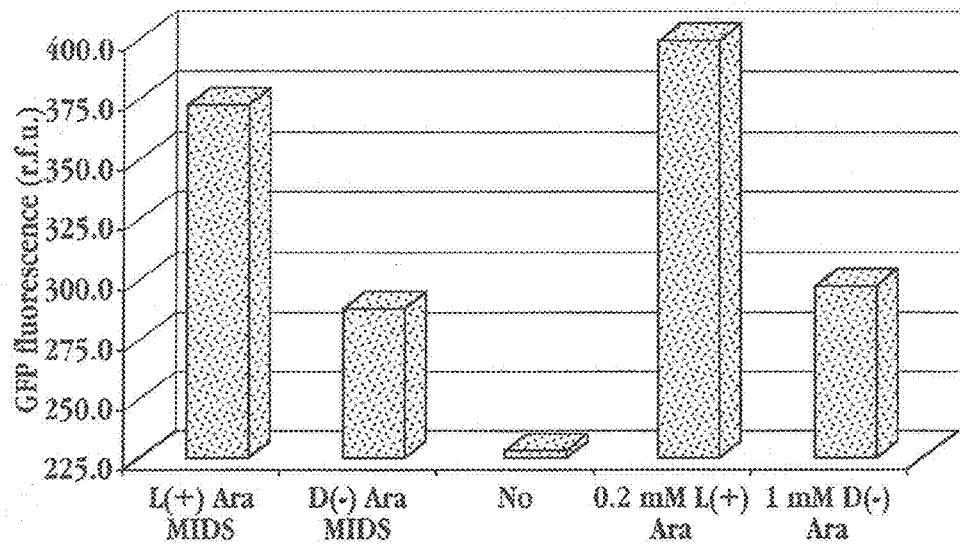
Figure 30B:
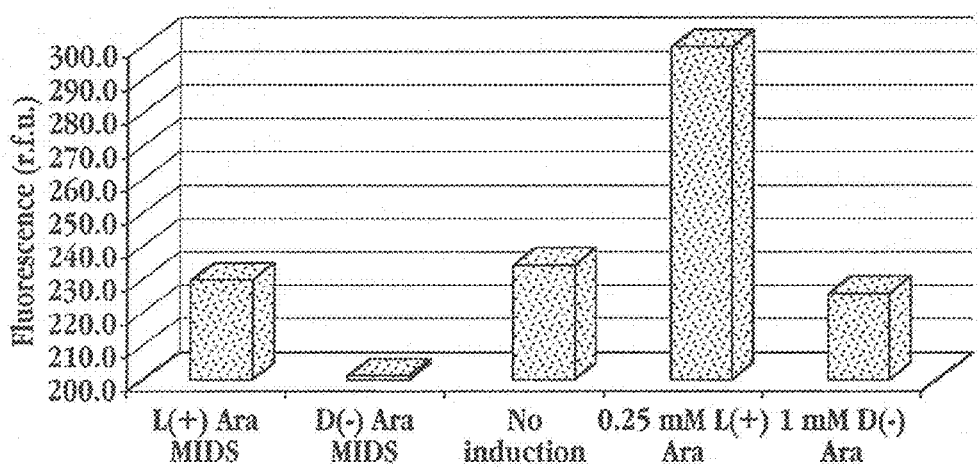

The bacterial samples were exposed to the MIDS signals for both L(+)Ara and D(+)Ara, employing the transduction setup and protocols detailed in Example 2. The OD measurements data for five independent experiments are given in the examples, and plotted in FIGS. 30A-30E. The plot in FIG. 30A shows the induction in GFP in response to MIDS signals and to the chemical agents themselves. As seen, the MIDS L(+) Ara signal was comparable, inn its induction effect, to 0.2 mM L(+) Ara, and substantially greater than the response to either the D(−) Ara MIDS signal or to the D(−) Ara compound. Little induction was seen in the absence of either an MIDS signal or Ara compound. The data plotted in FIG. 30B illustrates a similar effect, with respect to the two MIDS signals. In these first two experiments, only 2 coils were used. The non-MIDS controls were placed independently in an incubator, but without shaking, and the incubator temperature was matched manually to those of the coils. The coils heated resistively at the voltages and currents used. Therefore a relative difference measurement was used between the L(+) and D(−) MIDS samples. The controls simply indicate correct chemical response of the system, and are not used in the quantitation.

Figure 30C:
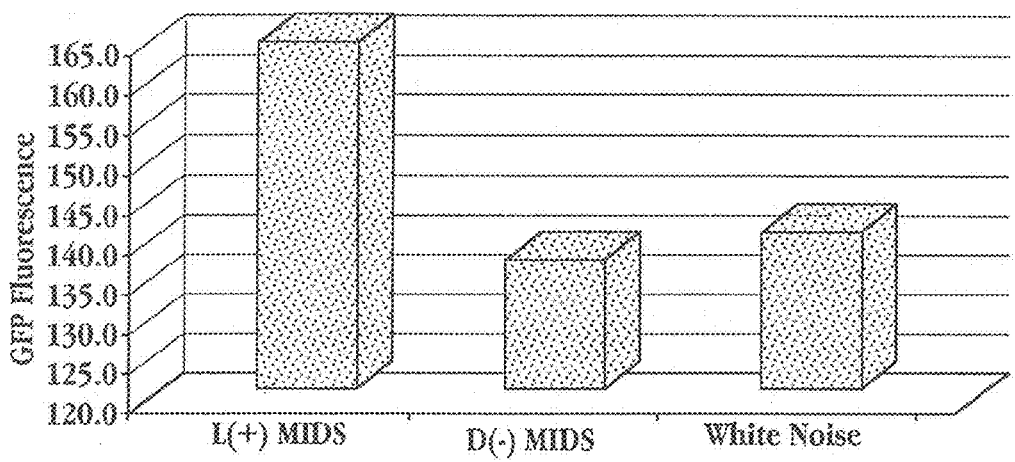
Figure 30D:
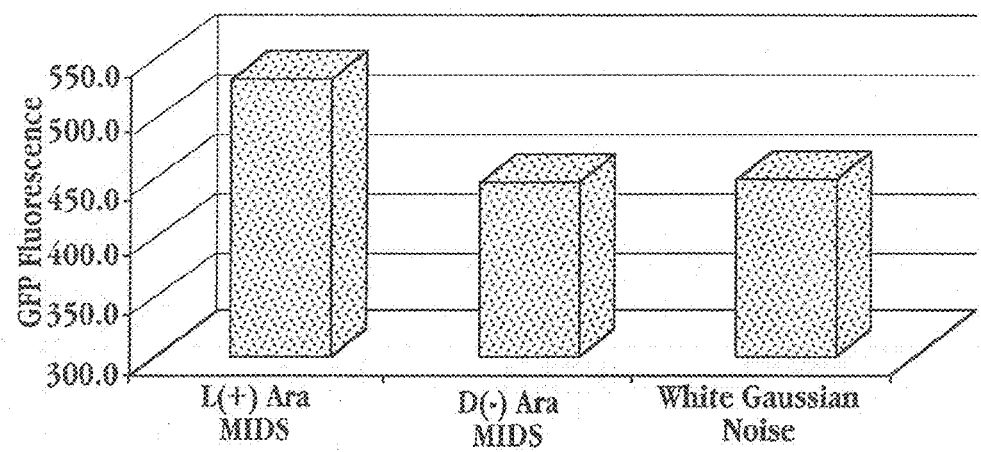
Figure 30E:
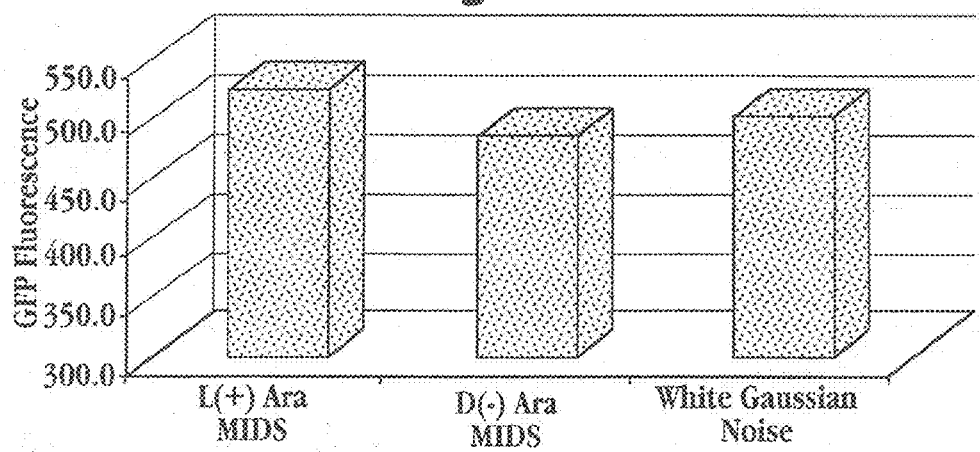

The three experiments plotted in FIGS. 30C-30E all show: substantially greater induction with the L(+) MIDS signal than with either the D(−) MIDS signal or the white-noise control. The underlying data is given in Example 2.

These data demonstrate a specific transduction of the araC-$P_{BAD}$ operon with the MIDS signal recovered from the cognate chemical inducer L(+)-arabinose, but not the inactive chemical isomer D(−) arabinose. This system presents a good model for specificity of the transduction effect as the reference chemicals are identical in composition, but only different stereochemically. Clearly the biological system is selective for the structures. In the experiments conducted, continuous overnight playback yields a fairly consistent 15-20% relative induction of L vs D MIDS signal. In one experiment, a shorter induction period of 3.5 hrs used in chemical induction protocol of Surestha et al., resulted in an apparent relative induction of 7.8%, and close to background levels.

Under the experimental conditions, both growth and induction obtain for a fairly long period. These data are consistent with the notion that the MIDS playback can affect the operon turn-on pathway to effect specific induction of a gene. A possible locus of action may be in the L(+) ara MIDS interacting with the araC protein to induce it to mimic the L(+) arabinose bound state, which can then lead to gene induction. This model does not require any formation of chemical bonds but might rather affect the system allosterically.

B. Inhibition of Stem-Cell Growth by a Herbicide

The monomeric enzyme 5-enolpyruvylshikimate-3-phosphate (EPSP) synthase (EPSPS) is one of two enzymes in the class of enolpyruvyltransferases. Ligand binding converts the enzyme from an open state to a tightly-packed closed state, following the pattern of an induced-fit mechanism. EPSP synthase is involved in the shikimate pathway, using phosphoenolpyruvate (PEP) to convert shikimate-3-phosphate (S3P) to 5-enolpyruvyl-3-shikimate phosphate, a precursor to the majority of aromatic compounds produced in the cell, including the aromatic amino acids. It has been reported that the compounds produced in this pathway constitute as much as 35% or more of the dry mass of plants. The fact that this enzyme does not occur in mammals, fish, reptiles, birds and insects makes it a good target for antibiotics and herbicides.

The synthetic compound glyphosate (N-phosphonomethylglycine, the active ingredient in the herbicides Roundup™ is as a competitive inhibitor to this enzyme and effectively shuts down aromatic amino acid biosynthesis and also synthesis of other aromatic compounds derived from these amino acids. Glyphosphate is a transition state analog which binds to the PEP-binding site (the phosphate and formate ions mimic the active groups of the PEP oxocarbenium ion). Glyphosate displays high specificity for EPSP synthase, not even binding to UDP-N-acetylglucosamine enolpyruvyltransferase (MurA), the only other enzyme in the enolpyruvyltransferase class.

The optimized inherent (MIDS) emission signals of glyphosphate were obtained as described in Sections II and III above, using system equipment and protocols as detailed in Examples 1 and 2 below. In one experiment, an optimized glyphosphate MIDS signal was applied to pea sprouts supported on a moist medium, with signal application over a 72 hour period at 37° C., 100% humidity. Various controls included (1) no signal, (2), the chemical Roundup®, and (3) a white noise signal. Stem length was measured within a hour after exposure to the stimulus, and 5-50 sprouts were contained in each group.

FIG. 31 shows a bar graph plot of stem lengths in each of the four experimental groups, where the upper and lower boundaries of each bar represent stem-length maxima and minima, respectively, and the intermediate line represents stem-length average for that group. As seen from the figure, both chemical glyphosphate and the glyphosphate MIDS signal were effective in substabtially inhibited stem growth in the plants, whereas the white noise control had little or no effect on stem growth.

FIGS. 32A and 32B provide more graphic evidence of the effect of the glyphosphate MIDS signal on pea sprout samples. FIG. 32A is a photograph of 72-hour old pea sprouts, in the absence of any chemical or MIDS-signal treatment. Pea sprouts of the same age, but taken within one hour after exposure to the stimulus, show evident signs of disrupted and abnormal growth.

C. Stimulation of Stem-Cell Growth by Gibberellin

The ability of a time series electromagnetic signal to mimic the bio-activity of a specific bio-active molecule was also demonstrated made with Sugar Pea Sprouts using Gibberellic Acid-3 (GA-3). Gibberellic Acid (known also as Potassium Gibberellate, or Mega Grow) is a naturally occurring plant growth regulator which may cause a variety of effects including the stimulation of seed germination in some cases. GA-3 occurs naturally in the seeds of many species and is produced commercially by growing *Gibberella Fujikuroi* fungus cultures in vats, then extracting and purifying the GA-3. Presoaking seeds in GA-3 solution will in many cases cause the rapid germination of many types of highly dormant sees which would otherwise need cold treatment, after-ripening or aging, or other prolonged pretreatments.

A quantity of the growth regulator gibberellic acid (0.001%) was placed in a 1.5 cc Pyrex sample vial and placed in close proximity to a $1^{st}$ derivative super conducting gradiometer. White Gaussian noise current in the frequency range DC to 2000 Hz was broadcast via a 16 turn Helmholtz coil producing a magnetic field, with the B-Field oriented normal to the axis of a gradiometer. This noise signal is presumed to promote the formation of a stochastic signal characteristic of the molecular electromagnetic (magnetic) emission of gibberellic acid as measured by the gradiometer. The stochastic signal was recorded and stored in WAV format, as described above. Each signal was provided a unique control number.

The signal of the growth regulator recorded as above was post processed to identify spectra unique only to the agonist, and converted to a WAV file through the use of an IFFT. Five study groups were created, each consisting of live sugar pea sprouts obtained from Sun Grown, Inc., San Diego. Each study group was prepared by placing the sprouts on wet paper towels in such a way to promote the sprouting of the sugar peas.

The five groups were: (1) Non-Impact Control Group (sprouts germinate naturally, provided adequate light, water and ventilation); (2) Growth Regulator GA-3 Group (sprouts are treated with the growth regulator); (3) White Gaussian White Noise applied via a noise coil; (4) Growth regulator Emission Group (The recorded growth regulator from Step 1 was played to the sprouts; and (5) Growth regulator Emission Group (Noise Removed—IFFT, that is, the recorded growth regulator signal was post processed to include only spectra unique to the agonist, then played back to the sprouts).

The signal source is the WAV file created in Step 1, was converted to analog and amplified by a low frequency RF amplifier configured to provide a signal of adequate strength and quality to a hand wound 4 inch (ID) Tesla coil; Groups 3, 4 and 5 were positioned above the transducer. Adequate electromagnetic shielding was used to isolate one group from another. Adequate light, heat and ventilation was provided to facilitate healthy growth for all groups.

The Duration of each study was be 72 hours unless dynamic results were achieved earlier. The signal characteristics for each group are:

| Group 3 | |
| --- | --- |
| Signal Type | Gaussian White Noise |
| Bandwidth | DC - 2 kHz |
| Filtering 2 kHz | 4 pole Butterworth low pass filter with 3 db roll-off at 2 kHz |

| Group 4 | |
| --- | --- |
| Signal Type | SQUID Output Signal |
| Bandwidth | DC - 5 kHz |
| Filtering | None |

The transducer was an 18 inch diameter modified Helmholz, with the sprouts centered in coils core.

The results of the study are plotted in FIG. 33, showing average stem lengths for groups 1-4 above. As seen, The MIDS signals for gibberellic acid (Group 4) produced a significant increase in average stem length over the free-growth control (Group 1), white noise (Group 3), and even gibberellic acid (Group 2).

D. Inhibition of Proteosome Activity by Phepropeptin D

The 20S proteasome enzyme is activated with a mild detergent (SDS). The cleavage of the substrate Suc-Leu-Leu-Val-Tyr-AMC by the activated enzyme liberates the fluorescent AMC molecules that can be monitored by exciting AMC at 380 nm and detecting the fluorescence at 460 nm. Proteosome activity is inhibited by phepropeptin D.

In a first study, the ability of phepropeptin D and a MIDS signal of phepropeptin D to inhibit proteosome activity, as measured by the appearance of conversion of the substrate Suc-Leu-Leu-Val-Tyr-AMC to yield a fluorescent signal were measured, following substantially the same methodology described above and in the examples.

The 20S Proteasome assay kit (EMD Biosciences Cat #539158) was adapted for use in a cuvette format with a final volume of 200 µl. Nine samples were set-up using the following procedure:

Reaction buffer (20×) was diluted, 100 µl with 880 µl of HPLC grade water and 20 µl of 100× activation buffer to a final volume of 1 ml.

100 µl of the diluted 2× reaction buffer was added to each of the no enzyme control tubes.

The 20S proteasome enzyme was added to the remaining solution, 3.2 µl to 800 µl of 2× reaction buffer and 100 µl added to each of 7 remaining tubes.

To each tube 100 µl of water or water and inhibitor were added.

In a separate tube 4 µl of the substrate was diluted with 96 µl of HPLC grade water and 10 µl/tube of the diluted substrate was added to each of the reaction tubes to obtain a final volume of 200 µl.

Samples were all mixed by repeated pipetting and the reactions incubated at 37 C for 2 hrs. MIDS field exposed samples were incubated within the helmholtz coil partially submerged within a 37 C water bath broadcasting a 60 mG AC field of Phepropeptin D.

Fluorescence was quantiated and recorded using a fluorometer (Turner Designs, Sunnyvale, Calif.—Model TD-700).

Samples with two replicates are indicated with an asterisk above the graph.

The samples were:
1 24.91 (Disc) No enzyme control (negative control)
2 697.9 (Disc) No inhibitor (positive control)
3 25.83 (Disc) Chem. inhibitor ALLN
4 105.6 (Disc) Chem. inhibitor Phepropeptin D
5 79.35 (Disc) Chem. inhibitor Phepropeptin D+MIDS Phepropeptin D (60 mG)
6 251.1 (Disc) MIDS Phepropeptin D (60 mG)
7 519.3 (Disc) No inhibitor (positive control)
8 21.96 (Disc) No enzyme control (negative control)
9 209.7 (Disc) MIDS Phepropeptin D (60 mG)

The results of the study are given in FIG. 34. The positive control sample #2 was set to 700 and all other measurements were taken relative to that sample. The chemical inhibitors inhibited the activity of the 20S proteasome to less than 20% of the uninhibited activity. The MIDS field derived from the Phepropeptin D sample decreased the activity of the 20S proteasome enzyme to less than 36%.

In a follow-up study, samples were allowed to incubate at room temperature overnight to determine if the substrate would continue to be converted to the fluorescent product. If the MIDS signal inhibited the 20S proteasome and the enzyme remained active after being removed from the field, the activity of the MIDS-exposed samples should increase relative to the other samples containing chemical inhibitors consistent with the no inhibitor control.

The results, given in the table below, show that the positive control continued to increase as indicated by the decrease in the sensitive level for the fluorimeter. The activity of the chemical inhibitors became more pronounced relative to the positive control which continued to increase. The MIDS sample was the only sample in which the activity increased, indicating that the inhibition initially detected following the 1 hr 30 min incubation was no longer present after the sample was removed from the field.

| | % Normalized Fluorescence | |
| --- | --- | --- |
| | 1 hr 30 min | 20 hrs post |
| Neg control | 0 | 0 |
| Pos control | 100 | 100 |
| ALLN | 4.97479 | 2.645832 |
| Phe D | 18.12605 | 16.97173 |
| Phe D + MIDS | 34.63866 | 27.7141 |
| MIDS | 38.45378 | 66.3626 |

E. Treatment of Cancer

This study assessed the growth inhibitory potential of a transduced molecular emission signal of taxol, in a standard mouse xenograft model of a human breast tumor. Taxol is a clinically proven cytotoxic agent that works specifically by non-covalently binding to tubulin subunits in cytoskeletal elements composed of polymerized tubulin, preventing their disassembly, thus arresting cell division and triggering apoptosis. Taxol therefore has allosteric effects on a protein monomer that has propagating effects downstream of the initial binding event, that affect larger macromolecular structures. The cytoxic effect is more pronounced in rapidly dividing cancer cells. Taxol's mechanism of action does not require covalent bond making or breaking subsequent to binding to the target tubulin molecule.

Method: MIDS measurement was made in glass sample holders (Kimble autoinjector vials) on (1) neat solution of the preformulated taxol clinical vial, using a 1 ml tuberculin syringe, and 22G needle, to withdraw 0.7 ml from multidose vial (preserve sterility and integrity of solution, so don't syringe back in), then (2) this 0.7 ml taxol formulation will be used to dissolve additional 1 mg vials of taxol, to increase the amount of taxol relative to Cremophor®. The study was designed to evaluate the efficacy of a transduction technology to inhibit tumor growth in an in vivo human tumor mouse xenograft model, and to compare its effect to a standard chemotherapeutic treatment-taxol. 5 million MDA-MB-435 cells, in suspension, were subcutaneously injected into the flanks of athymic nude mice. Treatment began the same day of cell implant (Day 1). Animals were assigned to one of 4 groups. Each animal was monitored for tumor growth twice per week for the duration of the study. One group was treated with Taxol, Two groups were treated with transduction and one group was treated with the taxol vehicle to act as a control.

The mice were athymic nude mice nu/nu with a BALB/c background. Implanted with 5 million of breast cancer tumor line MDA-MB-435(NCI standard originally from the NCI) from American Culture Type Collection, ATCC (Rockville, Md.). This is a mammary duct carcinoma that is non-estrogen dependent for growth. Additional specifics are at: http://www.atcc.org/SearchCatalogs/longview.cfm?view=ce, 5361826,HTB-129&text=breast&cancer&max=20—

Conventional treatment groups (10 mice each): vehicle only, taxol at 15 mg/kg, 2×wk i.p. twice a wk for duration of study, MIDS transduction groups (11 mice each): at two different power levels.

| Group | Agent | Transduction | n |
|---|---|---|---|
| 1 | Vehicle | No | 10 |
| 2 | Taxol | No | 10 |
| 3 | MIDS 40 mG | Yes | 11 |
| 4 | MIDS 60 mG | Yes | 11 |

The mice were confined to a 2-ft diameter right-angle cylinder, with coil windings designed by Tristan Technologies, which accommodated a standard mouse cage so that mice were constantly exposed to the MIDS playback of taxol. All mice in a treatment group were housed in one cage and kept within the area of the central cylindrical cavity of the large transduction coil under continuous playback, while they were fed and watered. During the period where tumor volume measurements were made and when the cages were cleaned, the cages were slid out of the coils. This should have resulted in a continuous exposure duty time of about 80-90% of the study duration.

Comparison of individual animal tumor volumes revealed that tumor growth was statistically significantly inhibited at the completion of the study (Day 36). Outliers, defined as values that exceeded the range of two times the standard deviation, were removed from all groups prior to statistical analysis. On day 36, the taxol, 40 mG and 60 mG treatments inhibited growth by 43%, 36% and 38%, respectively. A comparison of the 40 mG and 60 mG treatments to the standard chemotherapeutic agent, taxol revealed no difference between the treatments, suggesting that the 40 mG and 60 mG treatments exhibited similar efficacy as the taxol treatment, with the outliers removed.

In summary, both the 40 mG and 60 mG treatments showed similar efficacy with no adverse clinical signs in the MDA-MB-435 human breast tumor model. Statistical significance was achieved with both treatments when comparing tumor volumes and tumor weights after 36 days to the vehicle control. However, including two outliers from the 60 mG treatment and one from the 40 mG treatment in the statistical analysis would eliminate the statistical significance. A comparison of both the 40 mG and 60 mG treatments with the taxol treatment revealed no significant differences, suggesting similar efficacy after 36 days of treatment.

The following examples to illustrate various methods of the invention, but are in no way intended to limit the scope of the invention.

Example 1

Protocol for Signal Acquisition and Autocorrelation of Low Frequency Molecular Electromagnetic Emissions At the time of measurement, sample materials are at room temperature between 70 to 74 degrees F. Wide variations in sample temperature may shift emissions to higher or lower frequencies depending on increases or decreases in temperature. If samples are to be recorded above or below room temperature, the temperature of the material prior to, and after measurement shall be recorded, and the means for heating or cooling shall be noted.

If the material to be measured is exposed to room air, atmospheric humidity shall be recorded at the time of measurement. If the material to be measured is exposed to room air, the barometric pressure shall be recorded at the time of measurement. If the sample is pressurized, the pressure shall be recorded in pounds per square inch, or inches of mercury.

Environmental electromagnetic interference shall be recorded prior to and after molecular measurements are taken. This data may be subtracted from the sample data during post processing.

A. Sample Preparation
  Sample Size: 0.8 to 1.5 cc
  Sample Container: 1 cc or 2 cc Pyrex flat bottom vial.
  Sample Storage Samples are securely maintained for multiple measurements under varying conditions. Samples are stored in their original Pyrex sample vials with non reactive screw caps tightly applied.
B. SQUID Parameter Setup
  Cooling: All cryogenic components are brought to an operating temperature of 4 Kelvin.
  Power Up: The SQUID and SQUID controller are powered up and internal tests are performed to insure proper operation.
  Tuning: The SQUID is tuned for optimal operation (0.4-0.8 micro volts output without white noise injection).
  Gain: 100×
  DC Offset: ZERO
  Bandwidth: Normal (50 kHz)
  Filter: 0.3 Hz (high pass)
C. Noise Generator
  Signal Type: Analog White Gaussian Noise, or uniform noise (constant amplitude)
  Output Voltage: from minimum to maximum open-circuit output voltage 3 volts rms minimum. The applied output voltage is initially set to zero output.
  X channel: Connected to Helmholtz coils for noise injection.
  Y channel: (inverted) Connected to noise cancellation coil in series with gradiometer prior to the SQUID input coil. (optional)

Output Impedance: 50 ohms

D. Spectral Analysis

The analog signal output from the MIDS (Molecular Interrogation and Data System) is acquired through a PCI data acquisition board and is stored. WavGrab is also designed to serially interface with a Noise Com model UFX 9837 white noise generator. A sample is recorded multiple times while incrementally increasing the amount of noise applied to the Helm Holtz coils with each subsequent recording. A series of recordings is thus made of a single target sample at various noise levels. Alternatively, a manual method for signal acquisition may be used.

E. Stochastic Generation

The sample stage is withdrawn from the SQUID detector. (No Sample). A small amount of gain is applied to noise generator channel X. The output from noise generator channel Y is adjusted to produce the deepest null possible at the SQUID output (white noise cancellation—Optional). The noise generator's master gain control is reduced to zero. A sample is inserted into the detector by sliding the sample tray into position beneath the gradiometer. The averaged Fourier display is monitored and base line spectra are noted (within bandwidth of interest). The master gain control (noise generator) is incrementally advanced while monitoring the averaged Fourier display for changes in baseline spectra.

When prominent spectral peaks appear that are not representative of baseline spectra, the advancement of noise gain is halted and a time series record of the emission is recorded.

F. Post Processing

Several raw time series recordings of a single molecular target are collected and stored in WAV format. Each recording represents one of a series of recording measurements made over a range of white noise amplitudes. All raw time series recordings obtained from a single molecular target are marked for batch processing. Each raw time series recording within the batch are auto correlated. The autocorrelation function is used for the following two purposes:

A. To detect non-randomness in data.

B. To identify an appropriate time series model if the data are not random.

The auto correlated time series is stored with the raw time series recordings in batch for additional processing. Each auto correlated time series within the batch is converted to the frequency domain using a Fourier transform. For each frequency domain transform an RMS average is calculated over the Y axis (auto correlation score) across all data points within the X axis (Frequency). For each frequency domain transform all Y axis outlier values exceeding the RMS average are tabulated. The tabulated outlier sums for each time series recordings within the batch are written to a spread sheet displaying recording name and outlier count. The time series recordings with the highest outlier scores represent the best recorded signals.

Example 2

Induction of the Lac Operon with an Optimized L(+)Ara Signal

A. Materials

The reporter system for sugar sensing was obtained from a commercial supplier. In this system, bacteria are transformed with a plasmid that consists of the gene for AraC, which acts as an activator of the ara operon, and the gene for a variant green florescent protein, under the control of the $P_{BAD}$ promoter. L-arabinose specifically binds to araC and rapidly turns on transcription in a time dependent fashion reaching a maximum expression level within 3 hr as monitored by intact whole cell fluorescence of the expressed GFP. GFPuv expression is linear with dose over two logs of concentration of L-arabinose (1-500 uM).

A related isomer that an identical chemical composition, but with a different stereochemistry, D-arabinose (non-cognate inducer), does not bind araC, nor activate expression of genes downstream of the $P_{BAD}$ promoter, even at 1000-fold higher concentration than the 100 µM potency of the L-arabinose. The inherent (MIDS) emission signals of L and D-arabinose are obtained as detailed above, employing a 0.1 mM solution of L(+)Ara or D(+)Ara for signal recording, and the autocorrelation/FFT method for identifying optimized time-domain signals.

The specificity and efficacy of gene induction in suspensions of bacteria containing the reporter plasmid, transduced with the cognate and non-cognate MIDS signals were monitored by measuring the whole cell fluorescence of induced green fluorescence, with the results shown in FIGS. 30A-30E, discussed above.

B. MIDS Measurements on Arabinose Isomers:

Concentrated 1.0 M stock solutions of L(+)-arabinose and D(-)-arabinose were prepared. MIDS measurements were made on 0.70 ml of each stock solution in autosampler vials, and signals were recovered according to the signal protocol below.

A small amount of gain was applied to noise generator channel X (noise induction coil and stochastic generation). The inverted output from noise generator channel Y was adjusted to produce the deepest null possible at the MIDS output (white noise cancellation). The noise generator's master gain control was set to zero. A sample was inserted into the detector, and an averaged Fourier display was monitored and base line spectra. The master gain control (noise generator) was incrementally advanced while monitoring the averaged Fourier display for changes in baseline spectra. When prominent spectral peaks appeared that did not representative of baseline spectra, the advancement of noise gain was halted and a time series record of the emission was recorded.

The transduction parameters for the two samples and control sample were as follows:

| | |
|---|---|
| L(+) Arabinose | Signal ID L-Arabinose 1-77.0 |
| Recorded | Jan. 21, 2004 |
| Signal Type | Analog MIDS output signal |
| Bandwidth | DC - 8 kHz |
| Filtering | None |
| File Length | 60 second time series, 1.87 MB |
| Bit Rate | 262 kbps |
| Sample Size | 16 bit |
| Sample Rate | 16 kHz |
| Format | PCM |
| Reference | MB Notebook #1, pg 62, 94 |
| D(-) Arabinose | Signal ID D-Arabinose 1-80.0 |
| Recorded | Dec. 15, 2003 |
| Signal Type | Analog MIDS output signal |
| Bandwidth | DC - 8 kHz |
| Filtering | None |
| File Length | 60 second time series, 1.87 MB |
| Bit Rate | 262 kbps |
| Sample Size | 16 bit |
| Sample Rate | 16 kHz |
| Format | PCM |
| Reference | MB Notebook #1, pg 65, 96 |
| White Noise | Live output |
| Signal Type | White Gaussian Noise |
| Bandwidth | DC - 2 kHz |
| Filtering | 4 pole Butterworth with 3 db role off at 2 kHz |
| File Length | Live continuous signal |

C. Transduction Experiments

Transduction experiments were performed with two sets of coils. In the first system, a pair of coils consisting of 30 gauge aluminum wire was wound around a 3" tall section of PVC core with 2⅝" o.d., wound to 35× the number of windings of starting coils. These were place inside aluminum Faraday boxes 5½×4"×8¾" (W×H×D) to isolate samples for crossover RF signals. Both boxes were placed upon the orbital shaker platform to aerate transducing cultures.

Temperature of samples and coils were monitored with a Craftsman Model 82327 Non-contact Infra-red Thermometer. (a matched RF white noise control was not available at the time of experiments).

In the second set of three 4" tall stock 4000-ft spools of 28G insulated copper wired with 1" i.d. plastic cores were directly used as transduction coils ("Mega coils") and two coils were driven with the MIDS signals, while the third control coil was driven by a random white noise generator. In this case, all three coils were isolated in Faraday boxes, and mounted separated by 2 ft on a 6-ft plank that was fitted to the orbital shaker. This ensured that all three samples were agitated at the same speed with one shaker. Thermistor temperature probes were also place into the core of each coil proximal to the sample to provide real-time reading of temperature. Both sets of MIDS signal coils were driven at the highest input voltage setting until their temperature equilibrated near 94-97° F. from resistive heating of the wound wire. Samples were centered in the core of the coil to experience the maximum and most uniform area of RF flux. (a limitation of the current set-up was the linkage of heating with driving voltages which control RF flux).

In a typical experiment, 1-3 drops of overnight cultures of pBAD-GFPuv transformed JM109 grown in Luria broth containing 100-500 ug/ml of sodium ampicillin (LB/amp) were used to seed 50 ml fresh LB/amp. This was well mixed and 10 ml transferred to 25-ml Erlenmeyer flasks, and 0.1 ml of 100× stocks of reference chemical inducers (D or L arabinose) were added to final concentrations desired. These seeded cultures were placed into either the transduction coils, or left on the shaker platform as controls. (Another limitation of the current set up is the availability of only one shaker table, forcing a choice between incubation at controlled above ambient temperature to match the coils but without agitation, or agitation simply at ambient temperature. Also the matching of the coil temperatures varies about 2-3° F. and cannot be precisely controlled or determined). In most cases the transductions were conducted as overnight incubations.

D. Sample Work-Up and Measurements.

After transduction was stopped, 1.2 ml of bacterial cell culture suspension were transferred to 1.7 ml microcentrifuge tubes and centrifuge 1-2 mins at 12,000 rpm (10,000×rcg). Supernatant broth was removed, discarded and the bacterial pellets re-suspended in 1 ml of ice-cold PBS. Washed suspensions were centrifuged again, PBS wash discarded, pellets re-suspended in fresh PBS, transferred to cuvettes to measure OD600 nm, then volumes were adjusted to match cell density among samples. The fluorescence of these OD matched were obtained by after calibration against a PBS background and setting the fluorescence from a culture chemically induced with 0.1-0.25 mM L(+)-arabinose to 79-90% of full scale units (f.s.u.) of the 1000 fsu of the fluorometer.

While no induction and chemically induced samples (0.1-0.25 mM L(+) arabinose and 1 mM D(−)-arabinose) are prepared, due to current limitations, they were not at the same incubation conditions, and were prepared to verify that the system was 1) still specifically responsive to L(+) and not D(−) arabinose and 2) was used to set the fsu calibration. Due to the lack of a congruent experimental reference for induction overbackground, the differential stimulation of the reporter system by playback of the arabinose isomer MIDS was calculated as: (using the D(−) ara MIDS as the effective background. The other samples are not matched in experimental conditions. It is known that even high concentrations of the chemical D(−) arabinose does not stimulate GFP expression).

For each of the studies reported here, % Relative=[(Fluor. of L(+)ara MIDS)−(Fluor. of D(−)ara MIDS)]

Induction (Fluor. of D(−) ara MIDS).

E. Results

Experiment 1

| Final dilutions | OD 600 nm | | | | |
| --- | --- | --- | --- | --- | --- |
|  | OD1 | OD2 | OD3 | OD4 | Average |
| L(+) Ara MIDS | 0.795 | 0.79 | 0.79 |  | 0.792 |
| D(−) Ara MIDS | 0.778 | 0.804 | 0.79 | 0.798 | 0.793 |
| No | 0.738 | 0.73 | 0.742 | 0.734 | 0.736 |
| 0.2 mM L(+) Ara | 0.753 | 0.766 | 0.77 | 0.767 | 0.764 |
| 1 mM D(−) Ara | 0.785 | 0.764 | 0.783 | 0.782 | 0.779 |

| | Fluorescence | | | |
| --- | --- | --- | --- | --- |
| | rfu1 | rfu2 | rfu3 | Average rfu |
| L(+) Ara MIDS | 372.9 | 372.6 | 373.5 | 373.0 |
| D(−) Ara MIDS | 288.0 | 288.3 | 288.4 | 288.2 |
| No | 228.3 | 228.9 | 228.9 | 228.7 |
| 0.2 mM L(+) Ara | 835.0 | 832.7 | 832.7 | 833.5 |
| 1 mM D(−) Ara | 297.6 | 297.8 | 297.7 | 297.7 |
| Blank | 0.0 | | | |

% Relative MIDS Transduction = (373 − 288.2)/288.2 = 29.4% The results are plotted in FIG. 30A.

Experiment 2: [Notebook TC_003_104&105]

| Cell density: OD 600 nm final dilutions | | | | |
| --- | --- | --- | --- | --- |
| Sample | OD1 | OD2 | OD3 | OD Average |
| L(+) ara MIDS | 0.658 | 0.66 | 0.663 | 0.660 |
| D(−) ara MIDS | 0.646 | 0.656 | 0.655 | 0.652 |
| No induction | 0.645 | 0.6448 | 0.647 | 0.646 |
| 0.25 mM L(+) ara | 0.65 | 0.64 | 0.638 | 0.643 |
| 1 mM D(−) ara | 0.65 | 0.648 | 0.642 | 0.647 |

| | Fluorescence | | | |
| --- | --- | --- | --- | --- |
| | rfu1 | rfu2 | rfu3 | Average rfu |
| L(+) ara MIDS | 230.5 | 230.1 | 229.4 | 230.0 |
| D(−) ara MIDS | 203.2 | 201.4 | 200.6 | 201.7 |
| No induction | 235.2 | 234.9 | 234.8 | 235.0 |
| 0.25 mM L(+) ara | 940.0 | 939.4 | 939.7 | 939.7 |
| 1 mM D(−) ara | 226.7 | 226.7 | 226.1 | 226.5 |

% Relative MIDS Transduction = (203.0 − 201.7)/201.7 = 14.0% The results are plotted in FIG. 30B.

Experiment 3:
Remeasured OD 600 nm after dilutions:

| Sample | OD1 | OD2 | OD3 | OD4 | OD5 | OD Average |
|---|---|---|---|---|---|---|
| L(+) MIDS | 0.839 | 0.853 | 0.847 | 0.846 | 0.841 | 0.845 |
| D(−) MIDS | 0.88 | 0.851 | 0.841 | 0.841 | 0.844 | 0.851 |
| White Noise | 0.839 | 0.836 | 0.85 | 0.834 | | 0.840 |

Used Prior Calibration

Readings were taken in average mode.

Re-CALIBRATE: set L(+) ara MIDS to 700 fs, read at =698, sensitivity factor 54 and was blanked against PBS=50

| | Fluorescence | |
|---|---|---|
| Sample | no calibr | recalibrate |
| L(+) MIDS | 164.0 | 642.1 |
| D(−) MIDS | 136.7 | 540.6 |
| White Noise | 140.5 | 563.0 |

Relative MIDS Transduction = (164.0 − 136.7)/136.7 = 20.0%. % Relative MIDS Transduction = (642.1 − 540.6)/540.6 = 18.8%. The results are plotted in FIG. 30C.

Experiment 4: [Notebook TC_003_117&118]
Remeasured OD 600 nm after dilutions:

| Sample | OD1 | OD2 | OD3 | OD4 | OD5 | OD Average |
|---|---|---|---|---|---|---|
| L(+) MIDS | 0.848 | 0.849 | 0.849 | | | 0.849 |
| D(−) MIDS | 0.845 | 0.848 | 0.849 | 0.849 | 0.849 | 0.848 |
| White Noise | 0.845 | 0.84 | 0.842 | 0.844 | 0.846 | 0.843 |

Used Prior Calibration

Readings were taken in average mode.

| | Fluorescence | | | | | | |
|---|---|---|---|---|---|---|---|
| Sample | rfu1 | rfu2 | rfu3 | rfu4 | rfu5 | rfu6 | Average rfu |
| L(+) Ara MIDS | 527.7 | 531.4 | 531.8 | 535.3 | 535.5 | 534.1 | 532.6 |
| D(−) Ara MIDS | 443.5 | 447.3 | 447.3 | 449.7 | 450.0 | 450.1 | 448.0 |
| White Gaussian Noise | 428.8 | 440.2 | | 493.4 | 444.9 | 445.6 | 450.6 |

% Relative MIDS Transduction = (532.6 − 448.0)/448.0 = 18.9%. The results are plotted in FIG. 30D.

Experiment 5: Shorter induction time 3.5 hrs
Remeasured OD 600 nm after dilutions:

| Sample | OD1 | OD2 | OD3 | OD4 | OD5 | OD Average |
|---|---|---|---|---|---|---|
| L(+) MIDS | 0.839 | 0.853 | 0.847 | 0.846 | 0.841 | 0.845 |
| D(−) MIDS | 0.88 | 0.851 | 0.841 | 0.841 | 0.844 | 0.851 |
| White Noise | 0.839 | 0.836 | 0.85 | 0.834 | | 0.840 |

| | Fluorescence | | | |
|---|---|---|---|---|
| Sample | rfu1 | rfu2 | rfu3 | Average rfu |
| L(+) Ara MIDS | 524.5 | 526.8 | 525.1 | 525.5 |
| D(−) Ara MIDS | 480.3 | 490.8 | 491.5 | 487.5 |
| White Gaussian Noise | 502.1 | 503.2 | 502.6 | 502.6 |

% Relative MIDS Transduction = (525.5 − 487.5)/487.5 = 18.9%. The results are plotted in FIG. 30E.

As noted above, the system utilizes, as input, soundfiles obtained in stochastic resonance experiments and outputs frequencies, amplitudes, and phases of the content sinusoids. The system may employ a software routine, dubbed "peakfinder," which in turn employ other software packages, such as Octave, and Pd, both of which are open-source and currently supported software platforms.

In addition, two environment variables may be used: PF_TMP which specifies a temporary directory and PF_BASE which specifies the location of a peakfinder folder. If PF_BASE is not supplied, a peakfinder.sh script attempts to infer it from its own invocation (assuming it is invoked as an absolute pathname). The input file is a stereo soundfile, assumed to be at a standard sample rate of 44100. The file format may be "wav," "au," or "aiff," in 16, 24, or 32 bit sample frames. The output file is an ASCII file specifying one sinusoid. For instance: TABLE-US-00001 595 100.095749 0.095624 −0.091218 −0.028693 1487 250.155258 0.100177 0.040727 0.091524

TABLE-US-00001

| 595 | 100.095749 | 0.095624 | −0.091218 | −0.028693 |
| 1487 | 250.155258 | 0.100177 | 0.040727 | 0.091524 |

Here the first field is the frequency in units of the fundamental analysis frequency, explained below, the second is the frequency in Hertz, the third is the peak magnitude of the sinusoid, in the input soundfile native units, and the fourth and fifth are the amplitudes of the cosine and sine components of the sinusoid, the real and imaginary parts of the complex amplitude. The magnitude could, of course, be inferred from the real and imaginary components. The first field has no physical meaning and is intended for debugging purposes.

A technique for determining the amplitude and frequency of a single sinusoid in white noise is the Maximum Likelihood (ML) method, which has been extended to multiple sinusoids. This methods assume that the number of sinusoids is known in advance. The problem of finding an un-predetermined number of sinusoids is harder to treat mathematically but can be dealt with assuming that the sinusoids in question are adequately separated in frequency. Furthermore, a method is needed to discriminate between the presence and absence of a sinusoid.

The following analysis starts by considering a single sinusoid in white noise and progresses to the problems of multiple sinusoids and non-white (e.g., pink) noise. Given a measured signal:$x[n]$, $n=0, \ldots, N$, the (discrete-time) unnormalized Fourier transform is defined as: $FT\{x[n]\}(k) = \sum_{n=0}^{N-1} e^{-2\pi i n k/N} x[n]$, where k is the frequency in units of the fundamental frequency of the analysis; $2\pi/N$ radians per sample. k need not be an integer; in practice extra values of k can be filled in as needed by zero-padding the signal. With the assumption that a single sinusoid is present, its most likely frequency is given by: $k = \arg\max |FT\{x[n]\}(k)|$ l. In other words, the best estimate is simply the value of k at which the Fourier transform's magnitude is the largest.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times.

The teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

These and other changes can be made to the invention in light of the above Detailed Description. While the above description details certain embodiments of the invention and describes the best mode contemplated, no matter how detailed the above appears in text, the invention can be practiced in many ways. Details of the signal processing system may vary considerably in its implementation details, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention under the claims.

The invention claimed is:

1. A method for producing an effect of a chemical or biochemical agent on a system, comprising:
   (a) generating a plurality of low-frequency time-domain signals by performing (i), (ii), (iii) and (iv):
      (i) placing a sample containing the chemical or biochemical agent in a container having both magnetic and electromagnetic shielding,
      (ii) injecting noise into the sample at a given noise amplitude;
      (iii) recording an electromagnetic time-domain signal composed of sample source radiation superimposed on the injected noise, and
      (iv) repeating (ii)-(iii) at each of a plurality of noise levels within a selected noise-level range,
   (b) analyzing the plurality of time domain signals generated in (a) by producing spectral plots of the plurality of time-domain signals, and identifying an agent-specific time-domain signal based on information in said spectral plots, and
   (c) exposing the agent-responsive system to the agent-specific time-domain signal identified in (b) by placing the system within the magnetic field of an electromagnetic transducer, and applying said identified agent-specific time-domain signal to said electromagnetic transducer at a signal amplitude and for a period associated with the chemical or biochemical agent sufficient to produce in the system an agent-specific effect on the system,
   wherein the analyzing includes:
   (i) generating a histogram that shows, for each event bin f over a selected frequency range within the range DC to 8 kHz, a number of event counts in each bin, where f is a sampling rate for sampling each of the plurality of recorded electromagnetic time domain signals, assigning to the histogram, a score related to the number of bins that are above a given threshold; and selecting the agent-specific time-domain signal from the plurality of recorded time-domain signals based on said score;
   (ii) autocorrelating each of the plurality of recorded electromagnetic time domain signals, generating an FFT of the autocorrelated signal over a selected frequency range within the range DC to 8 kHz, assigning to the FFT signal, a score related to the number of peaks above a mean average noise value, and selecting the agent-specific time-domain signal from the plurality of recorded time-domain signals based on said score; or
   (iii) calculating a series of Fourier spectra of each of the recorded electromagnetic time-domain signals over each of a plurality of defined time periods, in a selected frequency range between DC and 8 kHz, averaging the Fourier spectra; assigning to the averaged FFT signal, a score related to the number of peaks above a mean average noise value, and selecting the agent-specific time-domain signal based on said score.

2. The method of claim 1, wherein the injected noise is Gaussian noise, and noise is injected into a Helmholtz coil surrounding said sample, at a selected noise output in the range up to 1 volt.

3. The method of claim 1, wherein (b)(i) includes:
   (i) storing a time-domain signal of the sample over a sample-duration time T;

(ii) selecting a sampling rate F for sampling the stored time domain signal, where F*T is the total sample count S, F is approximately twice the frequency domain resolution f of a Real Fast Fourier Transform of the time-domain signal sampled at sampling rate F, and S>(2)f*n, where n is at least 10, (iii) selecting S/n samples from the stored time domain signal and performing a Real Fast Fourier Transform (RFFT) on the samples, (iv) normalizing the RFFT signal and calculating an average power for the signal, (v) placing an event count in each of f selected-frequency event bins where the measured power at the corresponding selected frequency≥average power*∈ obtains, where 0<∈<1, and is chosen such that the total number of counts placed in an event bin is between about 20-50% of the maximum possible bin counts in that bin, (vi) repeating (iii-v) N>2 times, and (viii) generating a histogram that shows, for each event bin f over a selected frequency range, the number of event counts in each bin.

4. The method of claim 3, which further includes, in (iv) for normalizing the RFFT signal includes placing the normalized power value from the RFFT in f corresponding-frequency power bins, and in (viii) performing the following: (a) dividing the accumulated values placed in each of the f power bins by n, to yield an average power in each bin, and (b) displaying on the histogram, the average power in each bin.

5. The method of claim 1, wherein said recording is carried out using a gradiometer coupled to a SQUID, and said injecting includes injecting noise into said gradiometer.

6. The method of claim 1, wherein exposing the system comprises:
exposing the system that includes a biological system responsive to the presence of an agent known to bind to an acceptor in the biological system to produce an agent-specific effect to said identified agent-specific time-domain signal.

7. The method of claim 6 wherein the biological system includes one or more genes that are upregulated or downregulated by the presence of said agent, and exposing the biological system to said identified agent-specific time-domain signal is carried out at a signal amplitude and for a time sufficient to produce a measurable upregulation or downregulation of said gene.

8. The method of claim 6, wherein exposing the system comprises:
exposing the system that includes a mammalian target to generate an antibiotic response in the mammalian target.

9. The method of claim 8, wherein the antibiotic response is associated with ampicillin.

10. The method of claim 1, wherein exposing the system comprises:
exposing the system that includes an *E. coli* target to generate a lac-operon induction response in the *E. coli* target, wherein the peaks correspond to frequencies of stochastic events produced by arabinose L(+).

11. The method of claim 1, wherein exposing the system comprises:
exposing the system that includes a plant target to generate a growth-inhibitory response in the plant target, wherein the peaks correspond to frequencies of stochastic events produced by glyphosate.

12. The method of claim 1, wherein exposing the system comprises:
exposing the system that includes a plant target to generate a growth-inhibitory response in the plant target, wherein the peaks correspond to frequencies of stochastic events produced by gibberellin.

13. The method of claim 1, wherein exposing the system comprises:
exposing the system that includes a system responsive to the presence of an agent known to promote binding between or assembly of one or more components in a given system, and exposing said system to said identified agent-specific time-domain signal is carried out at a signal amplitude and for a duration sufficient to promote a level of binding between or assembly of said one or more components than is greater than that observed prior to said exposing.

14. The method of claim 1, wherein said electromagnet transducer includes a coil winding defining an open interior, and said exposing includes placing the sample within an open interior of said winding.

15. The method of claim 1, wherein said electromagnet transducer includes an implantable coil, and said transducer including the implantable coil is implanted in the system that includes a biological system prior to said exposing.

16. A method for treating a tumor in a mammalian subject, comprising:

(a) generating a plurality of low-frequency time-domain signals by performing the following:
(i) placing a sample containing a cancer chemotherapeutic agent in a container having both magnetic and electromagnetic shielding,
(ii) injecting noise into the sample at a given noise amplitude;
(iii) recording an electromagnetic time-domain signal composed of sample source radiation superimposed on the injected noise, and
(iv) repeating (ii)-(iii) at each of a plurality of noise levels within a selected noise-level range, (b) analyzing the plurality of recorded electromagnetic time domain signals generated in (a) by producing spectral plots of the plurality of recorded electromagnetic time-domain signals, and identifying an agent-specific time-domain signal based on information in said spectral plots, and (c) exposing the mammalian subject to the agent-specific time-domain signal identified in (b) by placing the mammalian subject within the magnetic field of an electromagnetic transducer, and applying said agent-specific time-domain signal to said electromagnetic transducer at a signal amplitude and for a period sufficient to produce a reduction in the size and/or rate of growth of a tumor in the subject, wherein the analyzing includes:

(i) generating a histogram that shows, for each event bin f over a selected frequency range within the range DC to 8 kHz, a number of event counts in each bin, where f is a sampling rate for sampling each of the plurality of recorded electromagnetic time domain signals, assigning to the histogram, a score related to the number of bins that are above a given threshold; and selecting the agent-specific time-domain signal from the plurality of recorded time-domain signals based on said score;

(ii) autocorrelating each of the plurality of recorded electromagnetic time domain signals, generating an FFT of the autocorrelated signal over a selected frequency range within the range DC to 8 kHz, assigning to the FFT signal, a score related to the number of peaks above a mean average noise value, and selecting the agent-specific time-domain signal from the plurality of recorded time-domain signals based on said score; or (iii) calculating a series of Fourier spectra of each of the recorded electromagnetic time-domain signals over each of a plurality of defined time periods, in a selected frequency range between DC and 8 kHz, averaging the Fourier spectra; assigning to the averaged FFT signal, a score related to the number of peaks above a mean average noise value, and selecting the agent-specific time-domain signal based on said score.

* * * * *